(12) United States Patent
Cha et al.

(10) Patent No.: US 11,515,478 B2
(45) Date of Patent: Nov. 29, 2022

(54) COMPOUND AND ORGANIC LIGHT EMITTING DEVICE USING THE SAME

(71) Applicant: LG CHEM, LTD., Seoul (KR)

(72) Inventors: Yong Bum Cha, Daejeon (KR); Sang Duk Suh, Daejeon (KR); Yeon Hwan Kim, Daejeon (KR); Sang Young Jeon, Daejeon (KR); Sung Jae Lee, Daejeon (KR)

(73) Assignee: LG CHEM LTD., Seoul (KR)

( * ) Notice: Subject to any disclaimer, the term of this patent is extended or adjusted under 35 U.S.C. 154(b) by 554 days.

(21) Appl. No.: 16/463,299

(22) PCT Filed: Feb. 23, 2018

(86) PCT No.: PCT/KR2018/002276
§ 371 (c)(1),
(2) Date: May 22, 2019

(87) PCT Pub. No.: WO2018/216887
PCT Pub. Date: Nov. 29, 2018

(65) Prior Publication Data
US 2019/0378990 A1    Dec. 12, 2019

(30) Foreign Application Priority Data

May 22, 2017    (KR) ........................ 10-2017-0063092

(51) Int. Cl.
   *H01L 51/00*    (2006.01)
   *C07D 213/16*    (2006.01)
   (Continued)

(52) U.S. Cl.
   CPC ........ *H01L 51/0056* (2013.01); *C07D 213/16* (2013.01); *C07D 239/26* (2013.01);
   (Continued)

(58) Field of Classification Search
   CPC ............. H01L 51/0056; H01L 51/0054; H01L 51/0058; H01L 51/0067; H01L 51/0072;
   (Continued)

(56) References Cited

U.S. PATENT DOCUMENTS 7,318,966 B2    1/2008    Tominaga et al.
2007/0051944 A1    3/2007    Vestweber et al.
(Continued)

FOREIGN PATENT DOCUMENTS

CN    101440082 A    5/2009
CN    102270751 A    12/2011
(Continued)

*Primary Examiner* — Michael Y Sun
(74) *Attorney, Agent, or Firm* — Dentons US LLP

(57) ABSTRACT

The present disclosure relates to a compound represented by Chemical Formula 1 and an organic light emitting device using the same. The compound is used as a material of an organic material layer of the organic light emitting device.

[Chemical Formula 1]

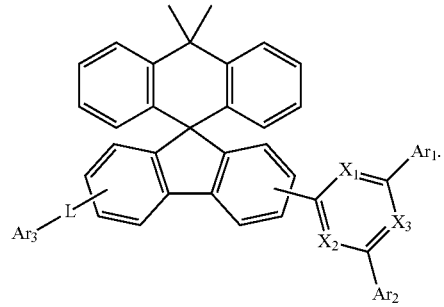

9 Claims, 1 Drawing Sheet

| 4 |
|---|
| 8 |
| 7 |
| 6 |
| 5 |
| 2 |
| 1 |

(51) Int. Cl.
*C07D 239/26* (2006.01)
*C07D 251/24* (2006.01)
*C07D 403/10* (2006.01)
*C07D 405/10* (2006.01)
*C09K 11/06* (2006.01)
*H01L 51/50* (2006.01)

(52) U.S. Cl.
CPC ......... *C07D 251/24* (2013.01); *C07D 403/10* (2013.01); *C07D 405/10* (2013.01); *C09K 11/06* (2013.01); *H01L 51/0054* (2013.01); *H01L 51/0058* (2013.01); *H01L 51/0067* (2013.01); *H01L 51/0072* (2013.01); *H01L 51/0073* (2013.01); *C09K 2211/1018* (2013.01); *H01L 51/5012* (2013.01); *H01L 51/5016* (2013.01); *H01L 51/5072* (2013.01)

(58) Field of Classification Search
CPC ............ H01L 51/0073; H01L 51/5012; H01L 51/5016; H01L 51/5072; H01L 51/00; H01L 51/50; H01L 51/5056; H01L 51/5088; H01L 51/5092; C07D 213/16; C07D 239/26; C07D 251/24; C07D 403/10; C07D 405/10; C07D 401/10; C07D 409/10; C07D 491/048; C07D 495/04; C07D 519/00; C09K 11/06; C09K 2211/1018

See application file for complete search history.

(56) References Cited

U.S. PATENT DOCUMENTS

| | | | | |
|---|---|---|---|---|
| 2011/0121274 | A1* | 5/2011 | Parham | H01L 51/0058 252/301.16 |
| 2015/0115241 | A1 | 4/2015 | Zoellner et al. | |
| 2015/0162543 | A1* | 6/2015 | Lee | H01L 51/0074 136/263 |
| 2016/0043323 | A1 | 2/2016 | Yam et al. | |
| 2016/0308129 | A1 | 10/2016 | Stoessel et al. | |
| 2017/0222157 | A1* | 8/2017 | Jatsch | H01L 51/0073 |
| 2018/0002256 | A1 | 1/2018 | Cha et al. | |

FOREIGN PATENT DOCUMENTS

| | | |
|---|---|---|
| CN | 103435597 A | 12/2013 |
| CN | 103666454 A | 3/2014 |
| CN | 103923065 A | 7/2014 |
| CN | 104342120 A | 2/2015 |
| CN | 105601558 A | 5/2016 |
| CN | 105837498 A | 8/2016 |
| CN | 106588674 A | 4/2017 |
| CN | 107141191 A | 9/2017 |
| JP | 2003096072 A | 4/2003 |
| JP | 2007-520875 A | 7/2007 |
| JP | 2011-530802 A | 12/2011 |
| KR | 1020000051826 A | 8/2000 |
| KR | 1020130140303 A | 12/2013 |
| KR | 1020140009019 A | 1/2014 |
| KR | 10-2014-0029182 A | 3/2014 |
| KR | 10-2015-0031396 A | 3/2015 |
| KR | 1020150095545 A | 5/2015 |
| KR | 10-2015-0121394 A | 10/2015 |
| KR | 1020160102949 A | 8/2016 |
| KR | 1020170032414 A | 3/2017 |
| TW | 201636323 A | 10/2016 |
| WO | 2003012890 A2 | 2/2003 |
| WO | 2013149958 A1 | 10/2013 |
| WO | 2016/012075 A1 | 1/2016 |
| WO | 2016023458 A1 | 2/2016 |

* cited by examiner

[FIG. 1]

| |
|---|
| 4 |
| 3 |
| 2 |
| 1 |

[FIG. 2]

| |
|---|
| 4 |
| 8 |
| 7 |
| 6 |
| 5 |
| 2 |
| 1 |

COMPOUND AND ORGANIC LIGHT EMITTING DEVICE USING THE SAME

CROSS-REFERENCE TO RELATED APPLICATION(S)

This application claims the benefit of priority from Korean Patent Application No. 10-2017-0063092, filed May 22, 2017, the full disclosure of which is incorporated herein by reference.

TECHNICAL FIELD

The present disclosure relates to a novel compound and an organic light emitting device comprising the same.

BACKGROUND ART

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently have a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and the electrons meet each other, an exciton is formed, and light is emitted when the exciton falls to a ground state again.

There is a continuing need for the development of new materials for the organic materials used in such organic light emitting devices,

RELATED ART

Patent Literature (Patent Literature 0001) Korean Patent Laid-open Publication No. 10-2000-0051826

DETAILED DESCRIPTION OF THE DISCLOSURE

Technical Problem

It is an object of the present disclosure to provide a novel compound and an organic light emitting device comprising the same.

Technical Solution

In order to achieve the above objects, the present disclosure provides a compound represented by Chemical Formula 1 below:

[Chemical Formula 1]

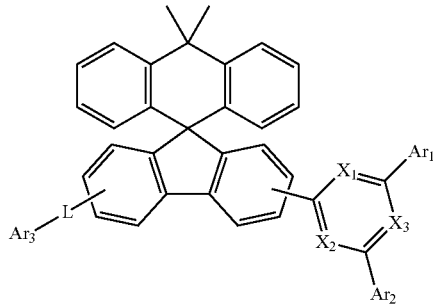

wherein, in Chemical Formula 1, $X_1$ to $X_3$ is each independently N, or CH, and at least one of $X_1$ to $X_3$ is N, $Ar_1$ and $Ar_2$ are each independently a substituted or unsubstituted $C_{6-60}$ aryl; or a substituted or unsubstituted $C_{2-60}$ heteroaryl containing one or more heteroatoms selected from the group consisting of N, O and S;

L is a bond; or a substituted or unsubstituted $C_{6-60}$ arylene, and $Ar_3$ is a substituted or unsubstituted $C_{6-60}$ aryl; or a substituted or unsubstituted $C_{2-60}$ heteroaryl containing one or more heteroatoms selected from the group consisting of N, O and S.

The present disclosure also provides an organic light emitting device comprising a first electrode; a second electrode provided at a side opposite to the first electrode; and at least one layer of the organic material layers provided between the first electrode and the second electrode, wherein the at least one layer of the organic material layers includes a compound represented by Chemical Formula 1.

Advantageous Effects

The compound represented by the Chemical Formula 1 can be used as a material of an organic material layer of an organic light emitting element, and can achieve an improvement of the efficiency, a low driving voltage and/or an improvement of the lifetime characteristic when applied to the organic light emitting device.

BRIEF DESCRIPTION OF DRAWINGS

FIG. 1 shows an example of an organic light emitting device comprising a substrate 1, an anode 2, a light emitting layer 3, and a cathode 4.

FIG. 2 shows an example of an organic light emitting device comprising a substrate 1, an anode 2, a hole injection layer 5, a hole transport layer 6, a light emitting layer 7, an electron transport layer 8, and a cathode 4.

DETAILED DESCRIPTION OF THE EMBODIMENTS

Hereinafter, the present disclosure will be described in more detail to help understanding of the present disclosure. In the present specification,

means a bond connected to another substituent group.

As used herein, the term "substituted or unsubstituted" means that substitution is performed by one or more substituent groups selected from the group consisting of deuterium; a halogen group; a nitrile group; a nitro group; a hydroxyl group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; or a heterocyclic group containing at least one of N, O, and S atoms, or there is no substituent group, or substitution is performed by a substituent group where two or more substituent groups of the exemplified substituent groups are linked or there is no substituent group. For example, the term "substituent group where two or more substituent groups are linked" may be a biphenyl group. That is, the biphenyl group may be an aryl group, or may be interpreted as a substituent group where two phenyl groups are connected.

In the present specification, the number of carbon atoms in a carbonyl group is not particularly limited, but is preferably 1 to 40 carbon atoms, Specifically, the carbonyl group may be compounds having the following structures, but is not limited thereto.

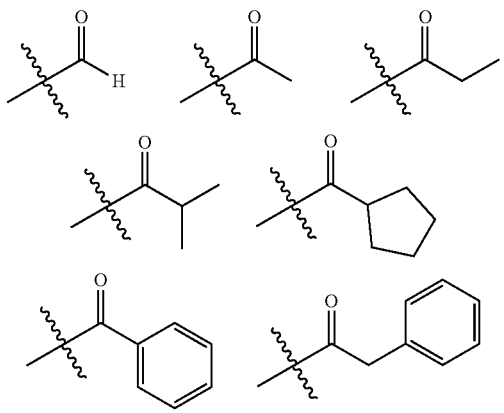

In the present specification, the ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be compounds having the following structures, but is not limited thereto.

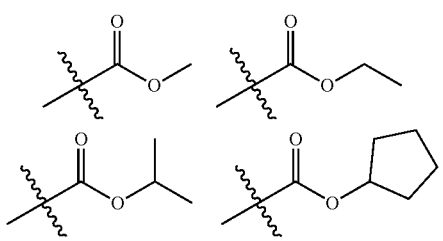

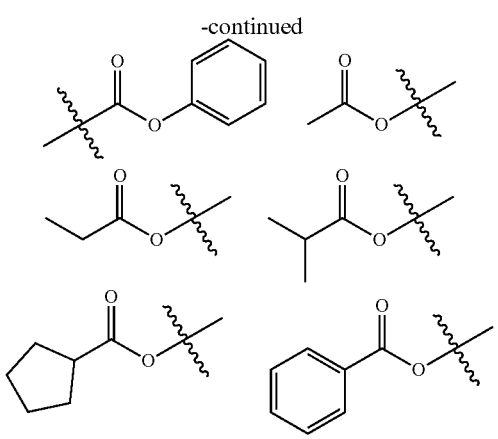

In the present specification, the number of carbon atoms in an imide group is not particularly limited, but is preferably 1 to 25. Specifically, the imide group may be compounds having the following structures, but is not limited thereto.

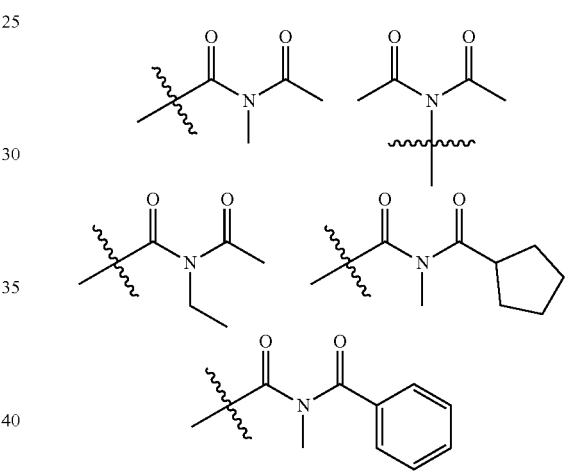

In the present specification, the silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present specification, the boron group specifically includes a trimethylboron group, a triethylboron group, a t-butyldimethylboron group, a triphenylboron group, a phenylboron group, and the like, but is not limited thereto.

In the present specification, examples of a halogen group include fluorine, chlorine, bromine, or iodine.

In the present specification, an alkyl group may be a straight chain or a branched chain, and the number of carbon atoms thereof is not particularly limited, but is preferably 1 to 40. According to one embodiment, the alkyl group has 1 to 20 carbon atoms. According to another embodiment, the alkyl group has 1 to 10 carbon atoms. According to still another embodiment, the alkyl group has 1 to 6 carbon atoms. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the alkenyl group may be a straight chain or a branched chain, and the number of carbon atoms thereof is not particularly limited, but is preferably 2 to 40. According to one embodiment, the alkenyl group has 2 to 20 carbon atoms. According to another embodiment, the alkenyl group has 2 to 10 carbon atoms. According to still another embodiment, the alkenyl group has 2 to 6 carbon atoms. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenyl-vinyl-1-yl, 2-phenyl-2-(naphthyl-1-yl)vinyl-1-yl, 2,2-bis(di-phenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the cycloalkyl group has 3 to 30 carbon atoms. According to another embodiment, the cycloalkyl group has 3 to 20 carbon atoms. According to another embodiment, the cycloalkyl group has 3 to 6 carbon atoms. Specific examples thereof include cyclopropyl, cyclobutyl, cyclopentyl, 3-methylcyclopentyl, 2,3-dim ethylcyclopentyl, cyclohexyl, 3-methylcyclohexyl, 4-methylcyclohexyl, 2,3-dimethylcy-clohexyl, 3,4,5-trimethylcyclohexyl, 4-tert-butylcyclohexyl, cycloheptyl, cyclooctyl, and the like, but are not limited thereto.

In the present specification, the aryl group is not particularly limited, but preferably has 6 to 60 carbon atoms, and may be a monocyclic aryl group or a polycyclic aryl group. According to one embodiment, the aryl group has 6 to 30 carbon atoms. According to one embodiment, the aryl group has 6 to 20 carbon atoms. The aryl group may be a phenyl group, a biphenyl group, a terphenyl group or the like as the monocyclic aryl croup, but is not limited thereto. Examples of the polycyclic aryl group include a naphthyl group, an anthracenyl group, a phenanthryl group, a pyrenyl group, a perylenyl group, a chrycenyl group, a fluorenyl group or the Ike, but is not limited thereto.

In the present specification, a fluorenyl group may be substituted, and two substituent groups may be linked with each other to form a Spiro structure. In the case where the fluorenyl group is substituted,

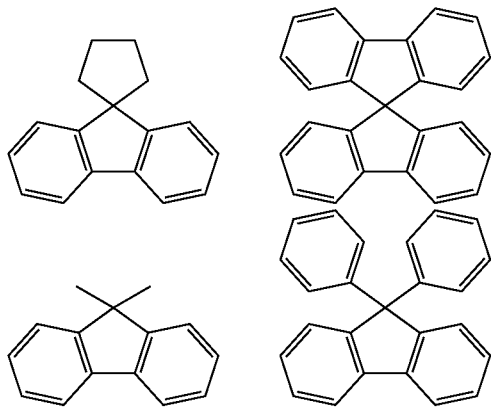

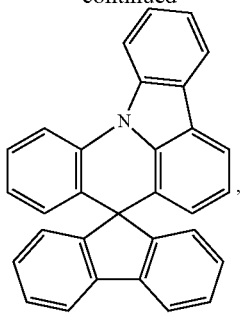

and the like can be formed. However, the structure is not limited thereto.

In the present specification, the heterocyclic group is a heterocyclic group containing at least one of O, N, Si and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidi-nyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothi-ophene group, a dibenzothiophene group, a benzofuranyl group, a phenanthroline group, an isoxazolyl group, a thia-diazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group and the alkylamine group is the same as the aforementioned examples of the alkyl group. In the present specification, the heteroaryl in the heteroarylamines can be applied to the aforementioned description of the heterocyclic group. In the present specification, the alkenyl group in the aralkenyl group is the same as the aforementioned examples of the alkenyl group. In the present specification, the aforementioned description of the aryl group may be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but formed by combining two substituent groups. In the present specification, the aforementioned description of the heterocyclic group can be applied, except that the heterocycle is not a monovalent group but formed by combining two substituent groups.

In accordance with the bonding position in Chemical Formula 1, the Chemical Formula 1 may be represented by Chemical Formula 1-1 below:

[Chemical Formula 1-1]

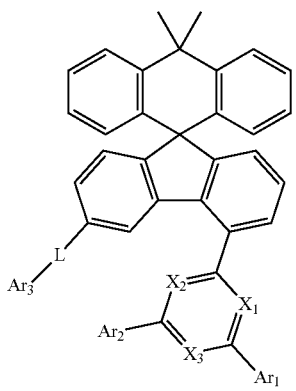

Preferably, Ar$_1$ and Ar$_2$ are each independently phenyl, biphenylyl, terphenylyl, quaterphenylyl, naphthyl, anthracenyl, phenanthrenyl, triphenylenyl, dimethylfluorenyl, diphenylfluorenyl, dibenzofuranyl, carbazolyl, 9-phenylcarbazolyl, or dibenzothiophenyl. More preferably, Ar$_1$ and Ar$_2$ are each independently phenyl, or biphenylyl.

Preferably, L is a bond, phenylene, naphthalenediyl, or anthracenediyl.

Preferably, Ar$_3$ is phenyl, biphenyl, terphenylyl, quaterphenylyl, naphthyl, phenanthrenyl, anthracenyl, triphenylenyl, dimethylfluorenyl, diphenylfluorenyl, dibenzofuranyl, dibenzothiophenyl, carbazolyl, 9-phenylcarbazolyl, quinolinyl, isoquinolinyl, a substituent represented by Chemical Formula 2 below, or a substituent represented by Chemical Formula 3; below and the Ar$_3$ is unsubstituted or substituted by cyano.

[Chemical Formula 2]

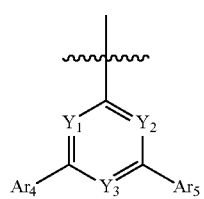

in Chemical Formula 2,

Y$_1$ to Y$_3$ are each independently N, or CH, provided that at least one of Y$_1$ to Y$_3$ is N, and Ar$_4$ and Ar$_5$ are each independently a substituted or unsubstituted C$_{6-60}$ aryl,

[Chemical Formula 3]

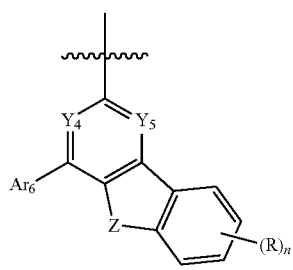

in Chemical Formula 3.

Y$_4$ and Y$_5$ are each independently N or CH, provided that at least one of Y$_4$ and Y$_5$ is N, and Z is O or S, Ar$_6$ is a substituted or unsubstituted C6-60 aryl; or a substituted or unsubstituted C$_{2-60}$ heteroaryl containing one or more heteroatoms selected from the group consisting of N, O and S;

R is hydrogen; a substituted or unsubstituted C$_{6-60}$ aryl; or a substituted or unsubstituted C$_{2-60}$ heteroaryl containing one or more heteroatoms selected from the group consisting of N, O and S, and n is an integer of 1 to 4.

Preferably, in Chemical Formula 2, Ar$_4$ and Ar$_5$ are each independently phenyl, biphenylyl, or naphthyl.

Preferably, in Chemical Formula 3, Ar$_6$ is phenyl, biphenylyl, dimethylfluorenyl, diphenylfluorenyl, dibenzofuranyl, dibenzothiophenyl, carbazolyl, or 9-phenylcarbazolyl. Further, preferably, in Chemical Formula 3, R is hydrogen.

Representative examples of the compound represented by Chemical Formula 1 are as follows:

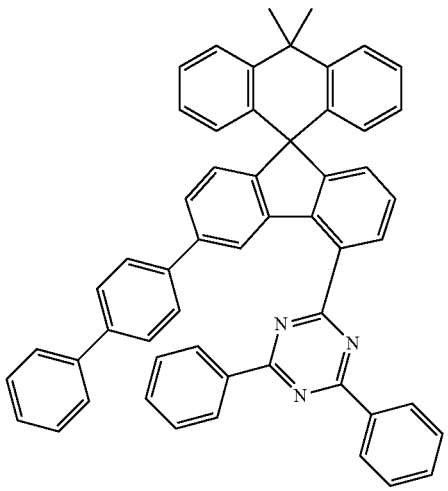

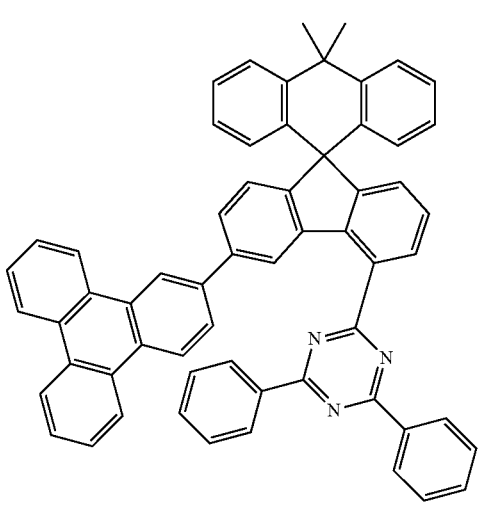

-continued
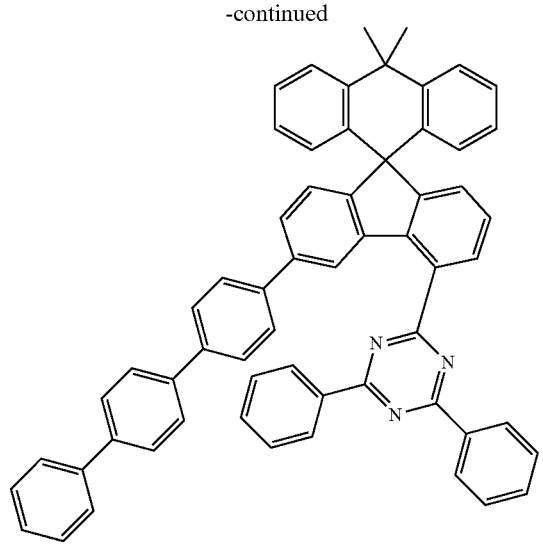
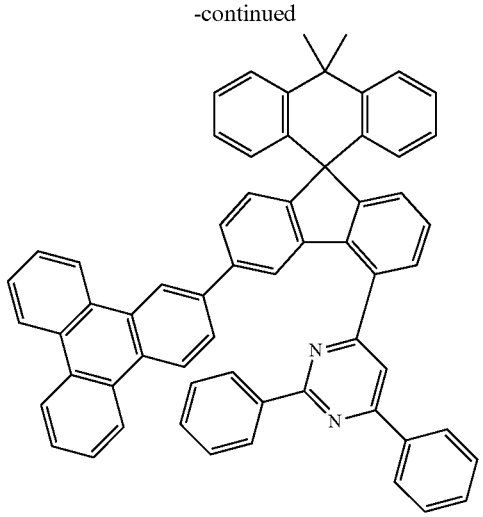
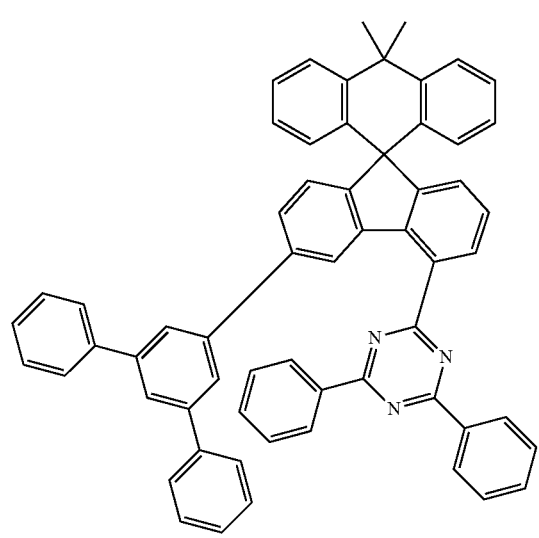
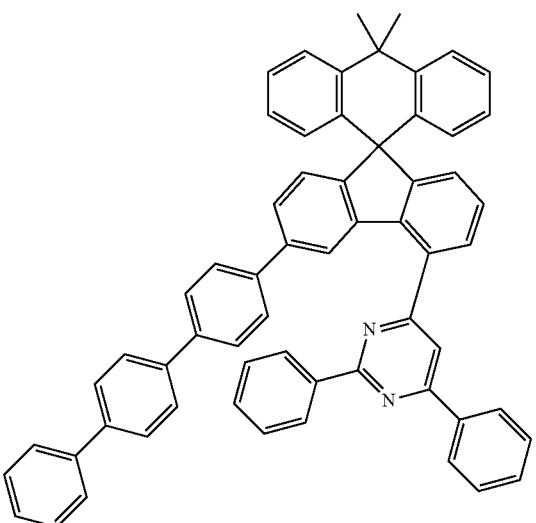
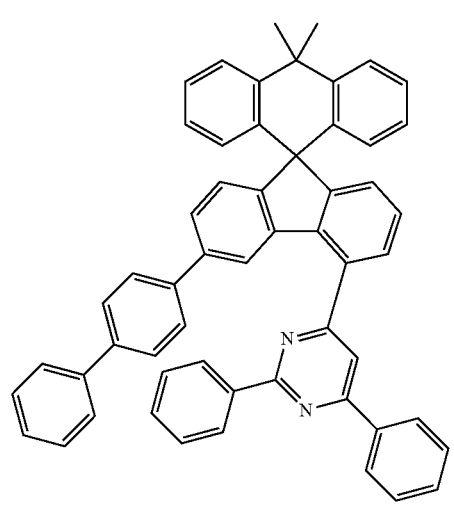
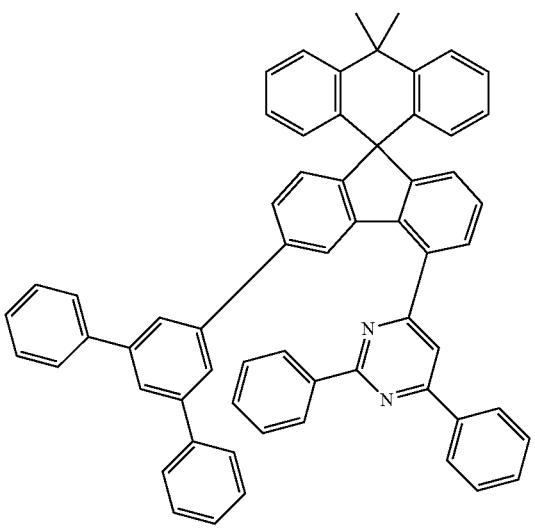

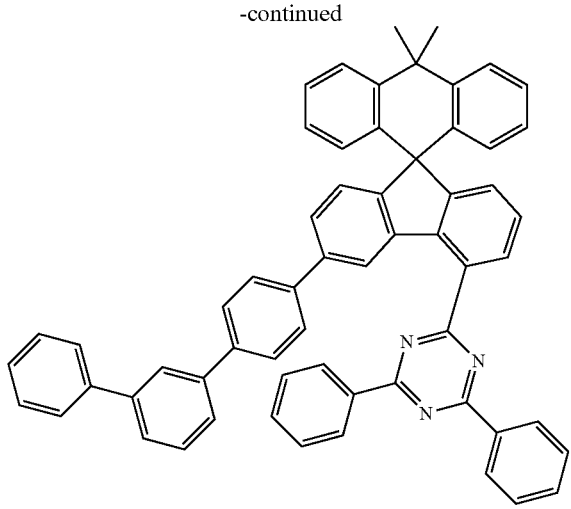
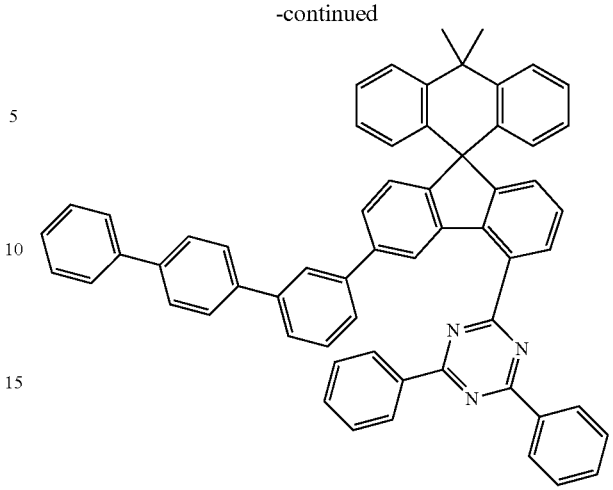
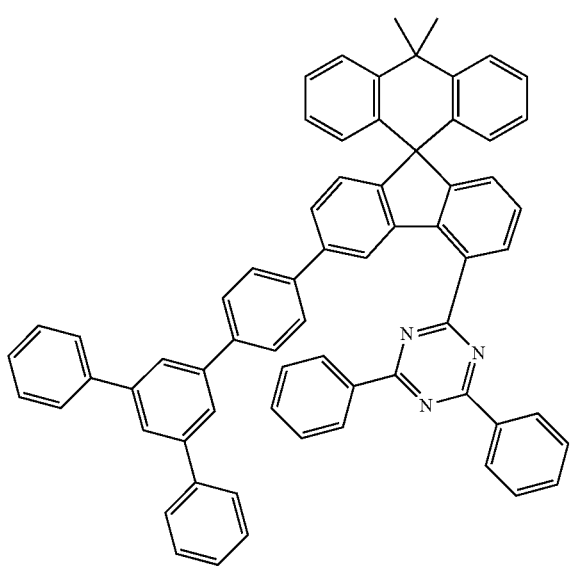
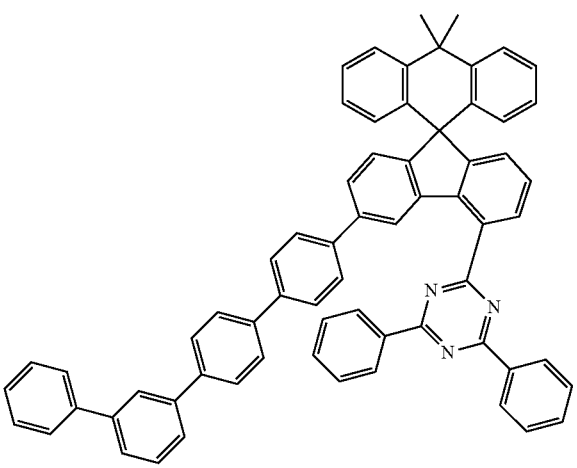
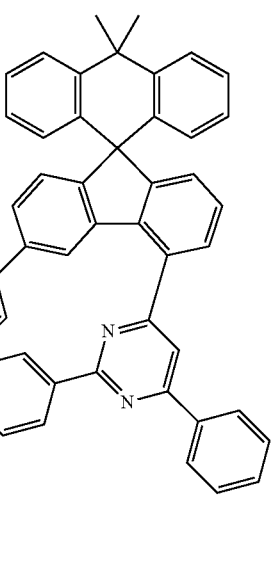

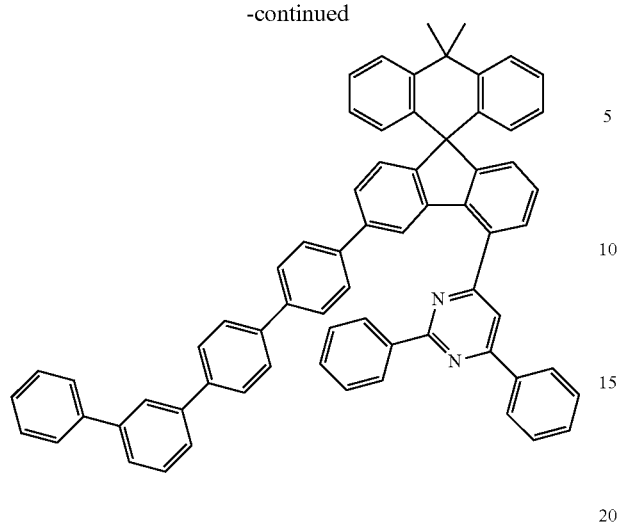
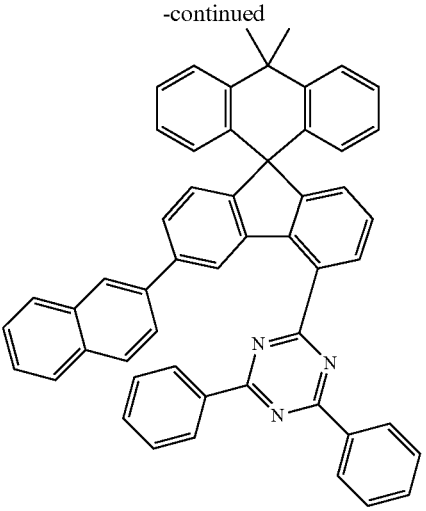
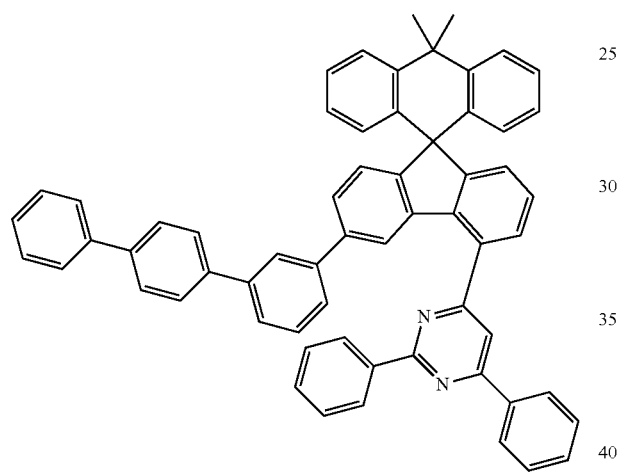
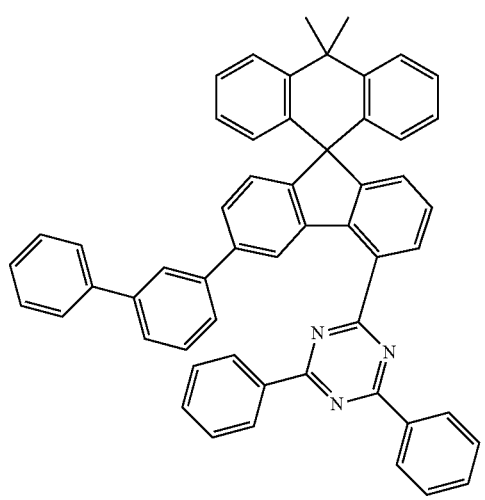
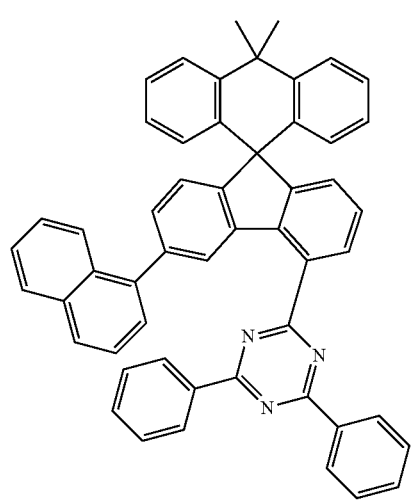
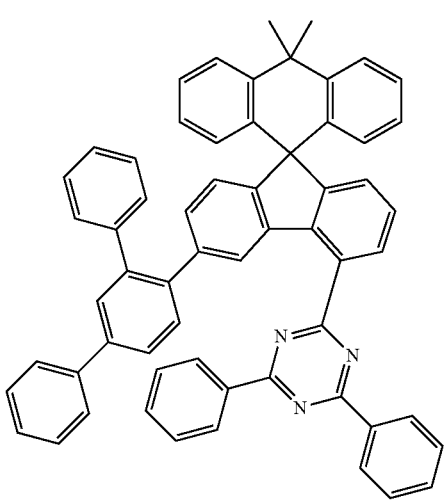

15
-continued
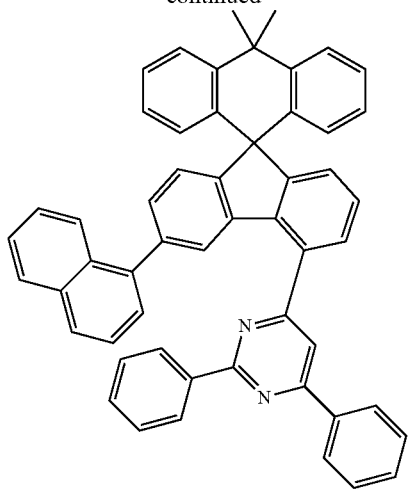
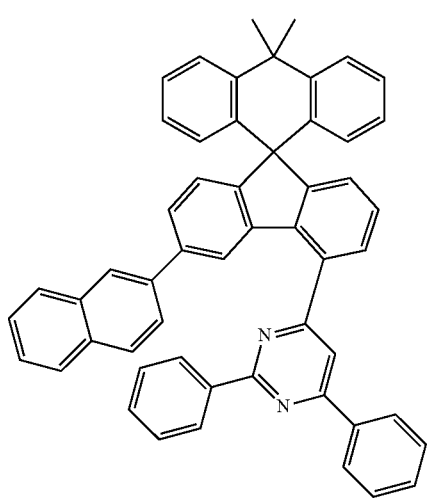
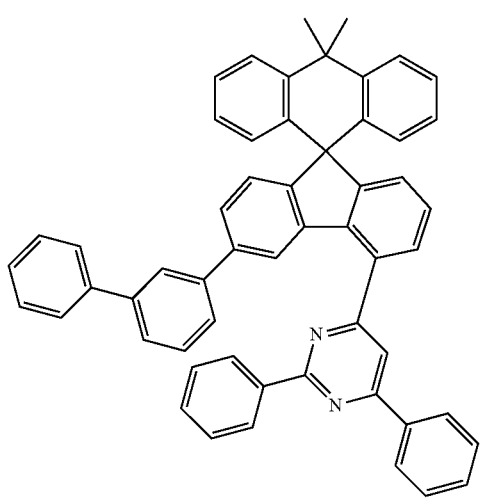
16
-continued
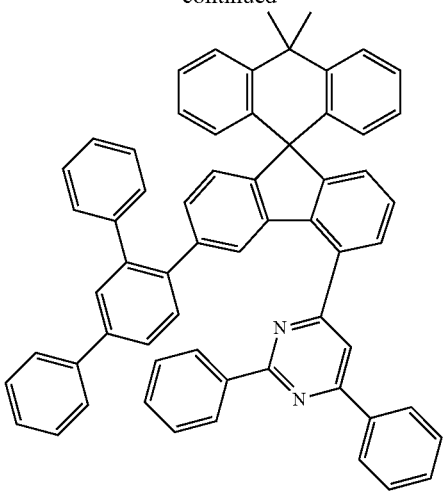
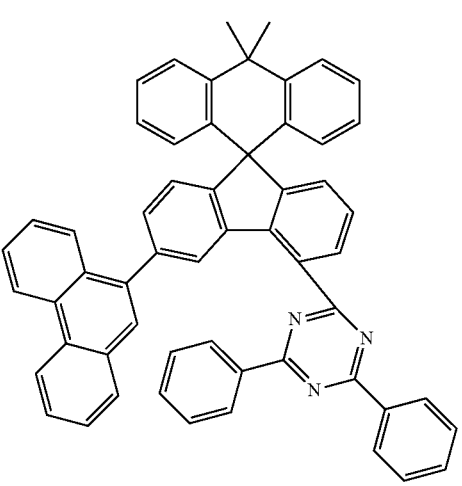
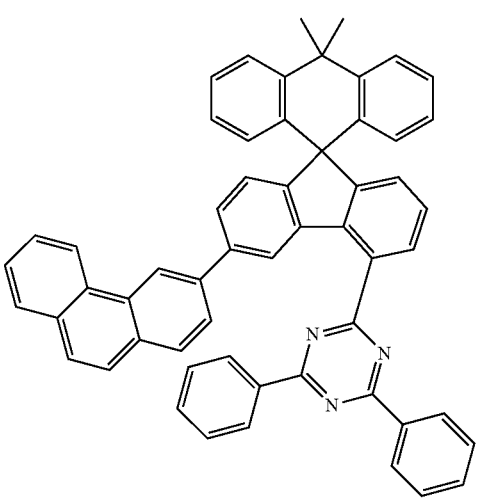

-continued
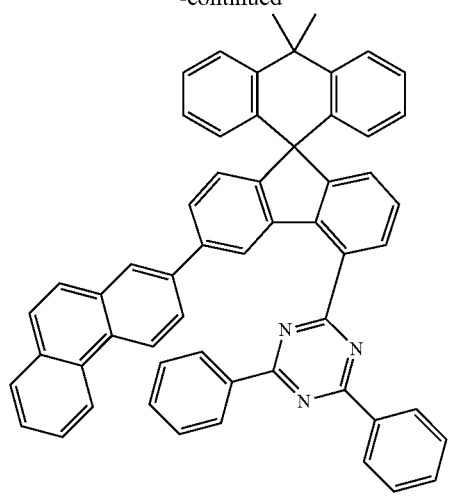
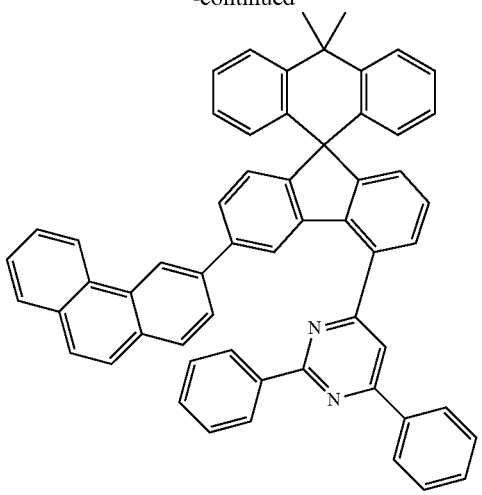
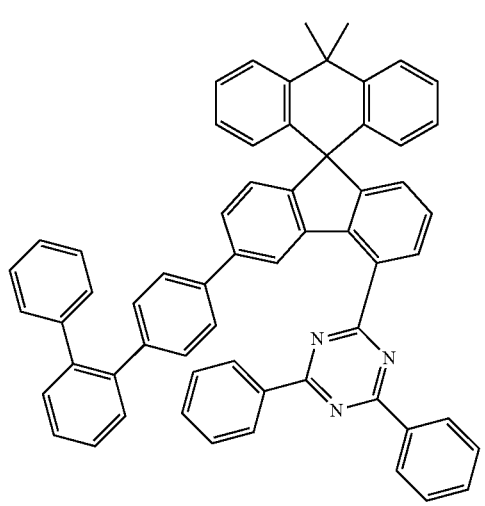
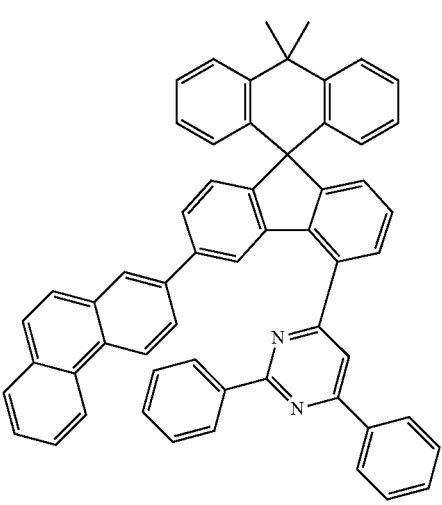
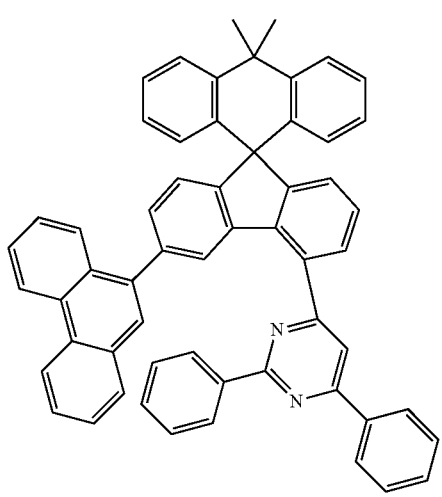
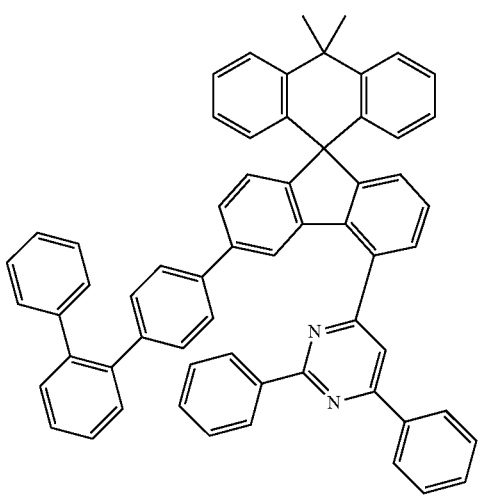

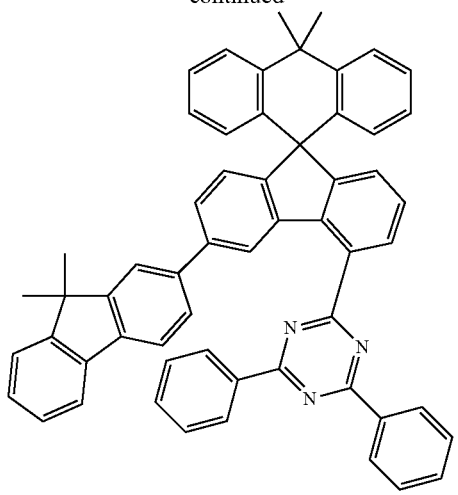
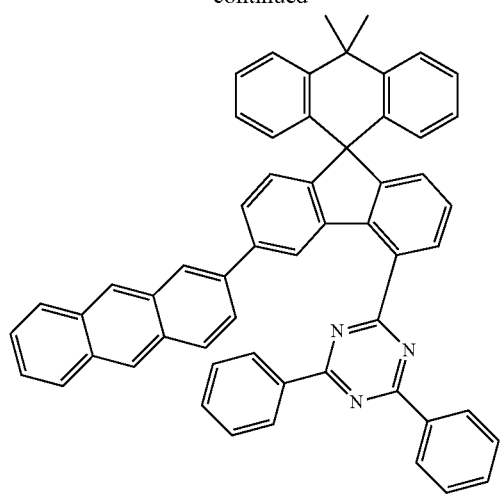
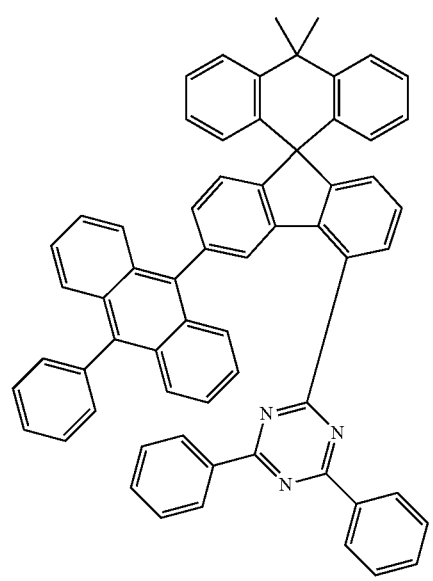
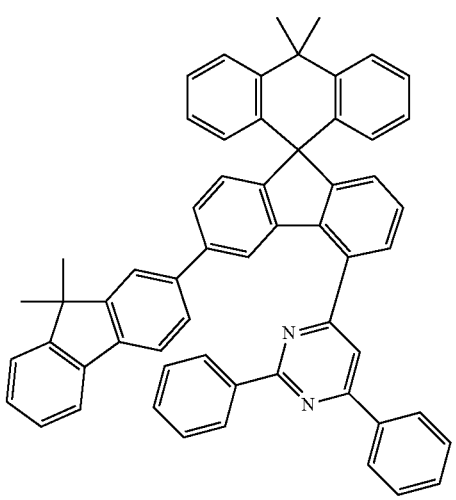
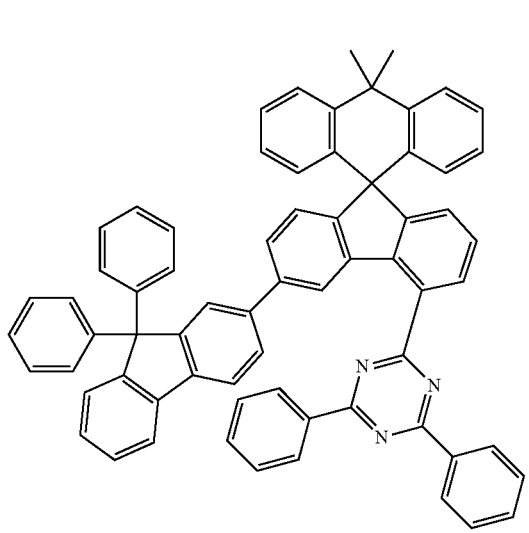
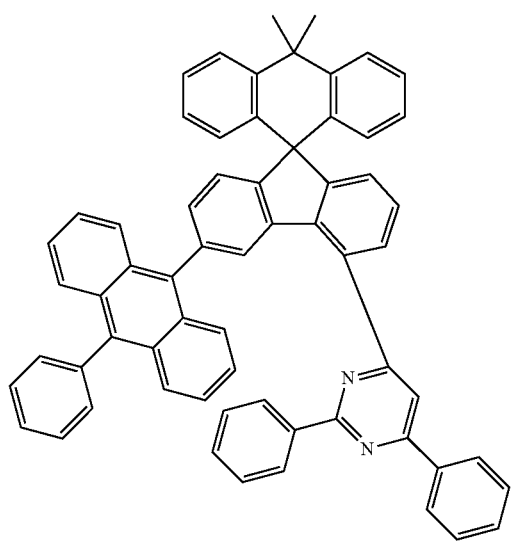

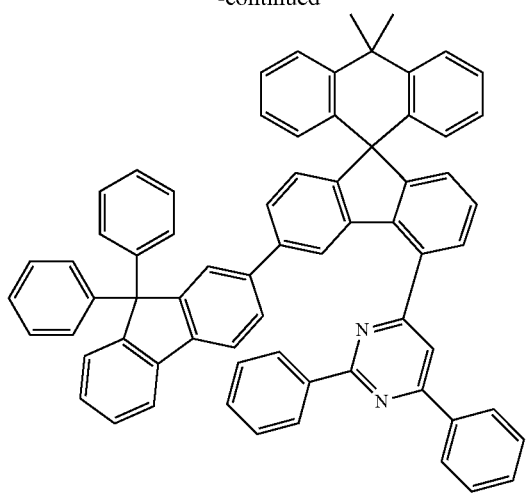
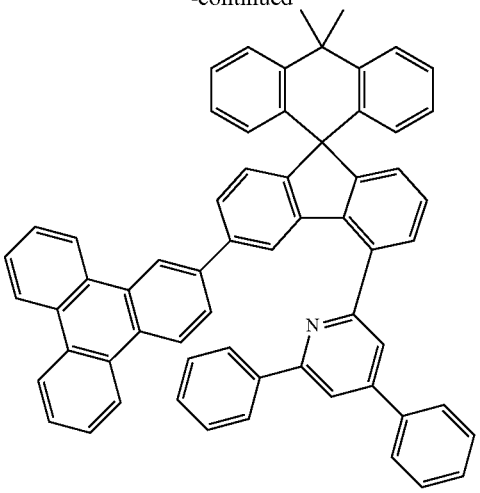
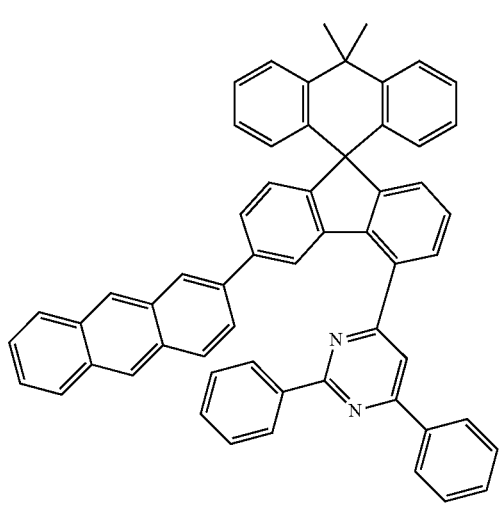
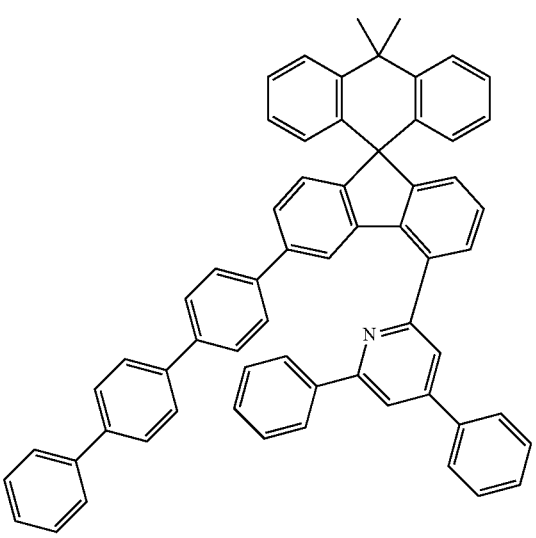
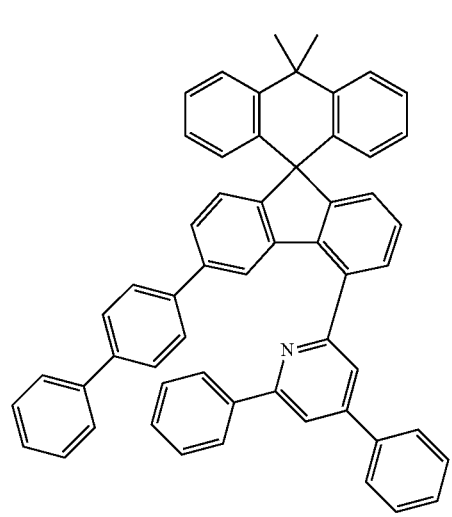
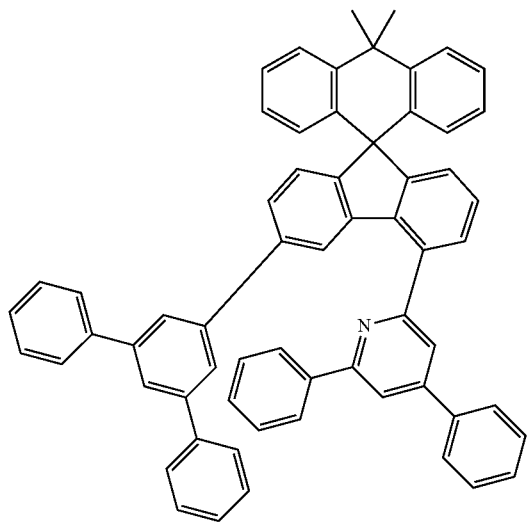

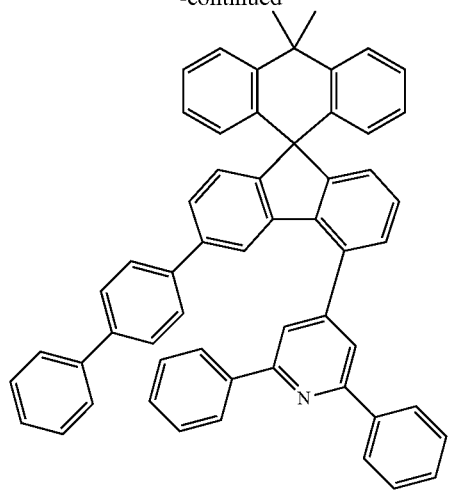
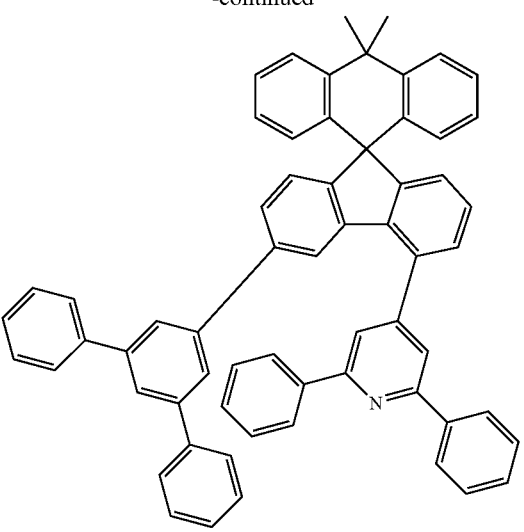
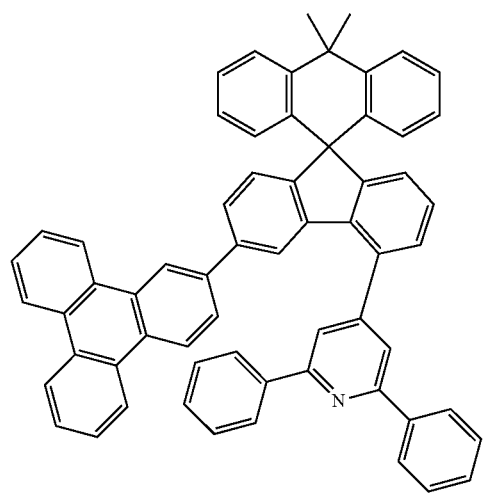
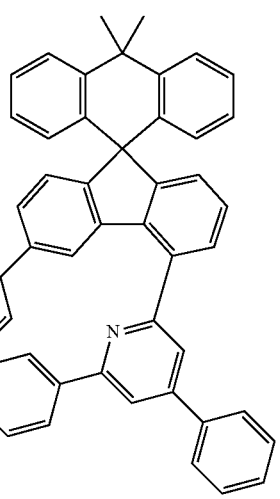
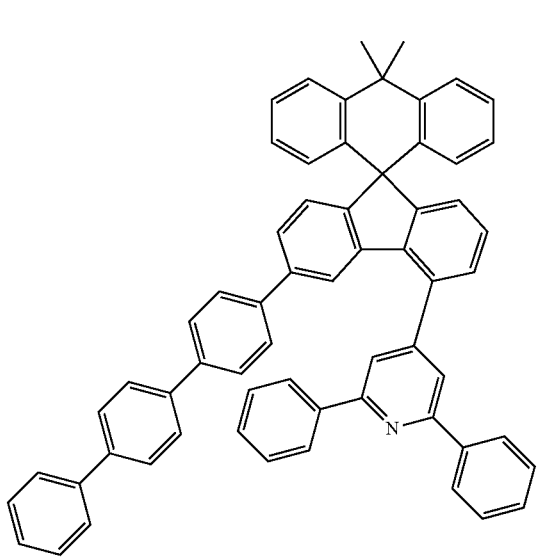
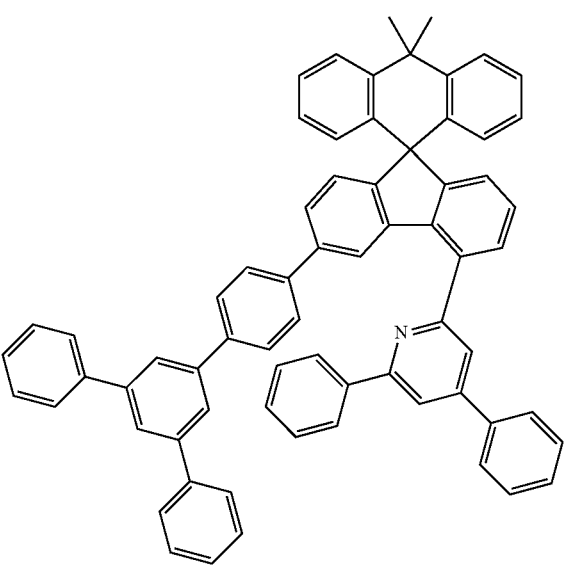

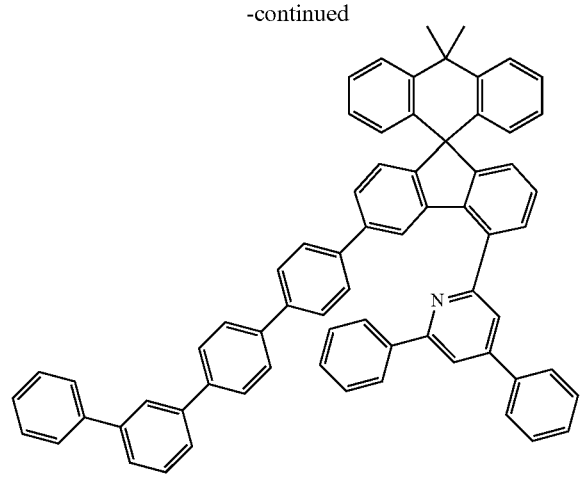
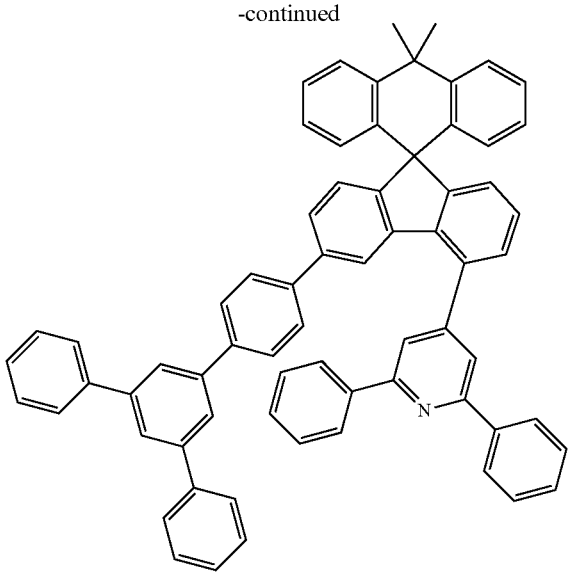
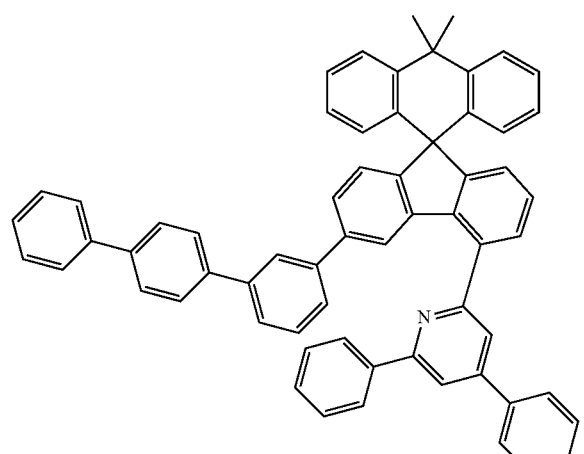
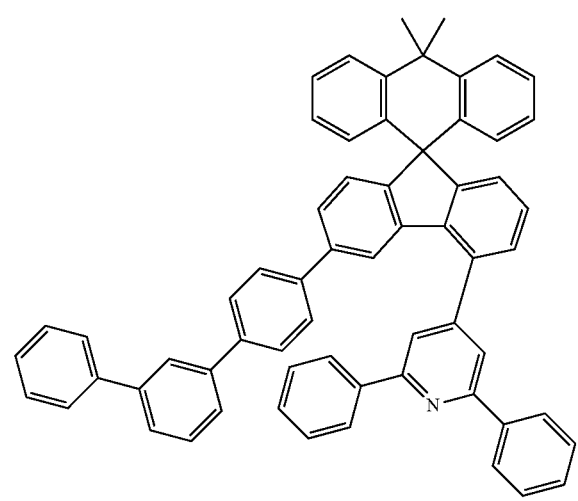
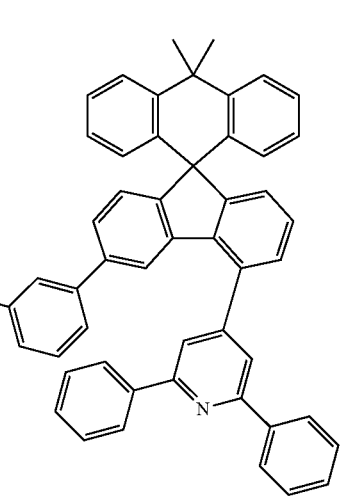

27
-continued
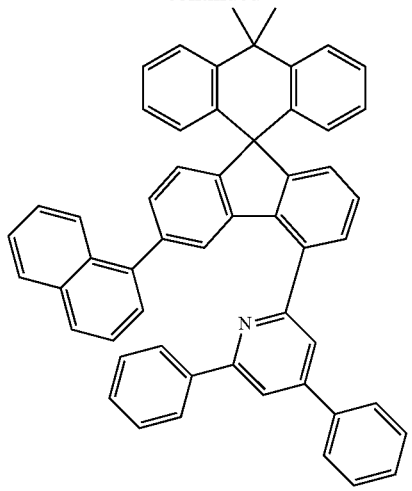
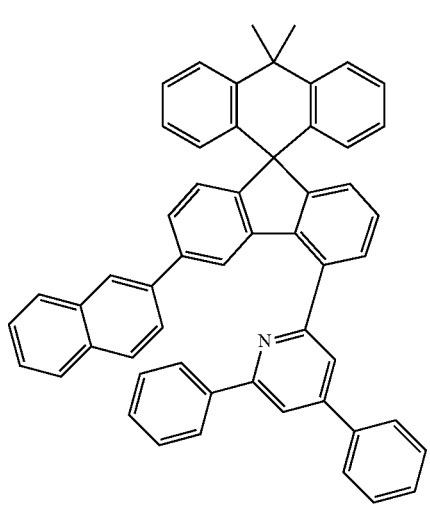
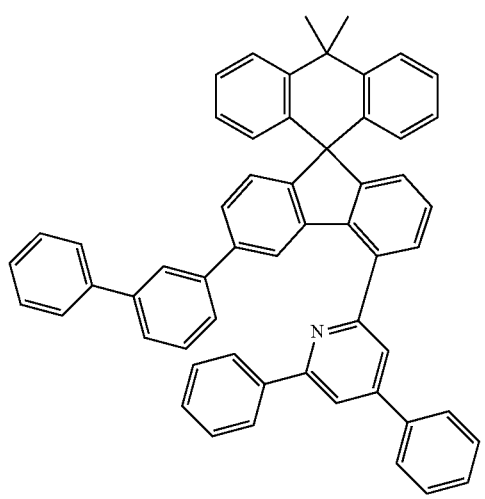
28
-continued
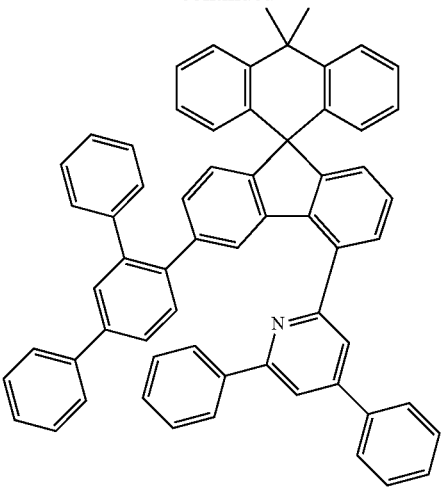
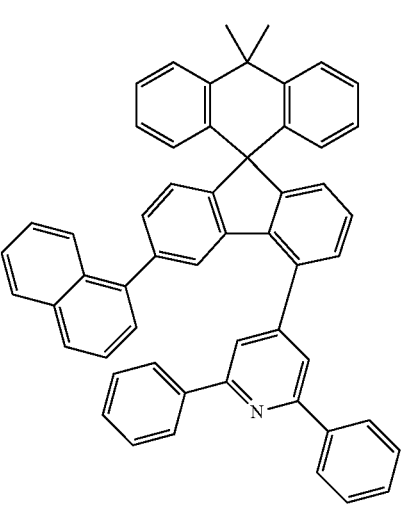
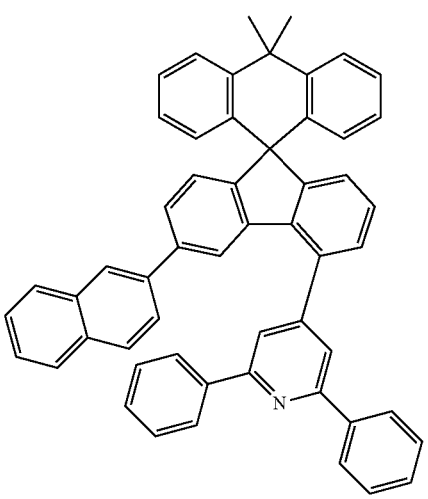

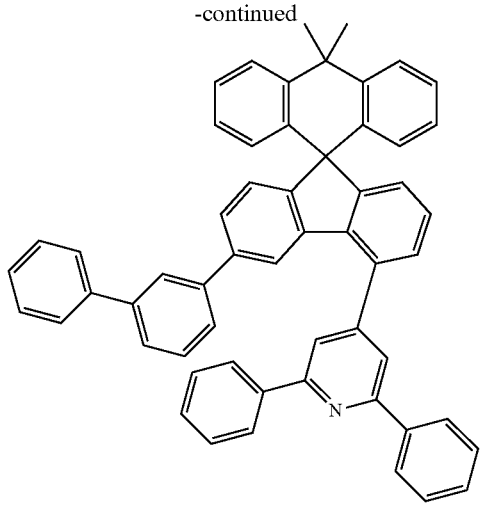
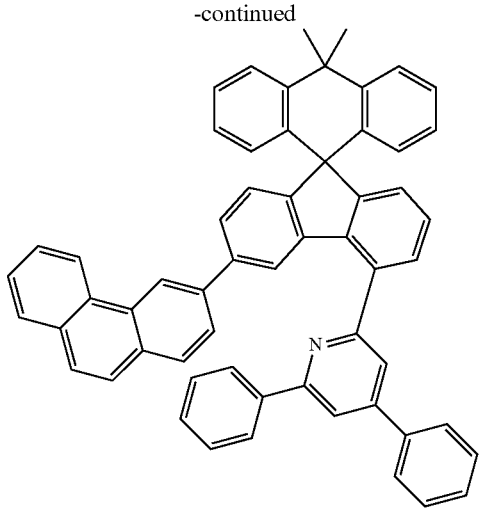
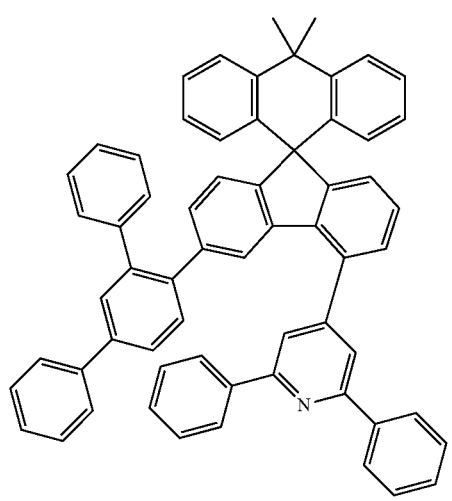
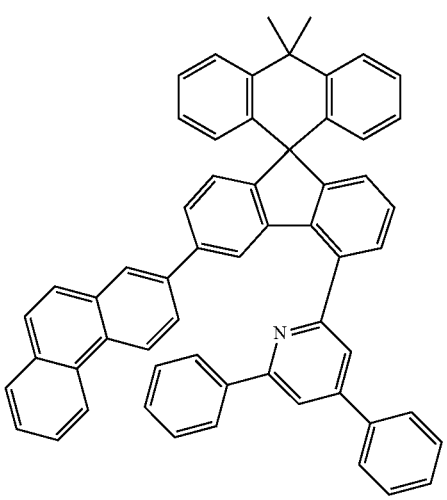
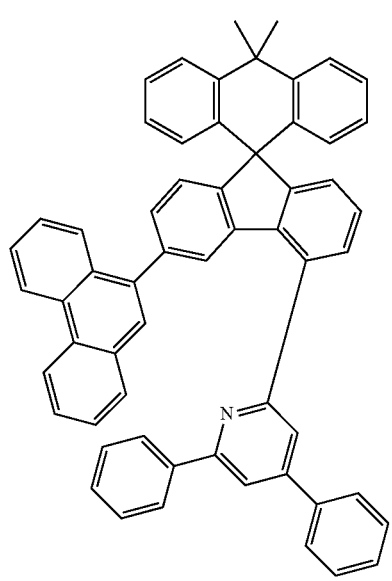
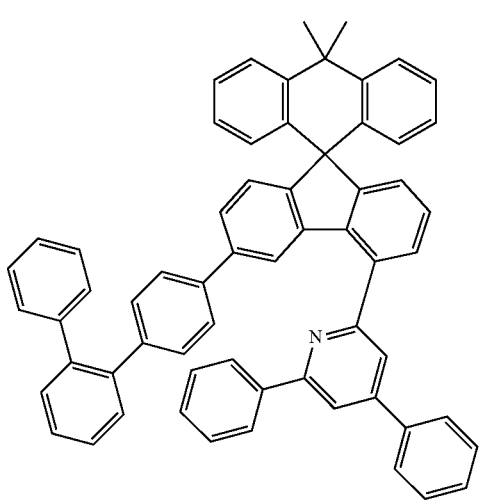

31
-continued
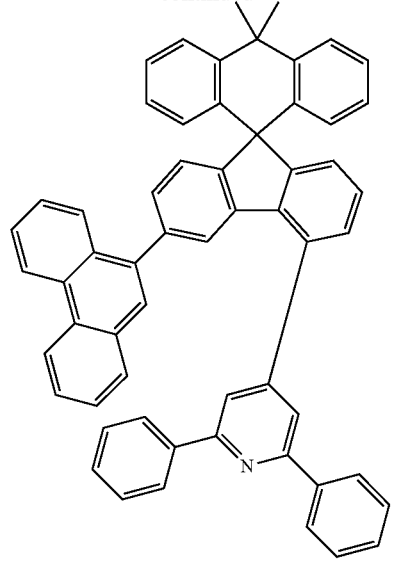
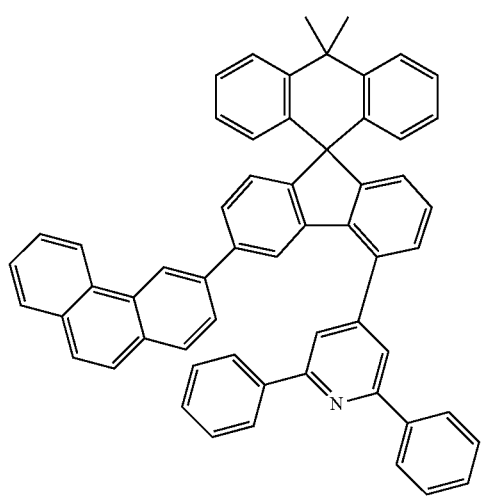
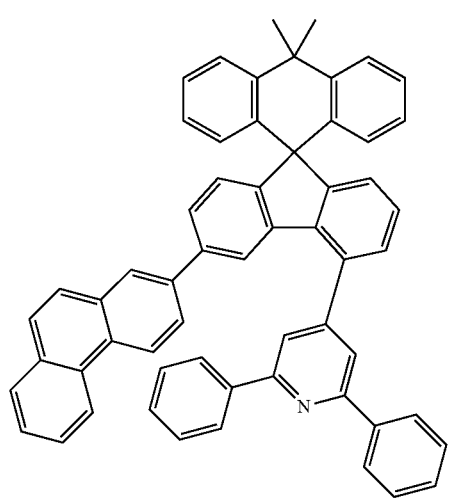
32
-continued
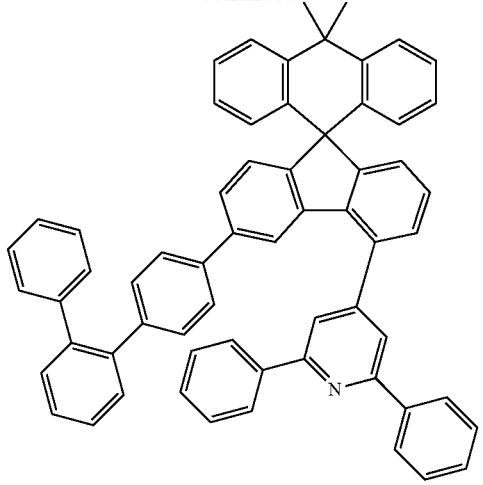
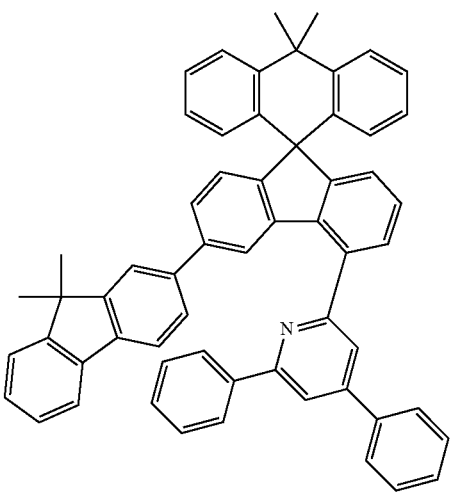
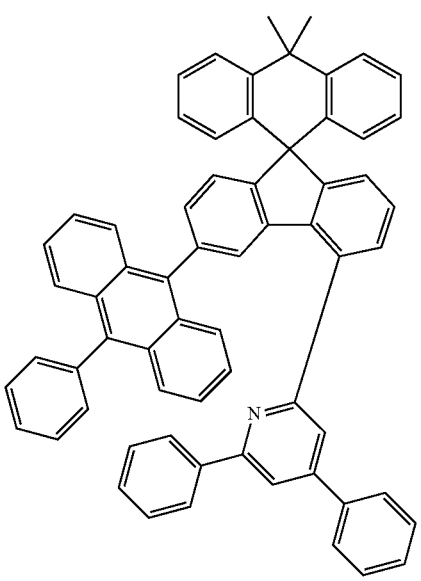

33
-continued
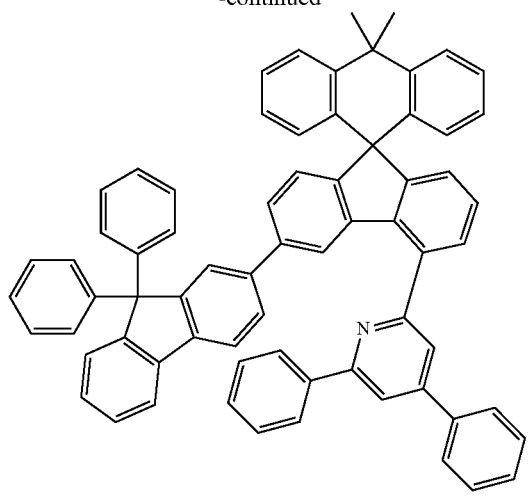
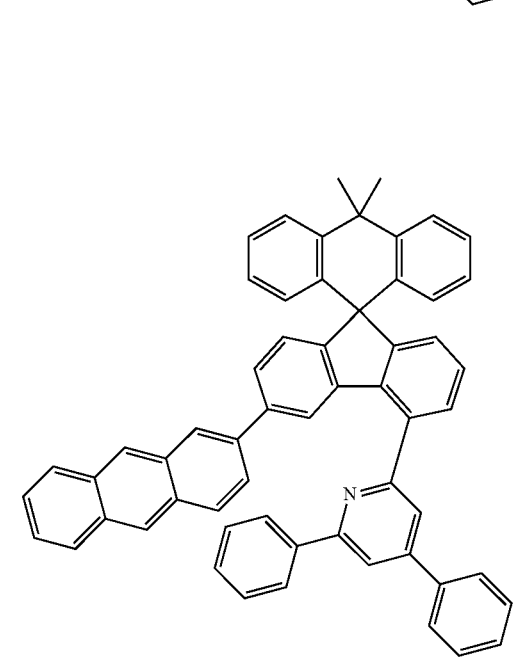
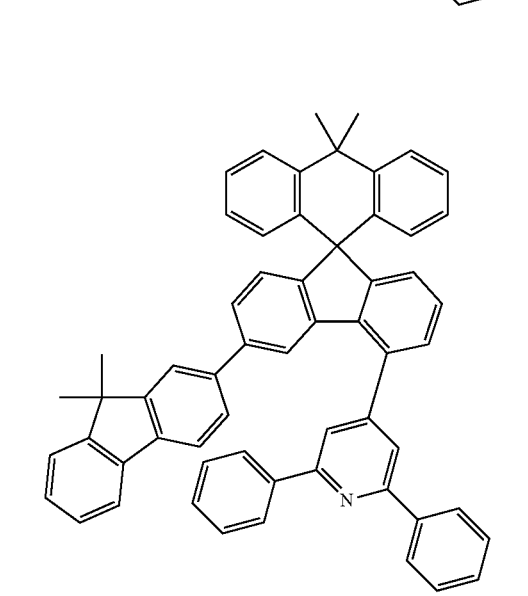
34
-continued
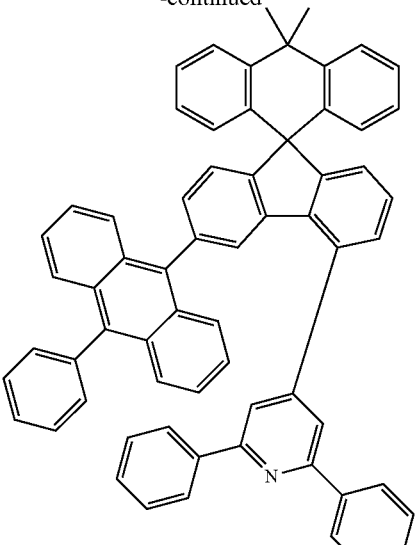
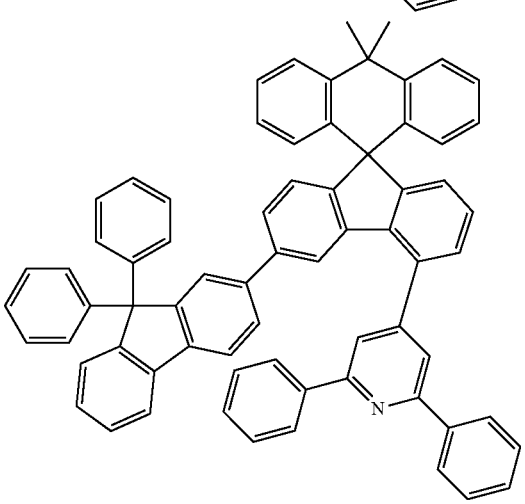
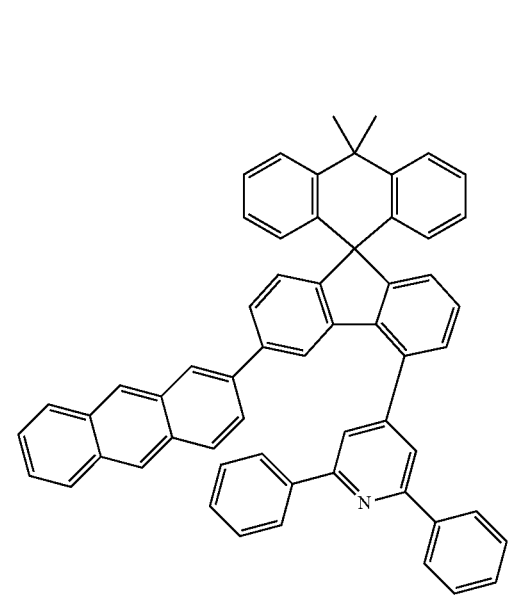

-continued
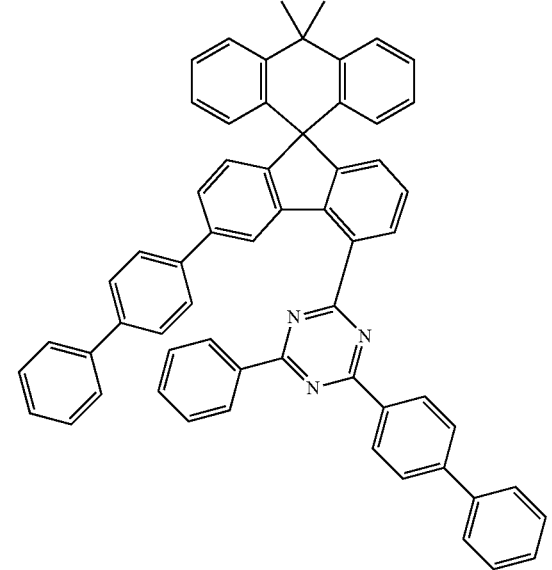
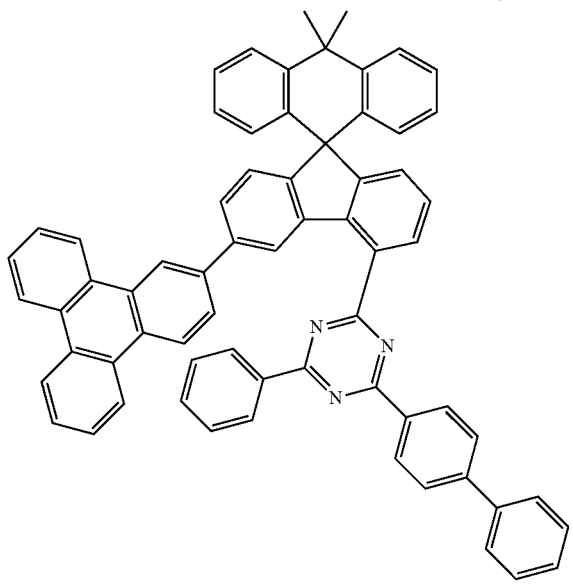
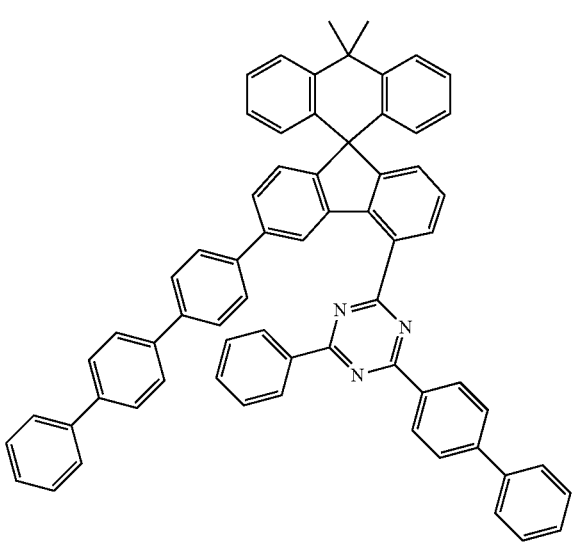
-continued
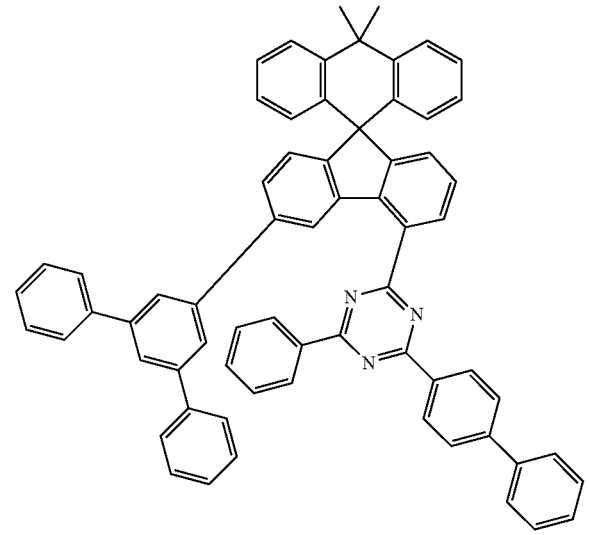
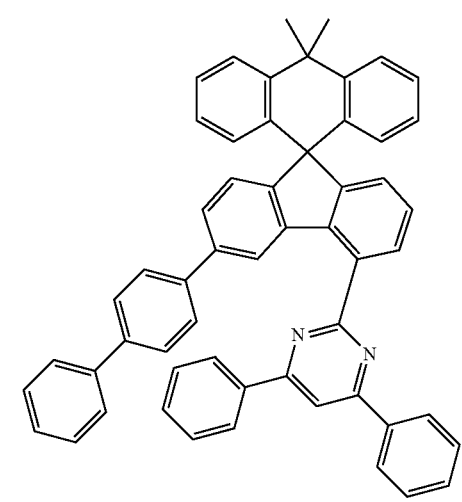
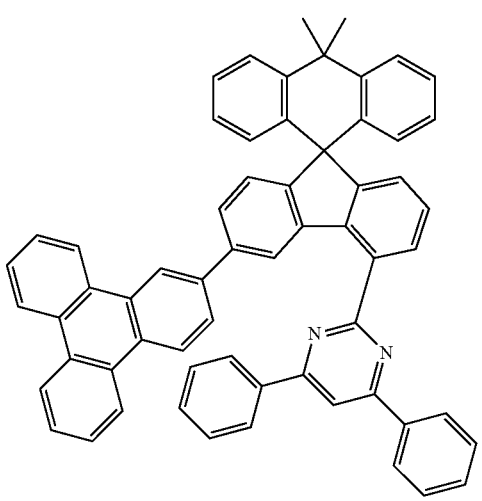

37
-continued
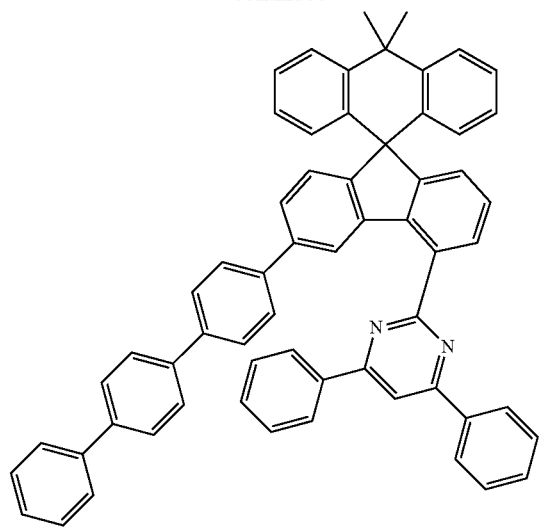
38
-continued
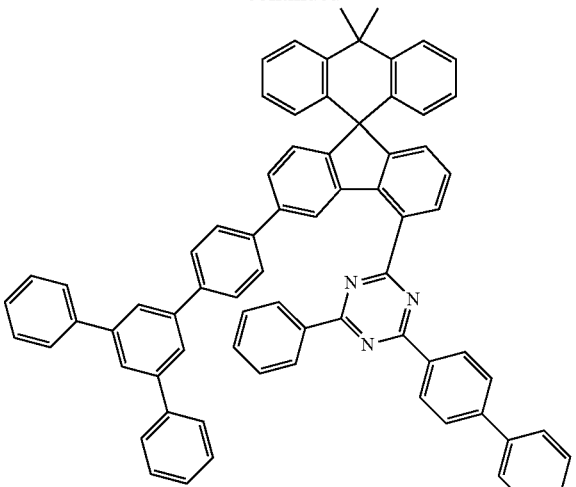
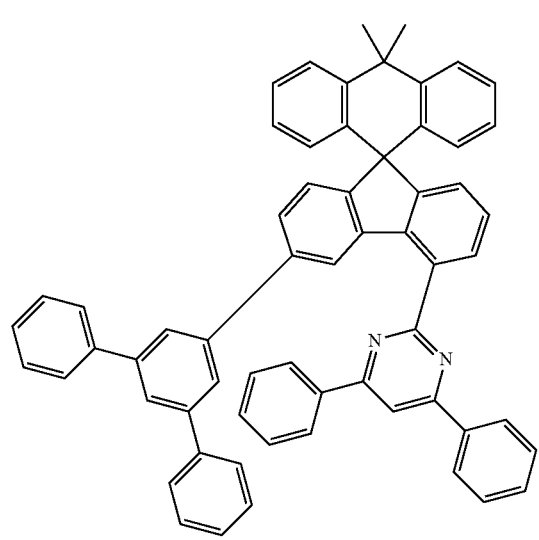
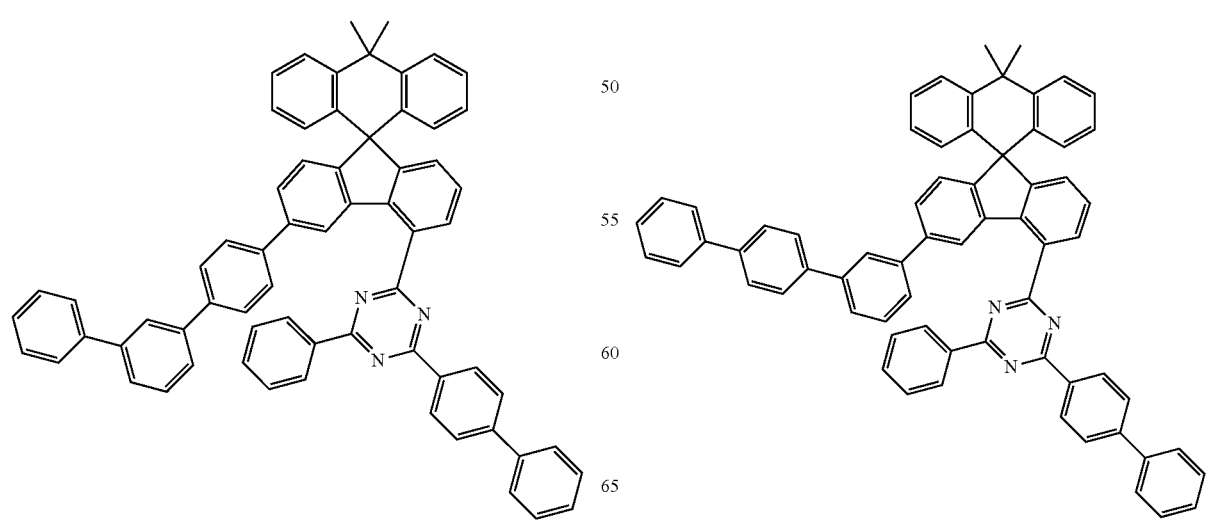

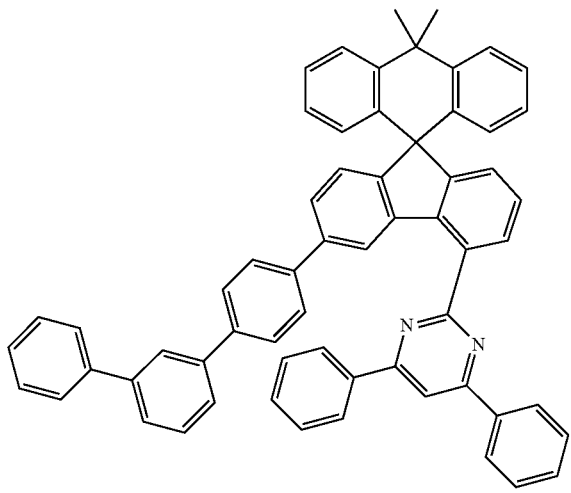
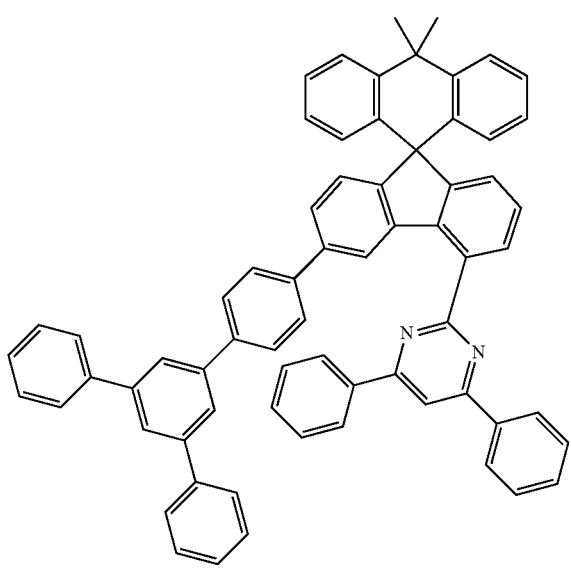
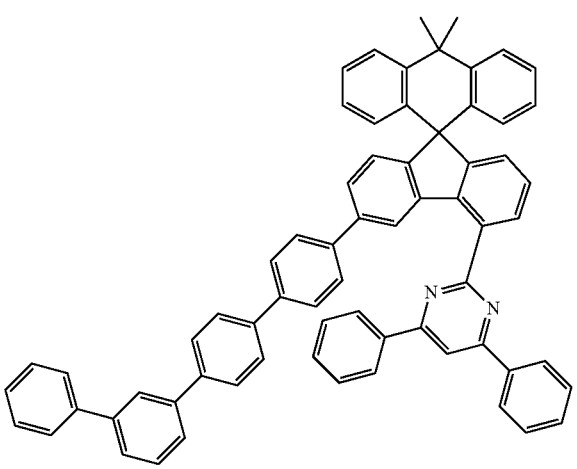
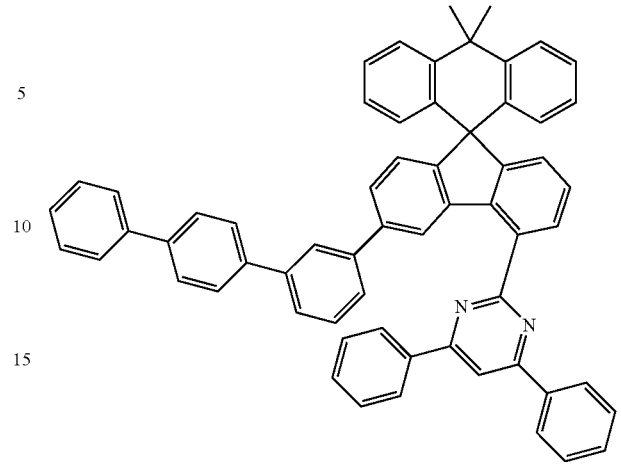
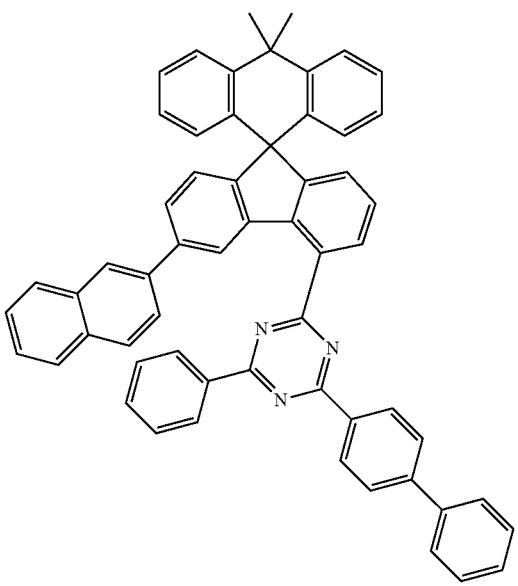

-continued
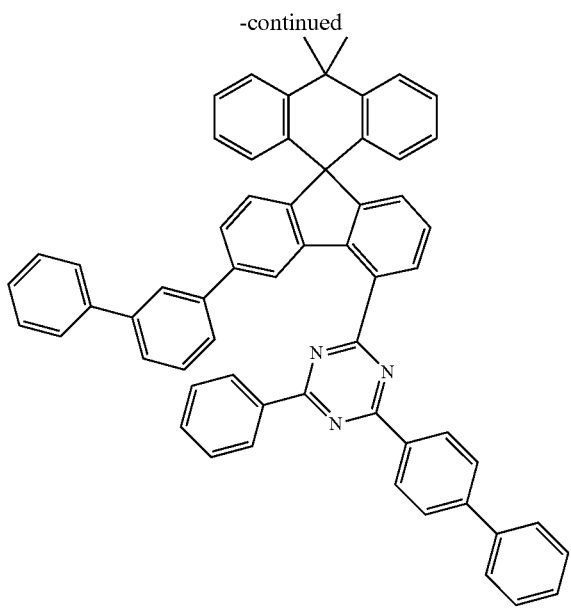
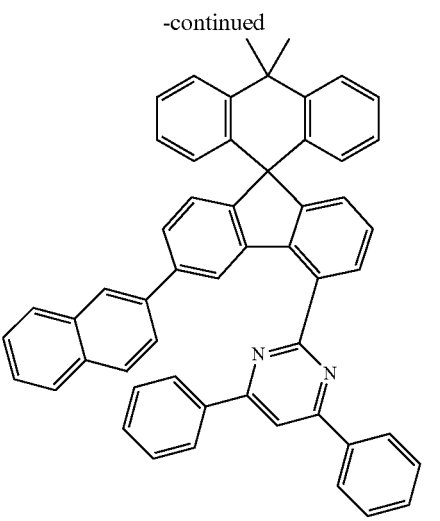
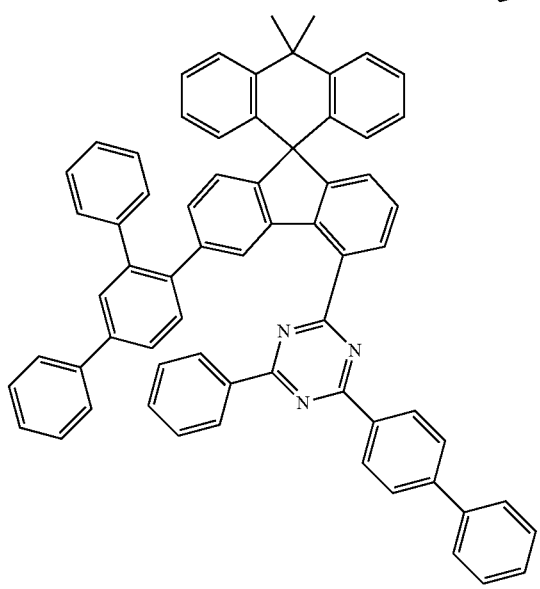
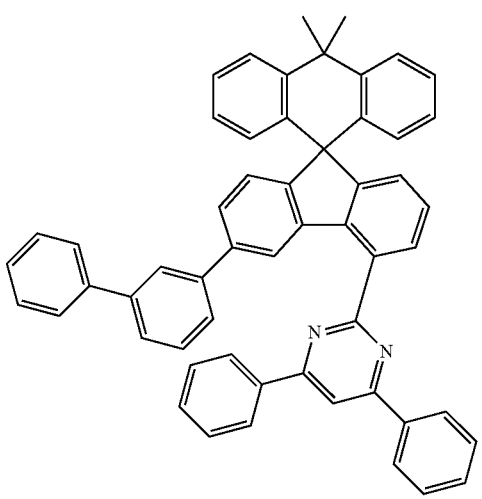
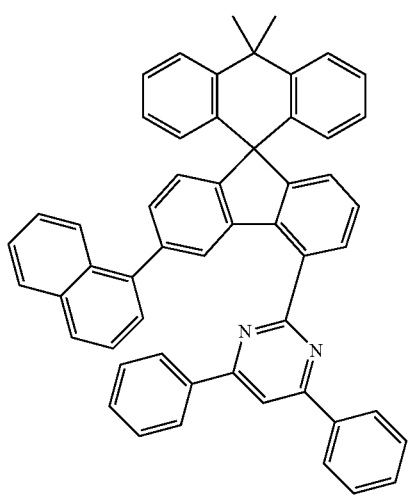
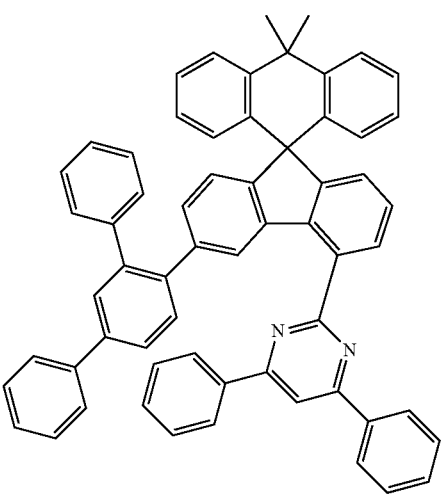

-continued
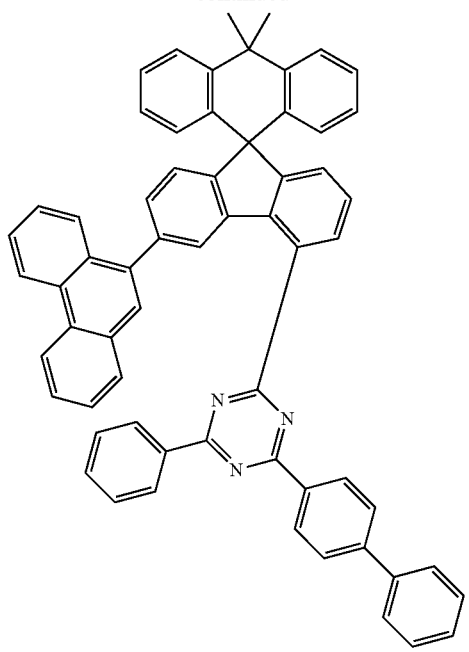
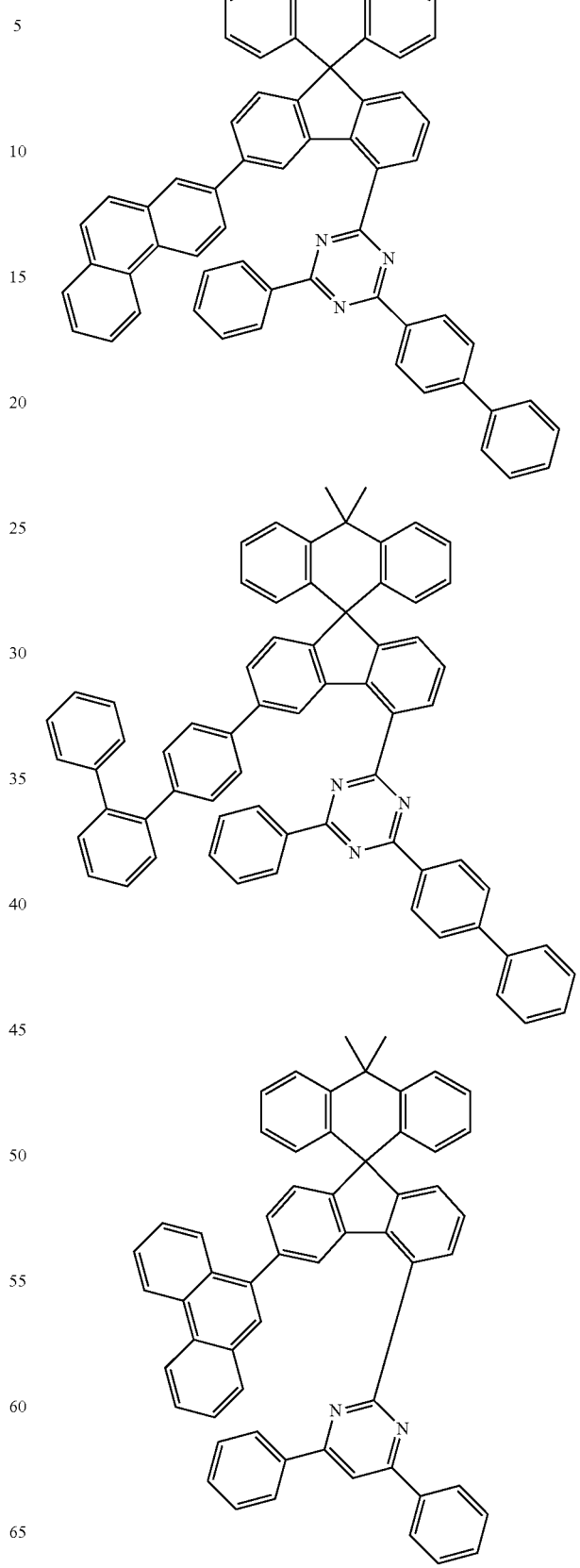
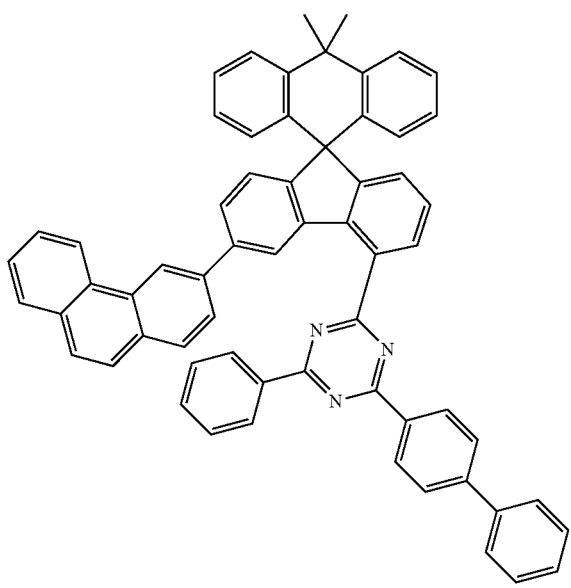

-continued
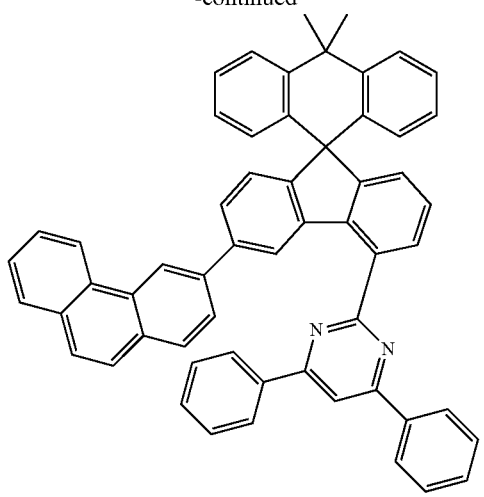
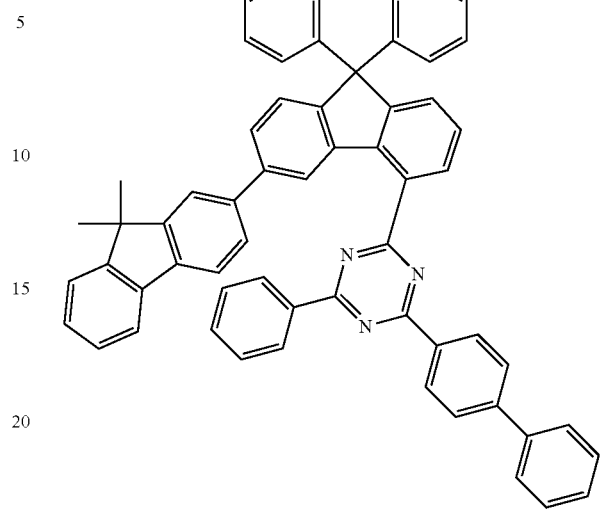
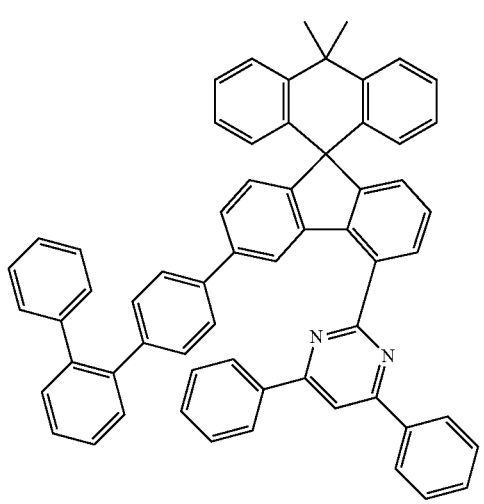
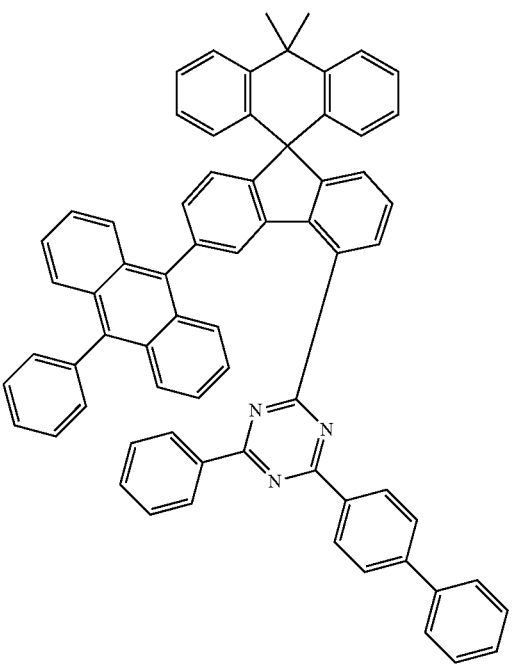

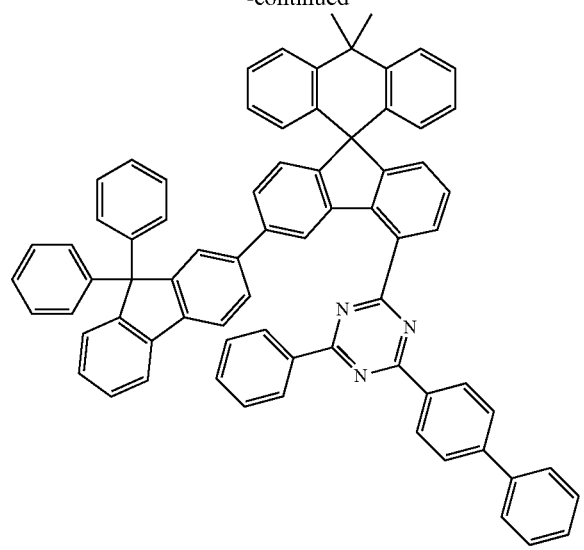
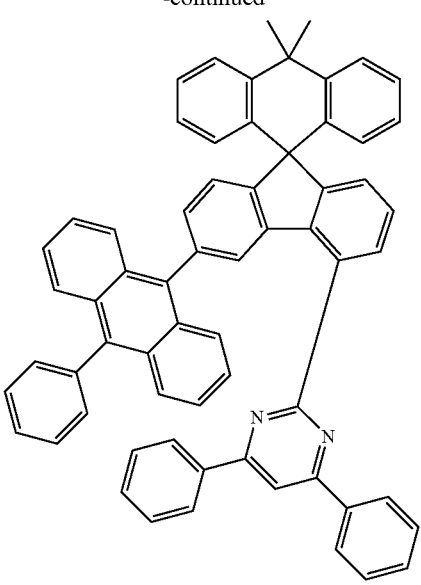
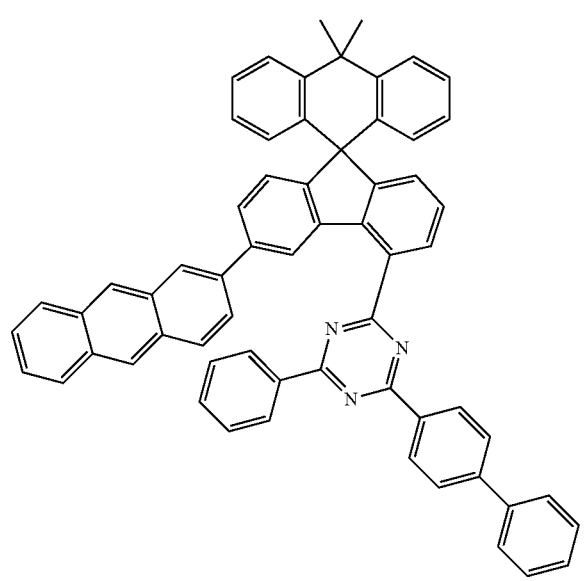
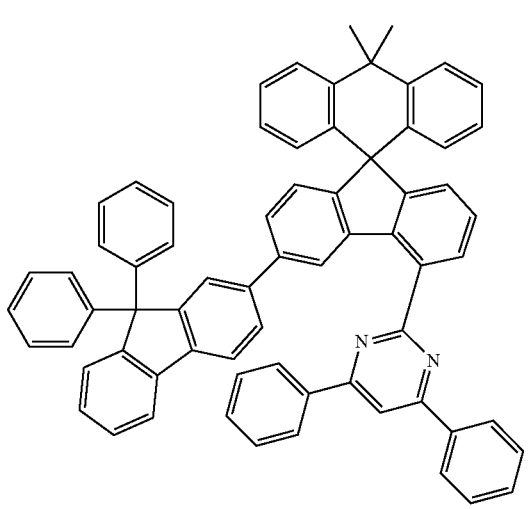
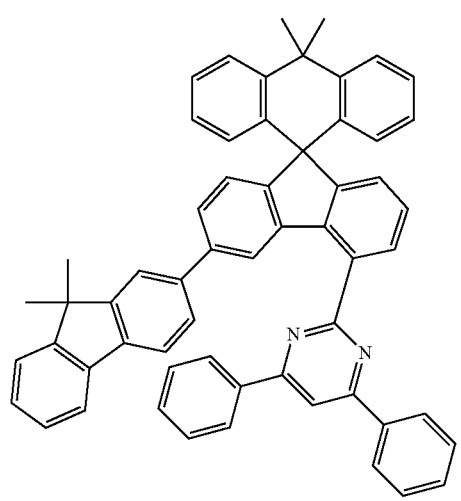
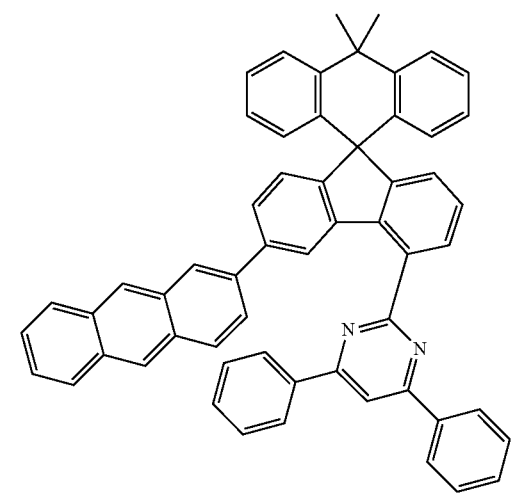

49
-continued
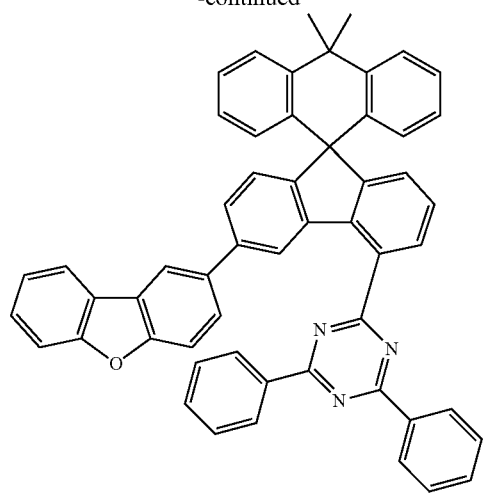
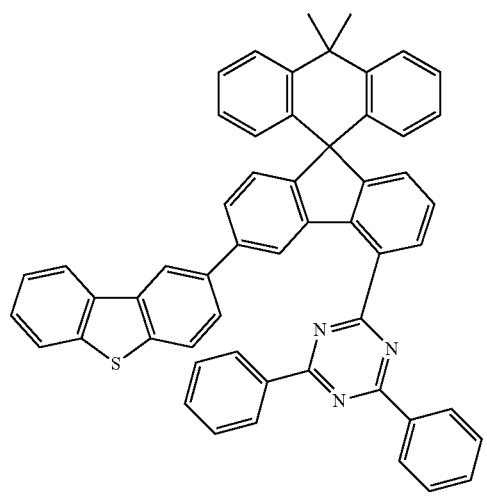
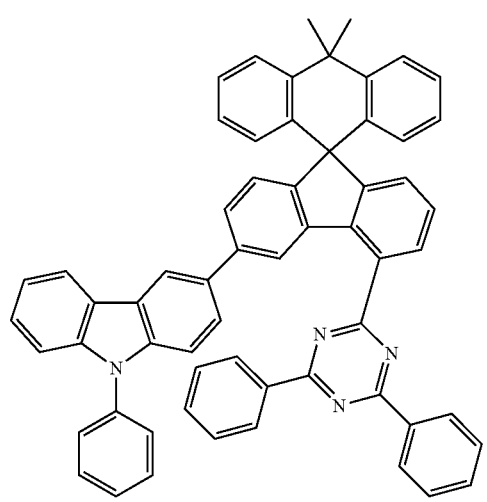
50
-continued
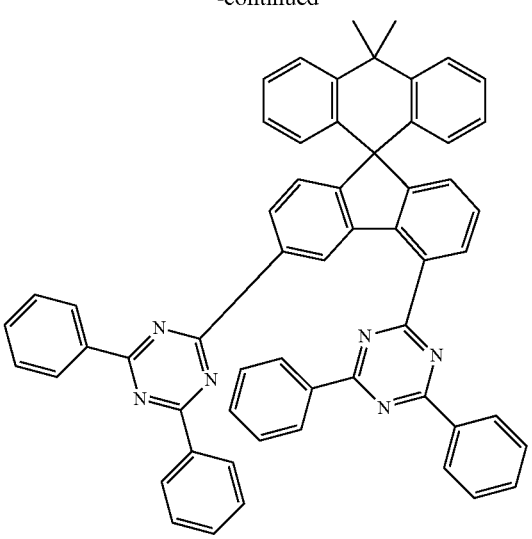
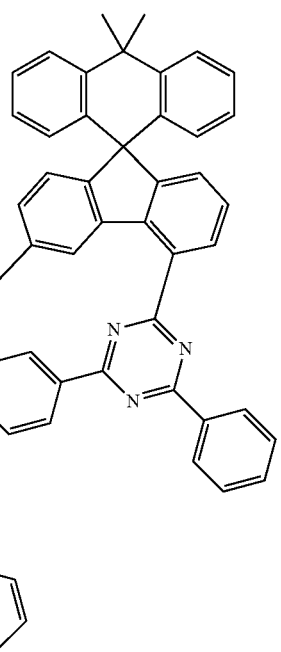

51
-continued
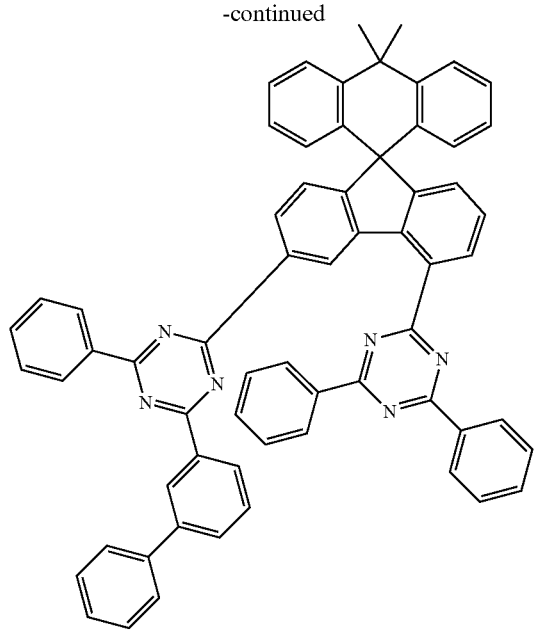
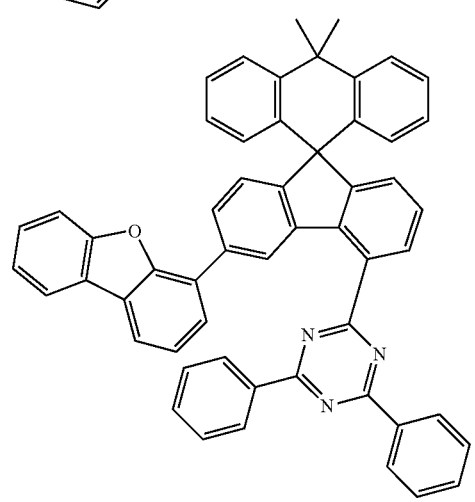
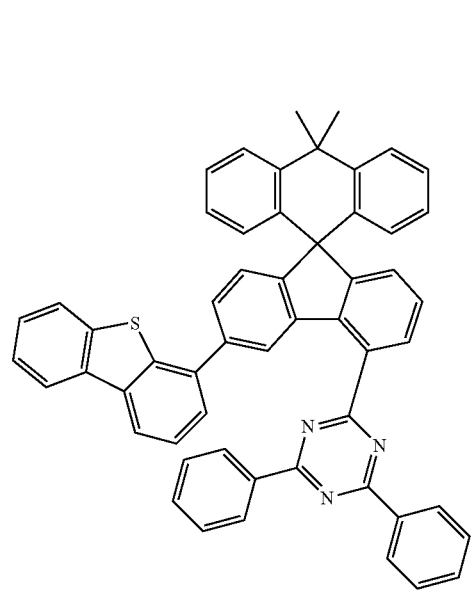
52
-continued
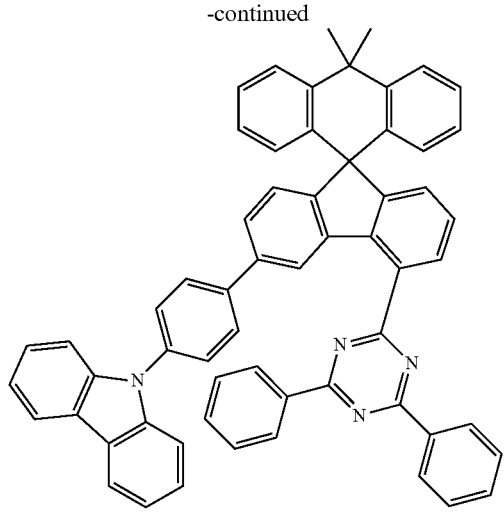
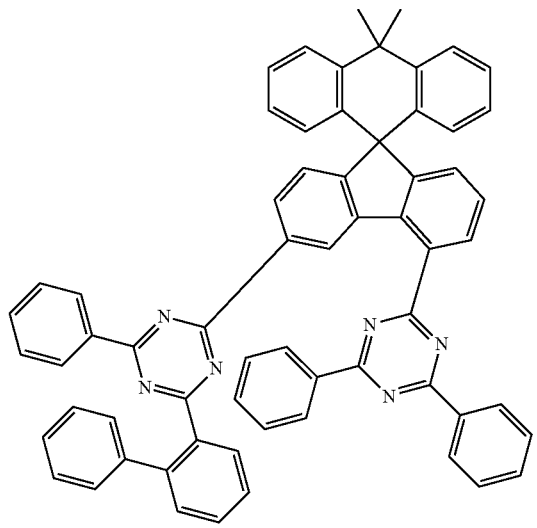

53
-continued
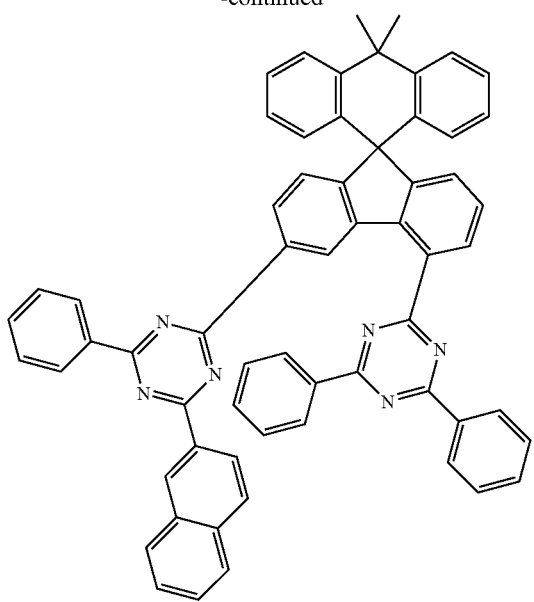
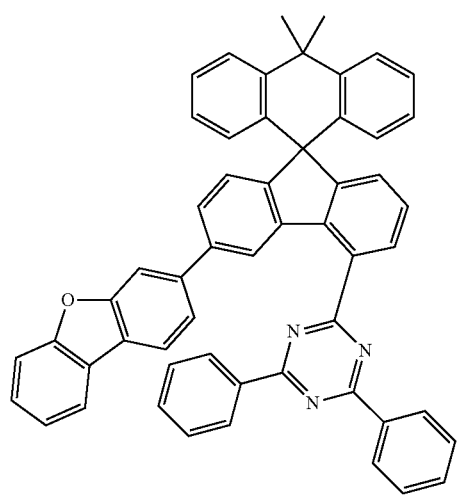
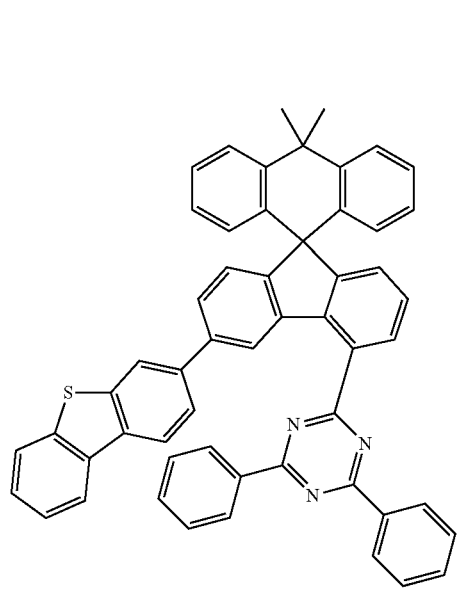
54
-continued
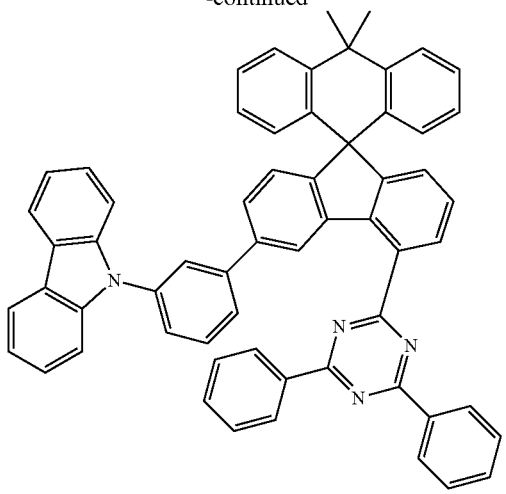
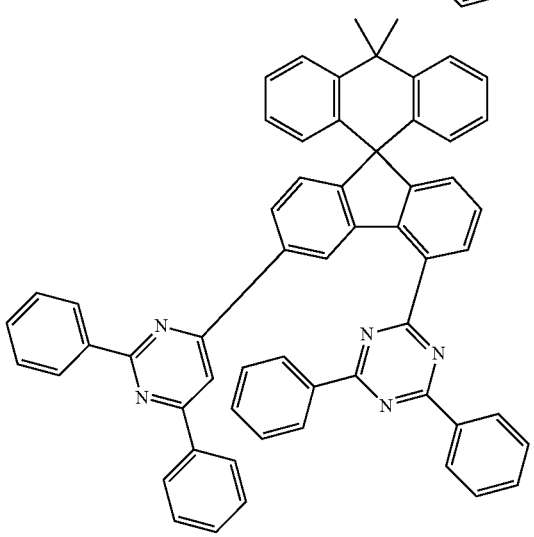
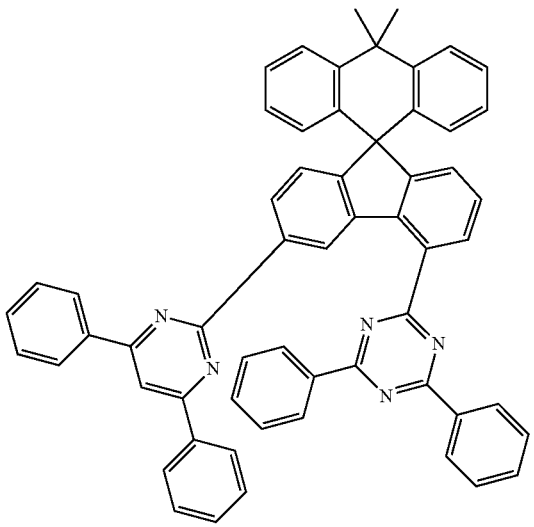

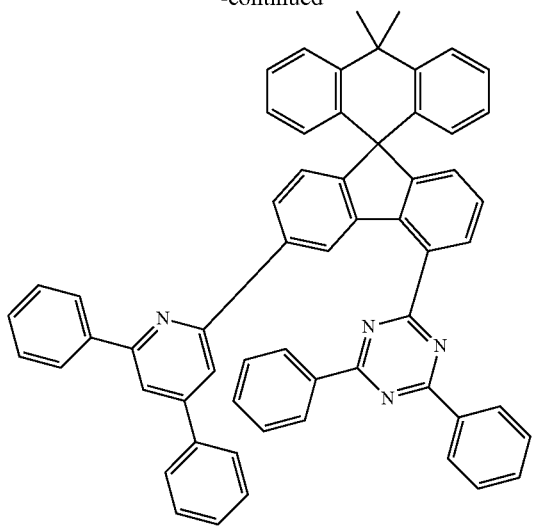
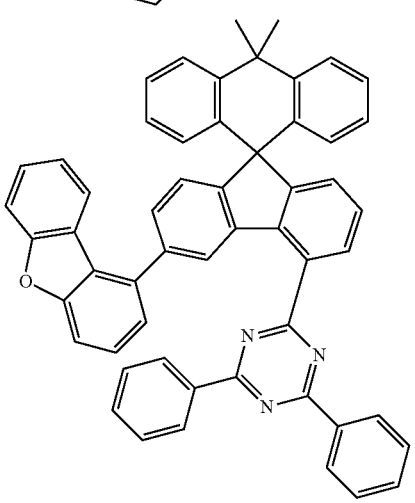
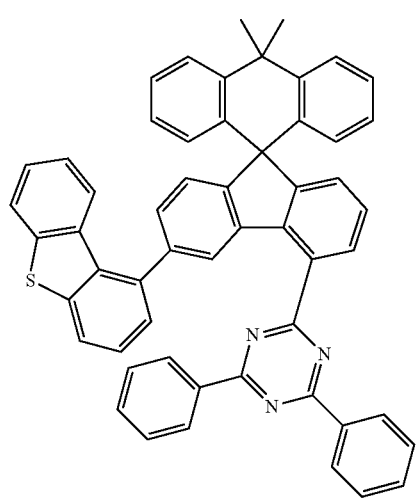
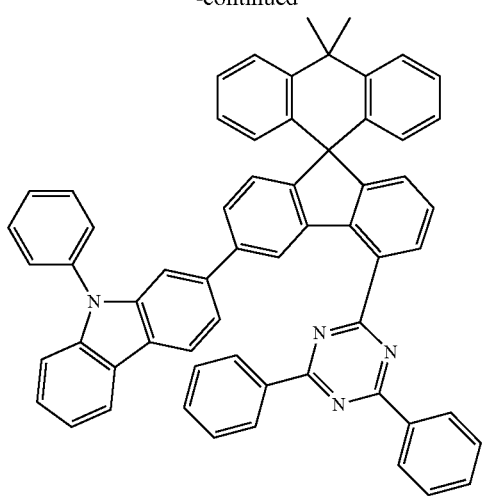
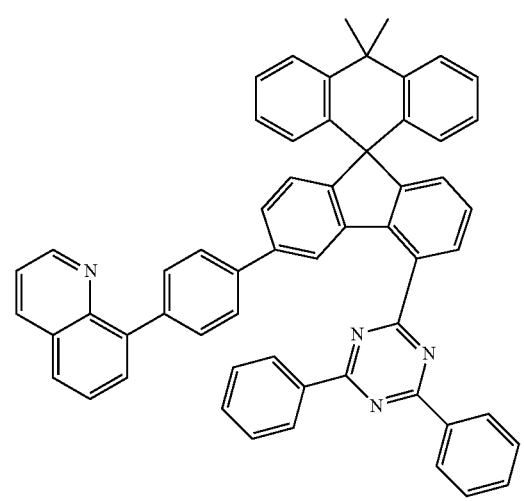

57
-continued
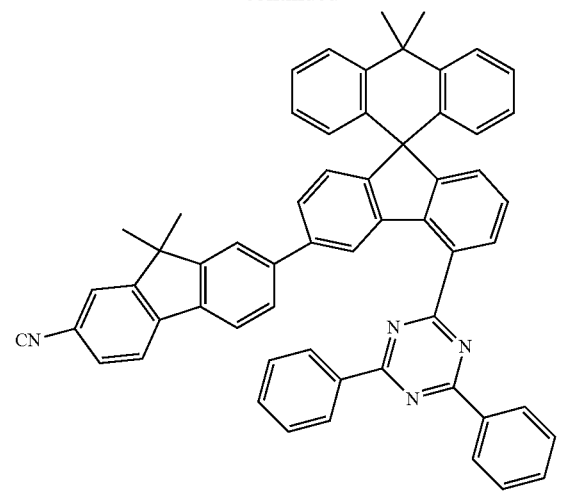
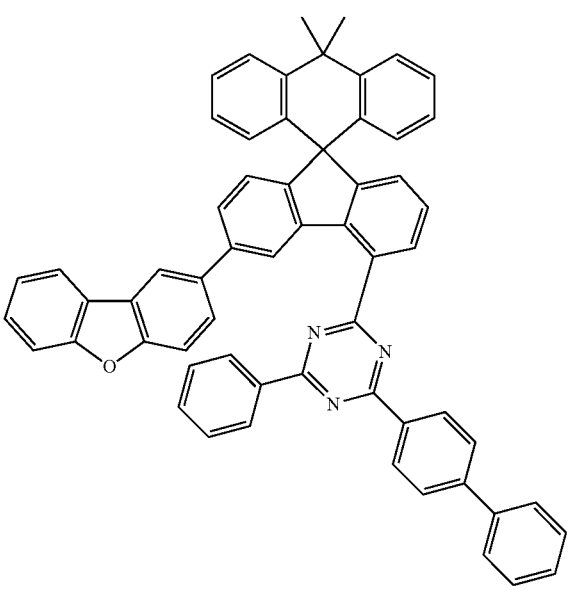
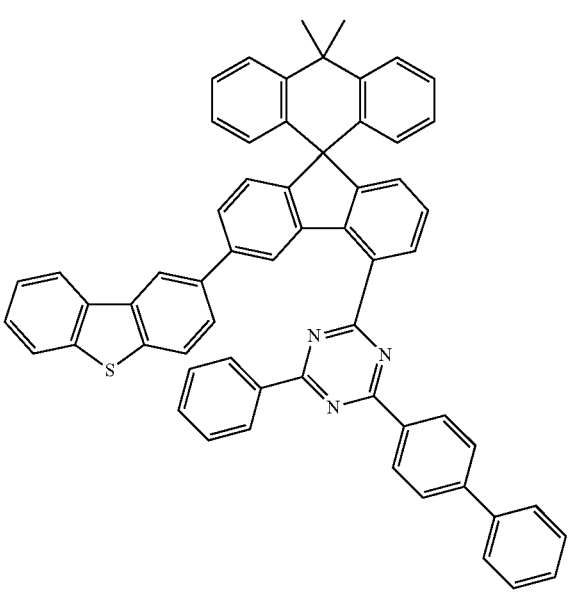
58
-continued
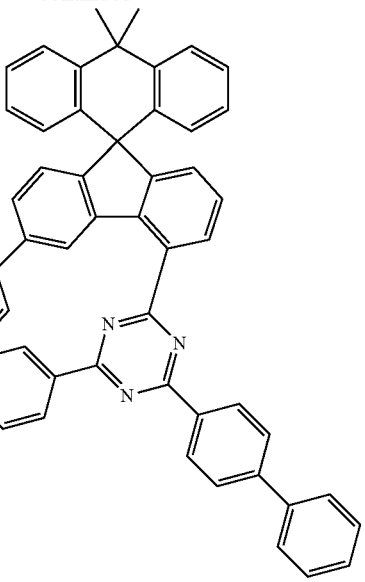
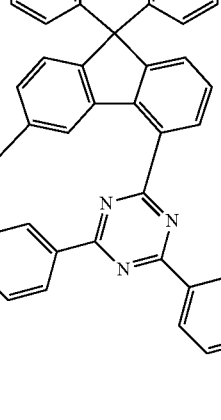
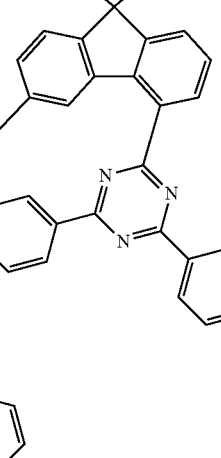

59
-continued
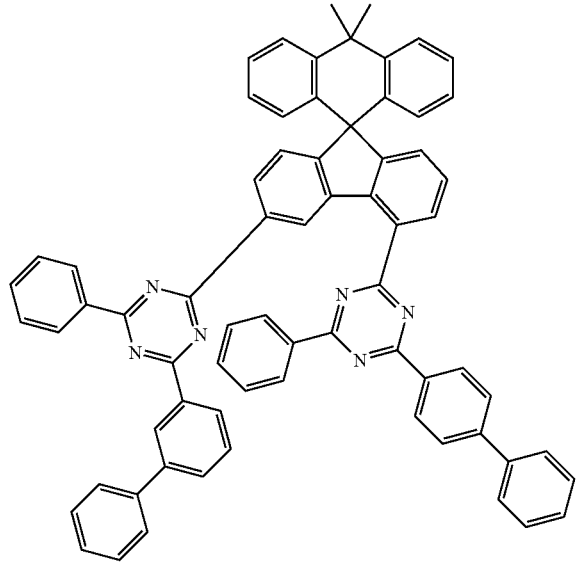
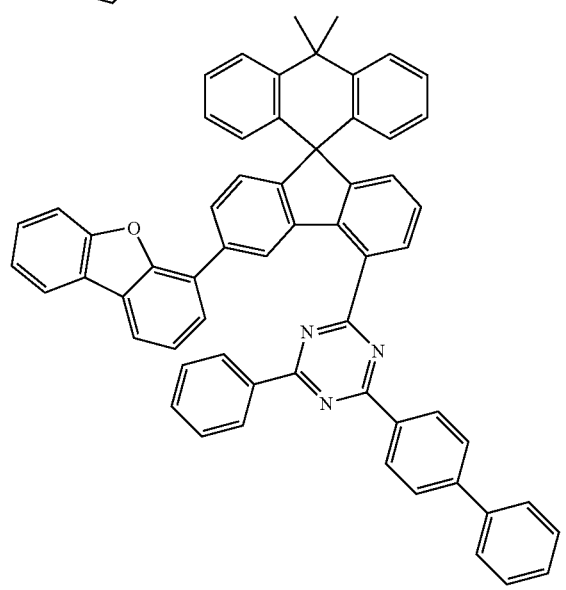
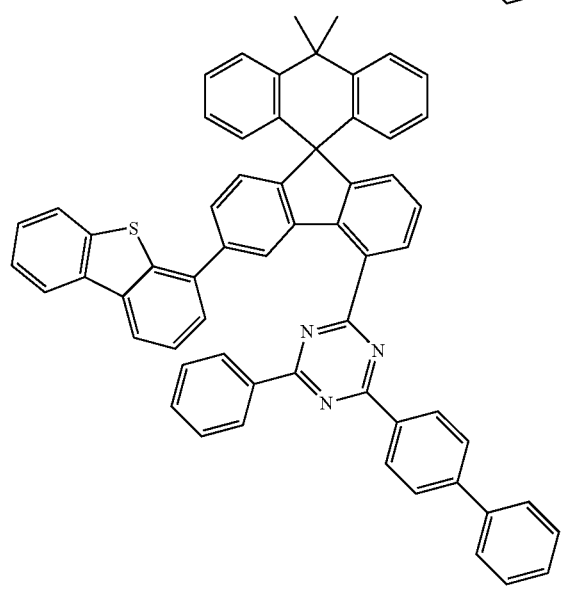
60
-continued
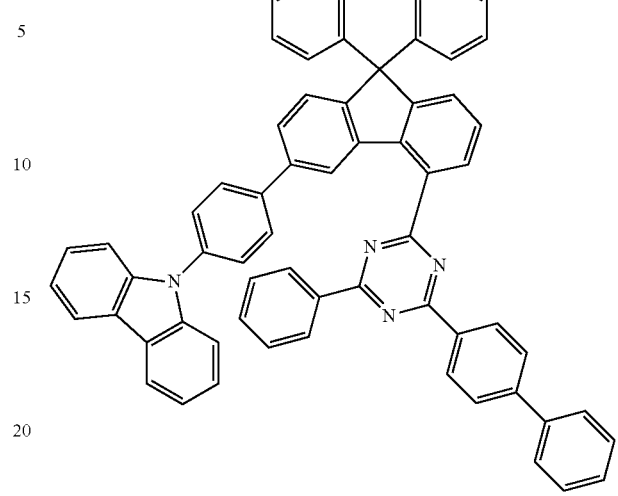
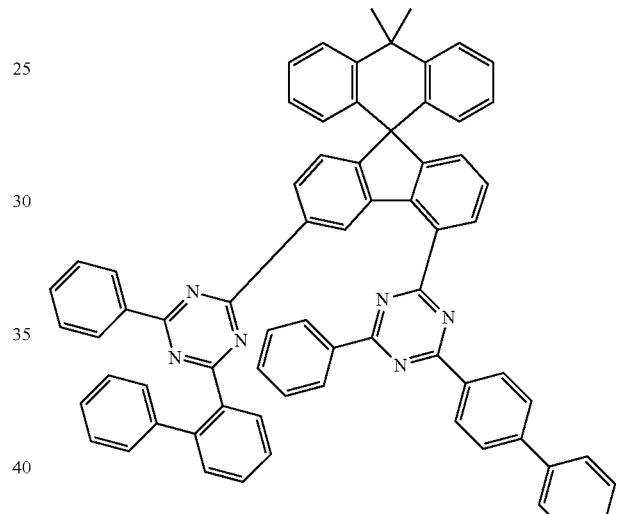
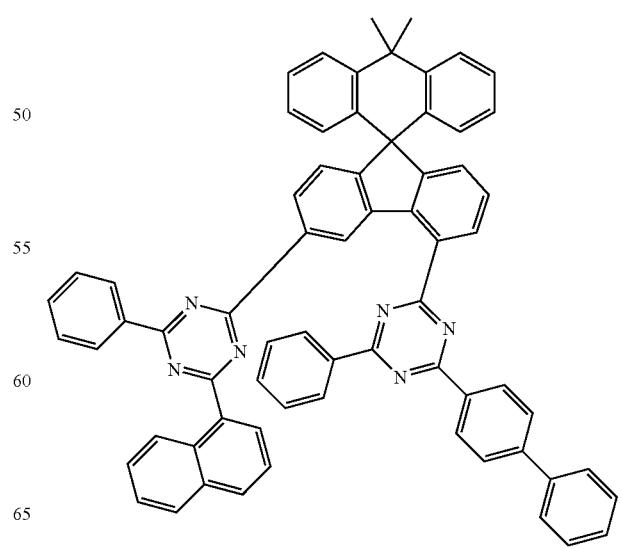

61
-continued
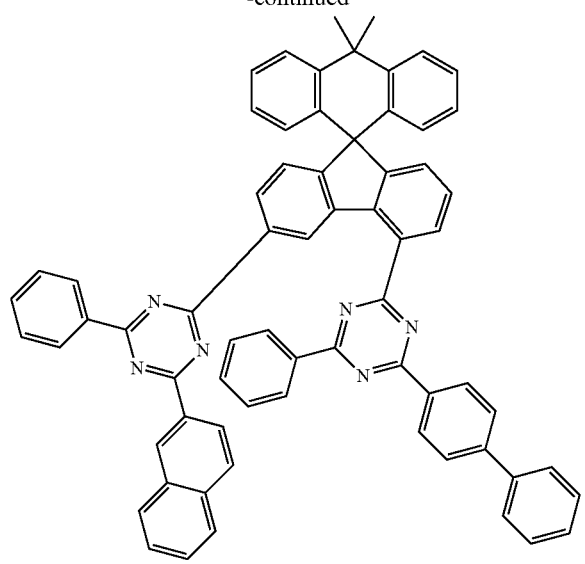
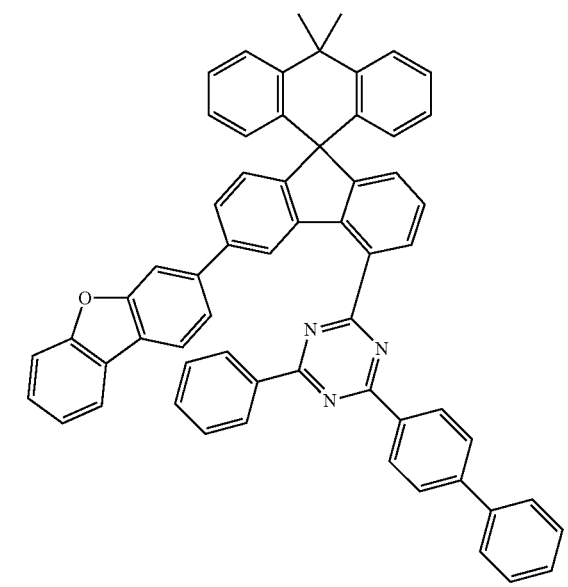
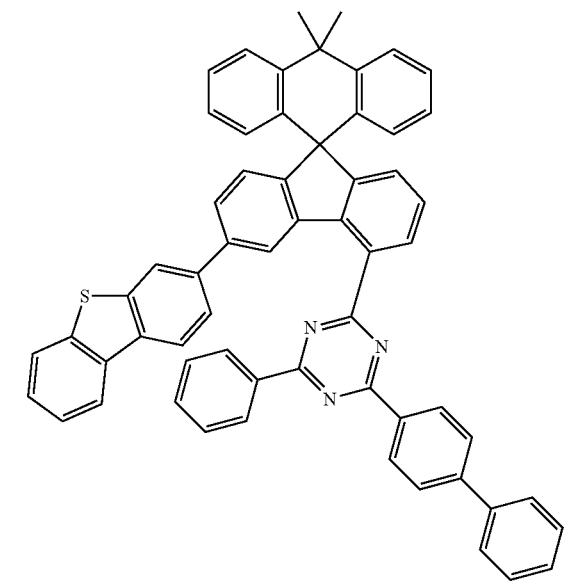
62
-continued
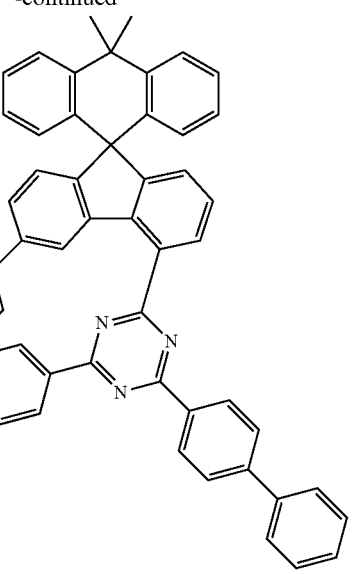
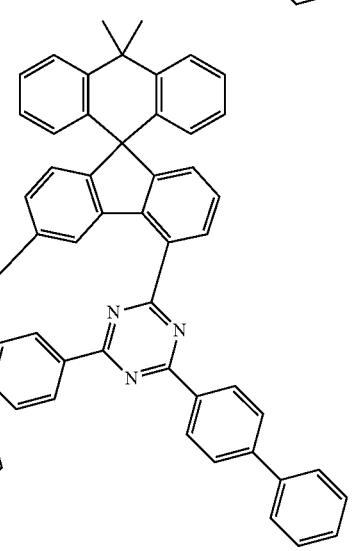
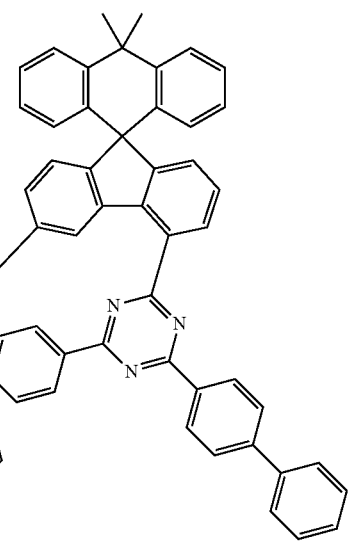

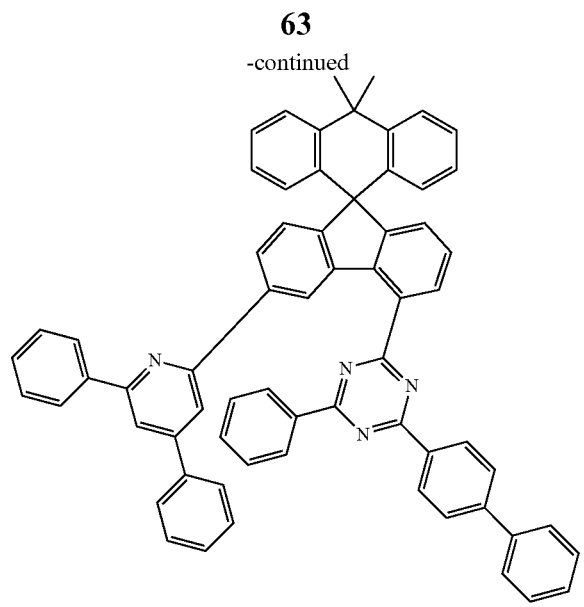
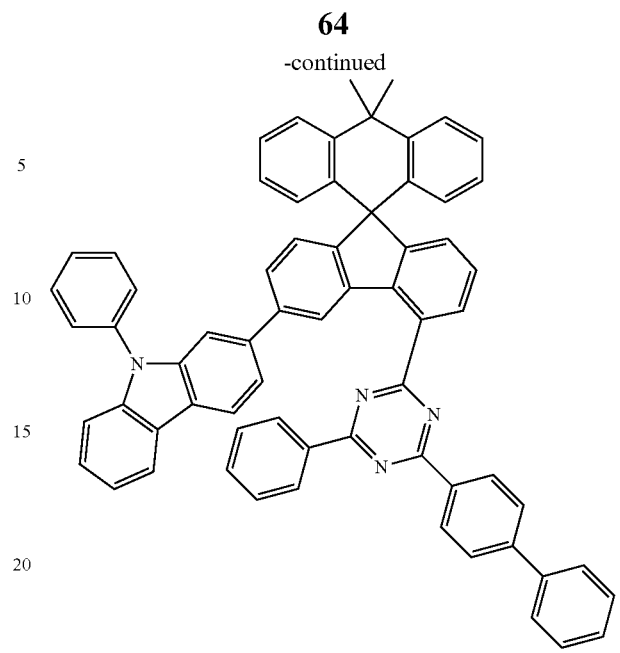
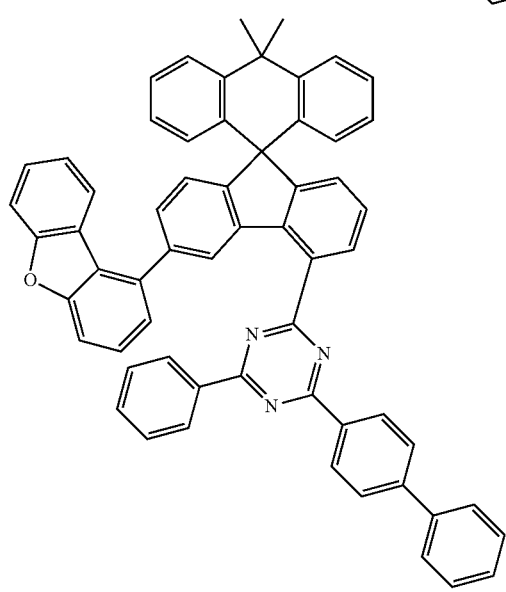
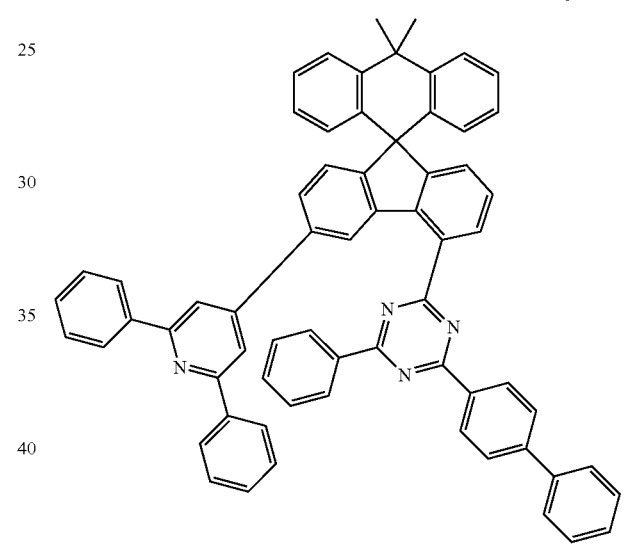
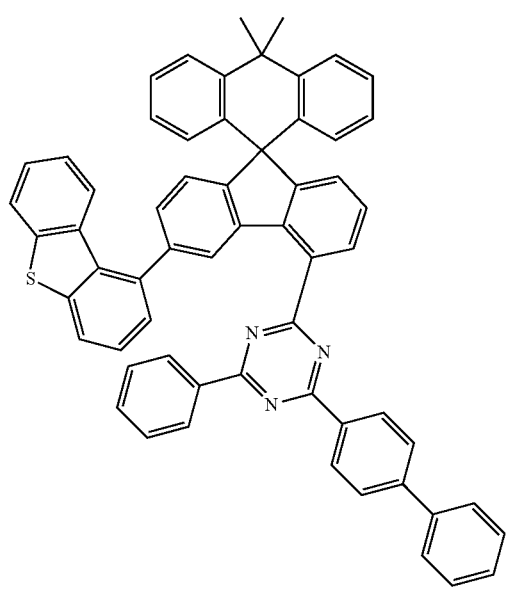
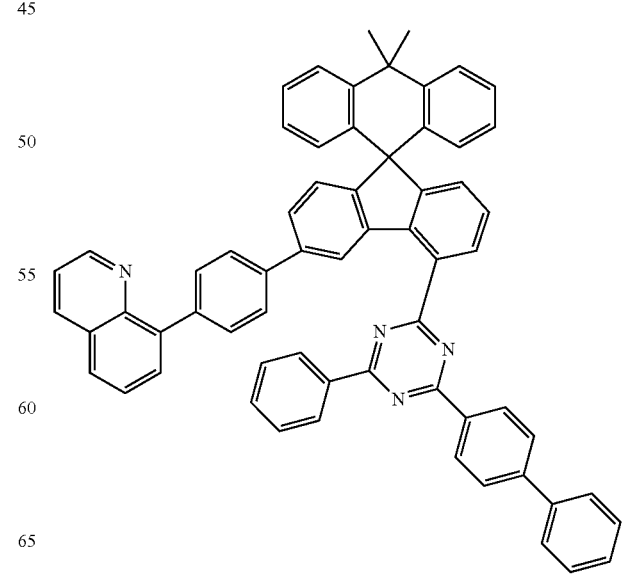

65
-continued
66
-continued
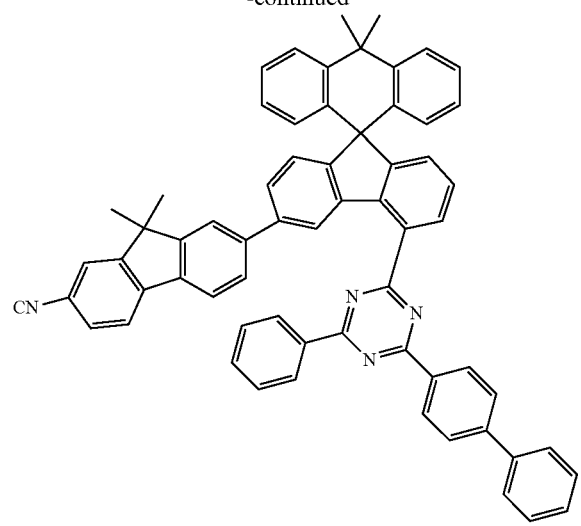
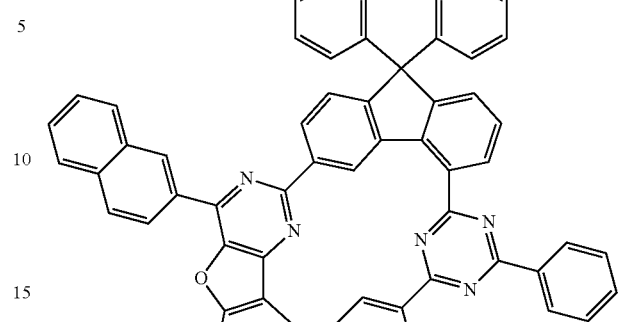
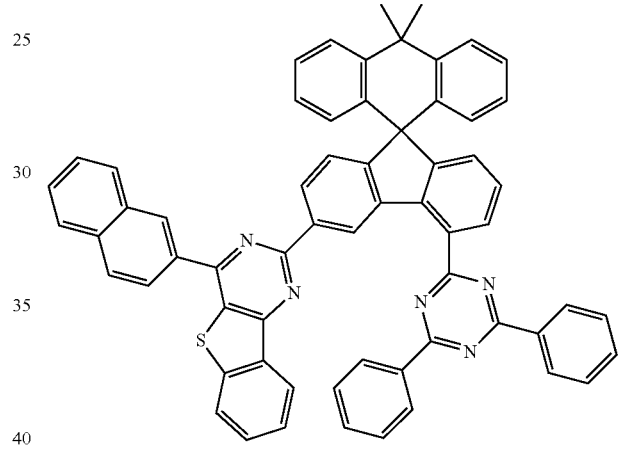
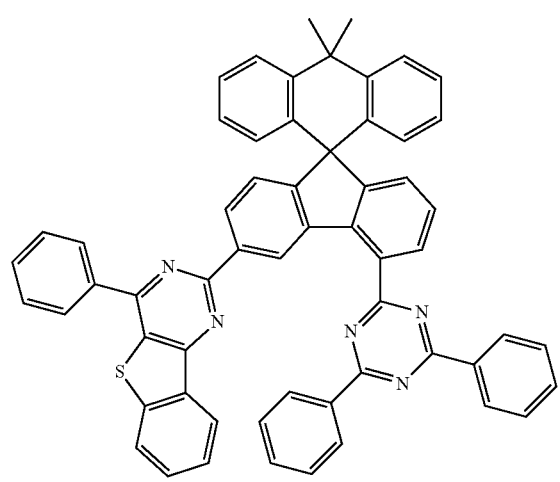

-continued
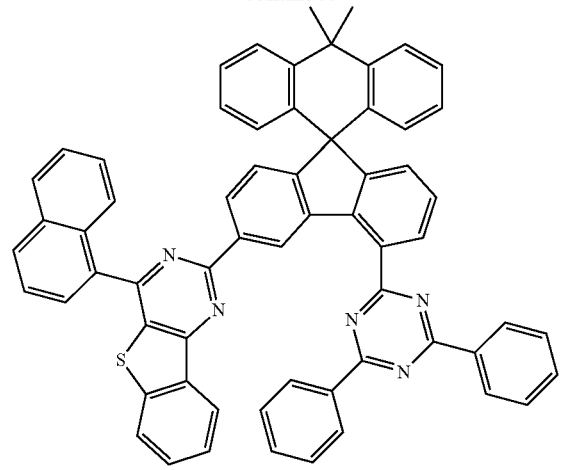
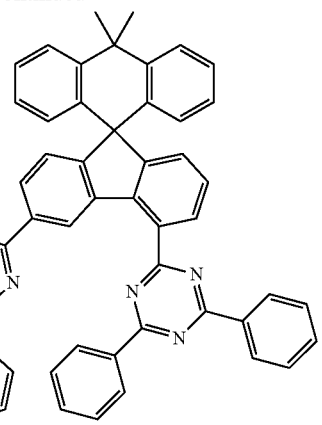
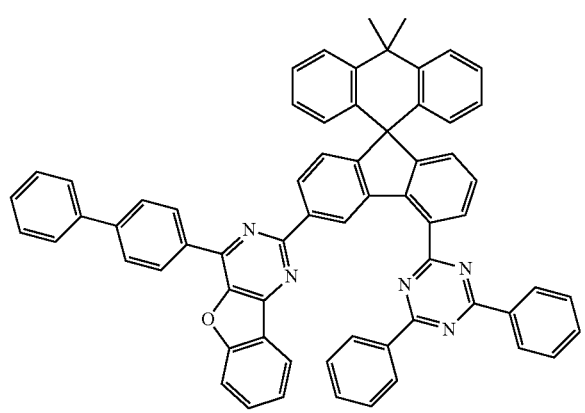
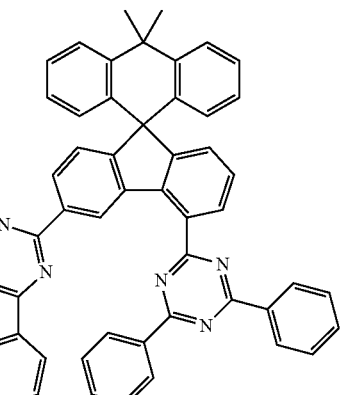
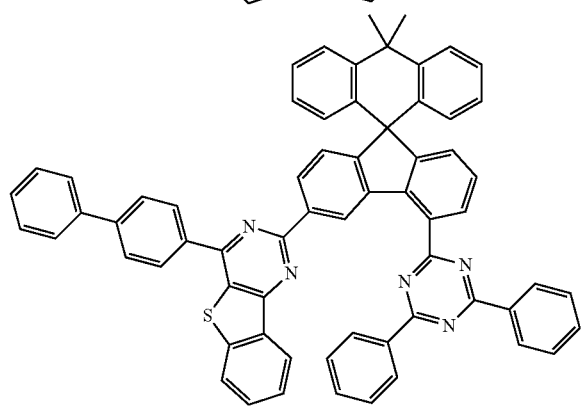
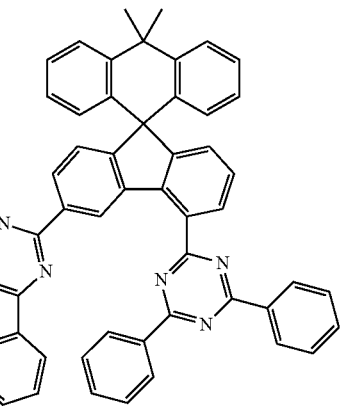
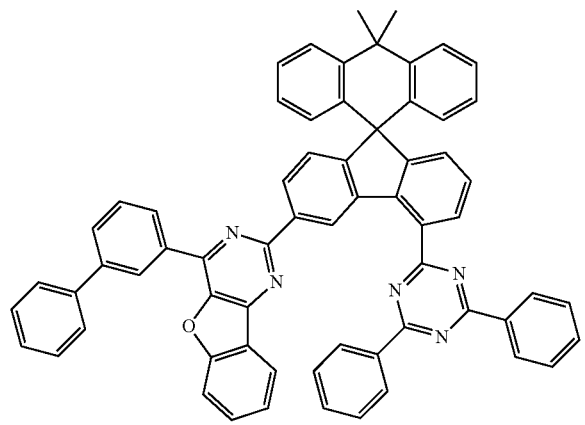
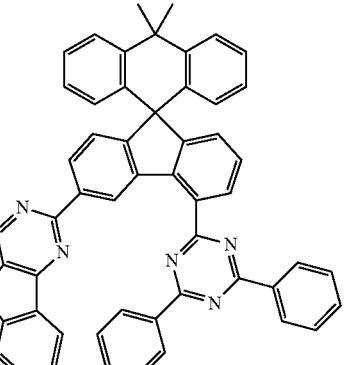

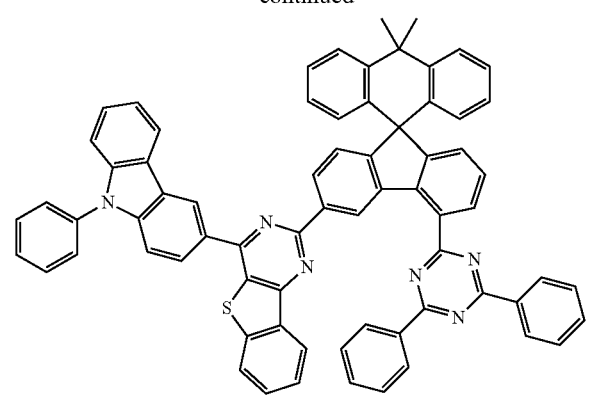
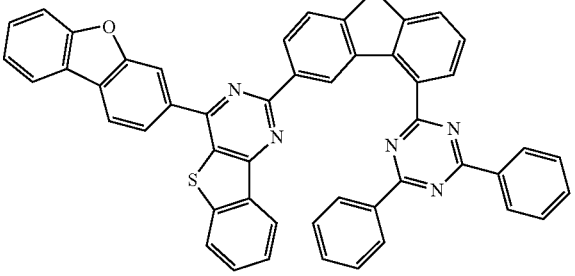
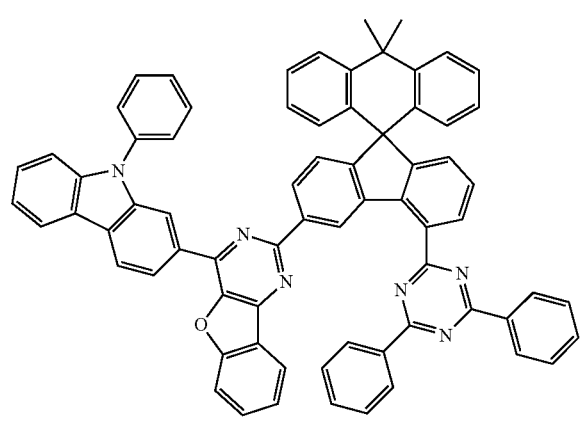
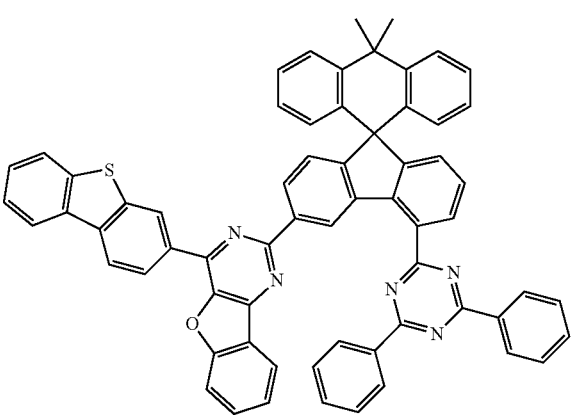
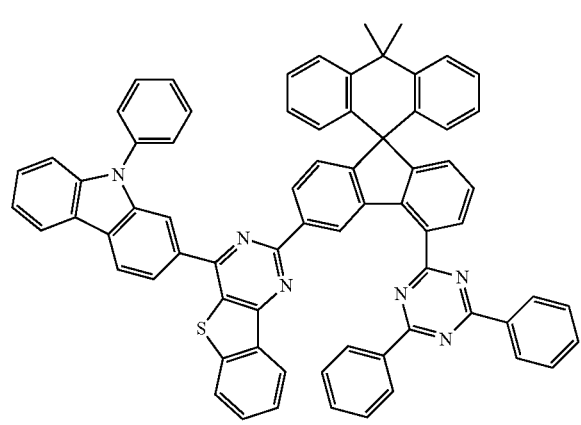
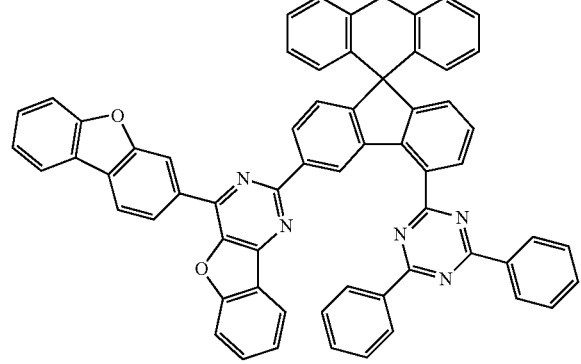
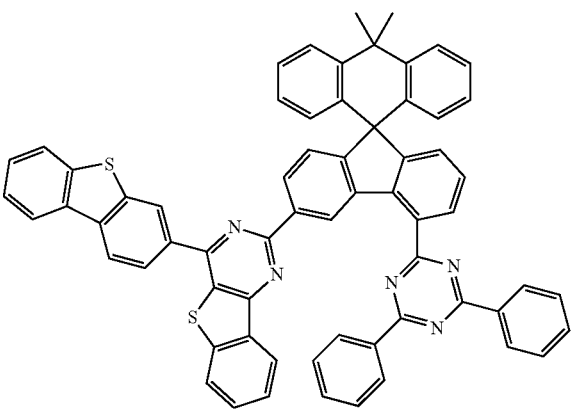
The compound represented by Chemical Formula 1 can be prepared, by a preparation method as shown in Reaction Scheme 1 below.

[Reaction Scheme 1]

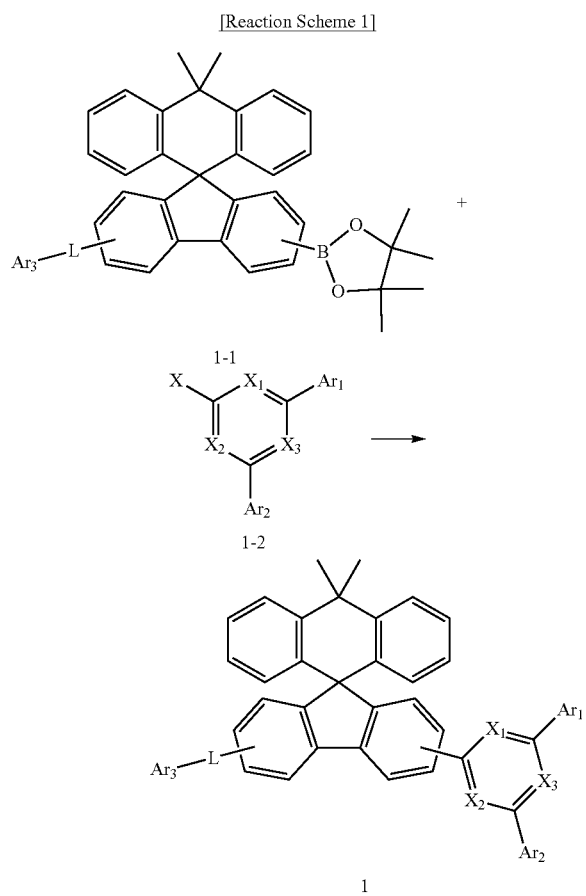

in Reaction Scheme 1, $X_1$, $X_2$, $X_3$, $Ar_1$, $Ar_2$, L, and $Ar_3$ are as defined above, and X is halogen. Preferably, X is chloro.

The above reaction scheme 1 is a Suzuki coupling reaction which is a reaction of preparing a compound represented by Chemical Formula 1 by reacting the compound represented by Chemical Formula 1-1 with the compound represented by Chemical Formula 1-2. The above preparation method can be further specified in the preparation examples described later.

In addition, the present disclosure provides an organic light emitting device comprising the compound represented by Chemical Formula 1. In one example, the present disclosure provides an organic light emitting device comprising a first electrode; a second electrode provided at a side opposite to the first electrode; and at least one layer of organic material layers provided between the first electrode and the second electrode, wherein the at least one layer of the organic material layers includes a compound represented by Chemical Formula 1.

The organic material layer of the organic light emitting device of the present disclosure may have a single layer structure, but it may have a multilayered structure in which two or more organic material layers are stacked. For example, the organic light emitting device of the present disclosure may have a structure comprising a hole injection layer, a hole transport layer, a light emitting layer, an electron transport layer, an electron injection layer and the like as the organic material layer. However, the structure of the organic light emitting device is not limited thereto, and it may include a smaller number of organic layers.

Further, the organic material layer may include a hole injection layer, a hole transport layer, or a layer simultaneously injecting and transporting holes, wherein the hole injection layer, the hole transport layer, and a layer simultaneously injecting and transporting holes include a compound represented by Chemical Formula 1.

Further, the organic material layer may include a light emitting layer, and the light emitting layer includes a compound represented by Chemical Formula 1.

Further, the organic material layer may include an electron transport layer or an electron injection layer, wherein the electron transport layer or the electron injection layer include a compound represented by Chemical Formula 1.

Further, the electron transport layer, the electron injection layer and the layer simultaneously transporting and injecting electrons include a compound represented by Chemical Formula 1.

Further, the organic material layer may include a light emitting layer or an electron transport layer, wherein the electron transport layer may include a compound represented by Chemical Formula 1.

Figures 1, 2:
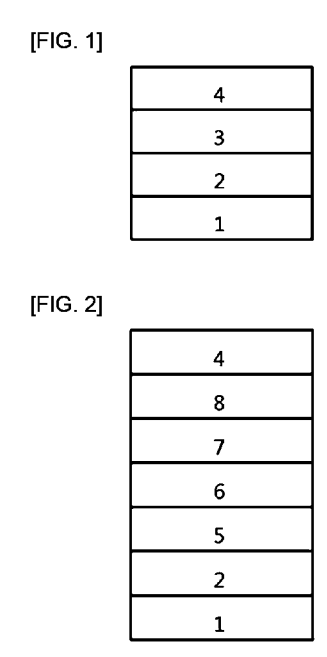

Further, the organic light emitting device according to the present disclosure may be a normal type organic light emitting device in which an anode, at least one organic material layer, and a cathode are sequentially stacked on a substrate. Further, the organic light emitting device according to the present disclosure may be an inverted type organic light emitting device in which a cathode, at least one organic material layer and an anode are sequentially stacked on a substrate. For example, the structure of an organic light emitting device according to an embodiment of the present disclosure is illustrated in FIGS. 1 and 2.

FIG. 1 shows an example of an organic light emitting device comprising a substrate 1, an anode 2, a light emitting layer 3, and a cathode 4. In such a structure, the compound represented by Chemical Formula 1 may be included in the light emitting layer.

FIG. 2 shows an example of an organic light emitting device comprising a substrate 1, an anode 2, a hole injection layer 5, a hole transport layer 6, a light emitting layer 7, an electron transport layer 8, and a cathode 4. In such a structure, the compound represented by Chemical Formula 1 may be included in at least one layer of the hole injection layer, the hole transport layer, the light emitting layer and the electron transport layer.

The organic light emitting device according to the present disclosure may be manufactured by materials and methods known in the art, except that at least one layer of the organic material layers includes the compound represented by Chemical Formula 1. In addition, when the organic light emitting device includes a plurality of organic material layers, the organic material layers may be formed of the same material or different materials.

For example, the organic light emitting device according to the present disclosure can be manufactured by sequentially stacking a first electrode, an organic material layer and a second electrode on a substrate. In this case, the organic light emitting device may be manufactured by depositing a metal, metal oxides having conductivity, or an alloy thereof on the substrate by using a PVD (physical vapor deposition) method such as a sputtering method or an e-beam evaporation method to form the anode, forming a organic material layer including the hole injection layer, the hole transport layer, the light emitting layer, and the electron transport layer thereon, and then depositing a material that can be used as the cathode thereon. In addition to such a method, the organic light emitting device may be manufactured by sequentially depositing a cathode material, an organic material layer and an anode material on a substrate.

In addition, the compound represented by Chemical Formula 1 may be formed into an organic layer by a solution coating method as well as a vacuum deposition method at the time of manufacturing an organic light emitting element. Herein, the solution coating method means a spin coating, a dip coating, a doctor blading, an inkjet printing, a screen printing, a spray method, a roll coating, or the like, but is not limited thereto.

In addition to such a method, the organic light emitting device may be manufactured by sequentially depositing a cathode material, an organic material layer, and an anode material on a substrate (International Publication WO 2003/012890). However, the manufacturing method is not limited thereto.

For example, the first electrode is an anode and the second electrode s a cathode, or the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SNO_2$:Sb; conductive polymers such as poly(3-methylthiophene), poly[3,4-(ethylene-1,2-dioxy)thiophene] (PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has an ability of transporting the holes, a hole injecting effect in the anode and an excellent hole injecting effect to the light emitting layer or the light emitting material, prevents movement of an exciton generated in the light emitting layer to the electron injection layer or the electron injection material, and has an excellent thin film forming ability. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which may receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is a material capable of emitting light in the visible light region by combining holes and electrons respectively transported from the hole transport layer and the electron transport layer, and having good quantum efficiency for fluorescence or phosphorescence. Specific examples include 8-hydroxy-quinoline aluminum complex ($Alq_3$); carbazole-based compounds; dimerized styryl compounds; BAlq; 10-hydroxybenzoquinoline-metal compounds; benzoxazole, benzothiazole and benzimidazole-based compounds; poly(p-phenylenevinylene)(PPV)-based polymers; spiro compounds; polyfluorene, rubrene, and the like, but are not limited thereto.

The light emitting layer may include a host material and a dopant material. The host material may be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, and fluoranthene compounds. Examples of heterocyclic compounds include carbazole derivatives, dibenzofuran derivatives, furan compounds, pyrimidine derivatives, and the like, but are not limited thereto.

Examples of the dopant material include an aromatic amine derivative, a styrylamine compound, a boron complex, a fluoranthene compound, a metal complex, and the like. Specific examples of the aromatic amine derivatives include substituted or unsubstituted fused aromatic ring derivatives having an arylamino group, examples thereof include pyrene, anthracene, chrysene, and periflanthene having the arylamino group, and the like, the styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transport layer is a layer receiving the electrons from the electron injection layer and transporting the electrons to the light emitting layer, the electron transport material is a material that can receive the electrons well from the cathode and transport the electrons to the light emitting layer, and a material having large mobility to the electrons is suitable. Specific examples thereof include an 8-hydroxyquinoline Al complex; a complex including $Alq_3$; an organic radical compound; a hydroxyflavone-metal complex, and the like, but are not limited thereto. The electron transport layer may be used together with a predetermined desired cathode material as used according to the prior art. Particularly, an example of an appropriate cathode material is a general material having the low work function and followed by an aluminum layer or a silver layer. Specific examples thereof include cesium, barium, calcium, ytterbium, and samarium, and each case is followed by the aluminum layer or the silver layer.

The electron injection layer is a layer injecting the electrons from the electrode, and a compound which has an ability of transporting the electrons, an electron injecting effect from the cathode, and an excellent electron injecting effect to the light emitting layer or the light emitting material, prevents movement of an exciton generated in the light emitting layer to the hole injection layer, and has an excellent thin film forming ability is preferable. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone, and the like, and its derivative, a metal complex compound, a nitrogen-containing 5-membered cycle derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present disclosure may be a front side emission type, a back side emission type, or a double side emission type according to the used material.

In addition, the compound represented by Chemical Formula 1 may be included in an organic solar cell or an organic transistor in addition to an organic light emitting device.

The preparation of the compound represented by Chemical Formula 1 and the organic light emitting device comprising the same will be described in detail in the following examples. However, these examples are presented for illustrative purposes only, and the scope of the present disclosure is not limited thereto.

Preparation Example 1

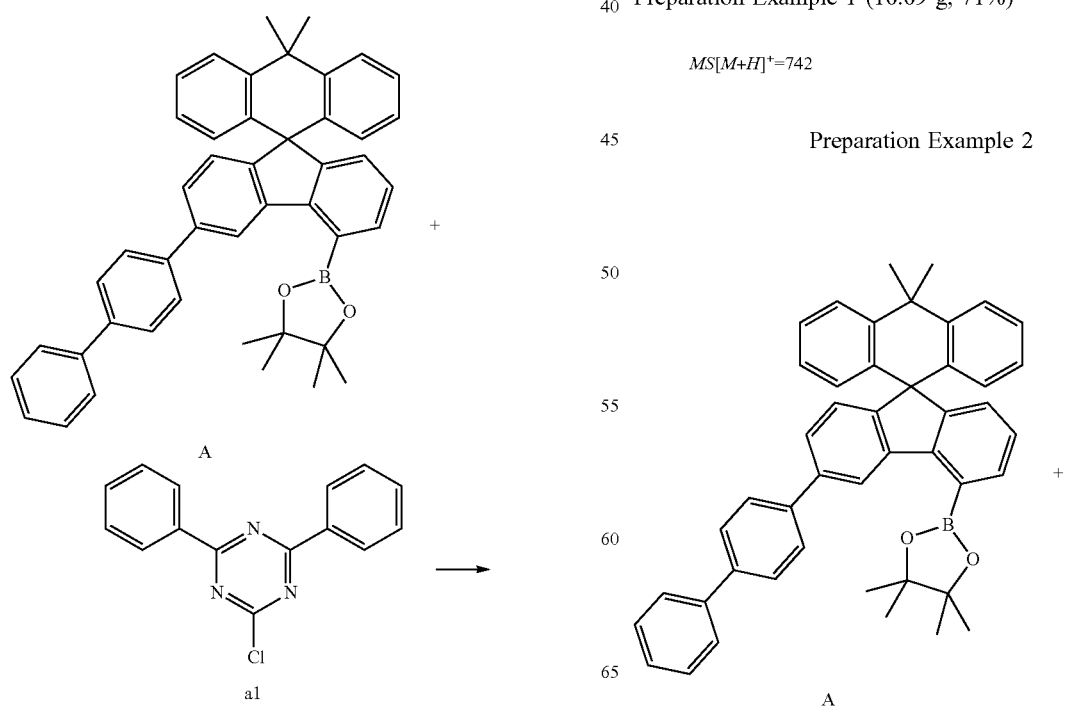

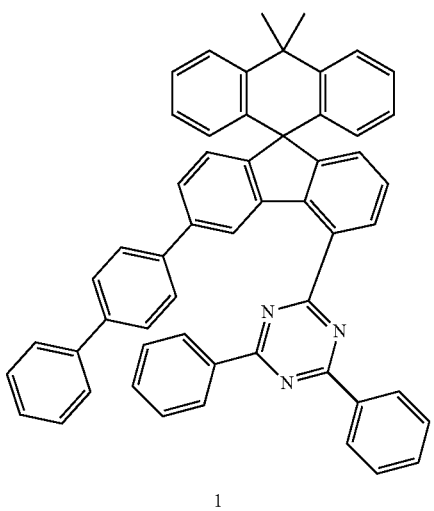

Compound A (12.73 g, 20.02 mmol) and compound a1 (3.67 g, 10.70 mmol) were completely dissolved in 240 mL of tetrahydrofuran in a 500 mL round-bottom flask under nitrogen atmosphere and then 2M potassium carbonate aqueous solution (120 mL) was added, and tetrakis-(triphenylphosphine)palladium (166 g, 0.57 mmol) was added thereto, and then the mixture was heated and stirred for 3 hours. After lowering the temperature to room temperature, the water layer was removed, dried over anhydrous magnesium sulfate, concentrated under reduced pressure, and recrystallized from 240 mL of ethyl acetate to prepare Preparation Example 1 (10.09 g, 71%)

$MS[M+H]^+=742$

Preparation Example 2

77
-continued a2

2

Compound A (9.07 g, 14.27 mmol) and compound a2 (4.66 g, 13.59 mmol) were completely dissolved in 220 mL of tetrahydrofuran in a 500 mL round-bottom flask under nitrogen atmosphere and then 2M potassium carbonate aqueous solution (110 mL) was added, and tetrakis-(triphenylphosphine)palladium (0.47 g, 0.41 mmol) was added thereto, and then the mixture was heated and stirred for 4 hours. After lowering the temperature to room temperature, the water layer was removed, dried over anhydrous magnesium sulfate, concentrated under reduced pressure, and recrystallized from 240 mL of ethyl acetate to prepare Preparation Example 2 (10.09 g, 71%)

$MS[M+H]^+=818$

78
Preparation Example 3

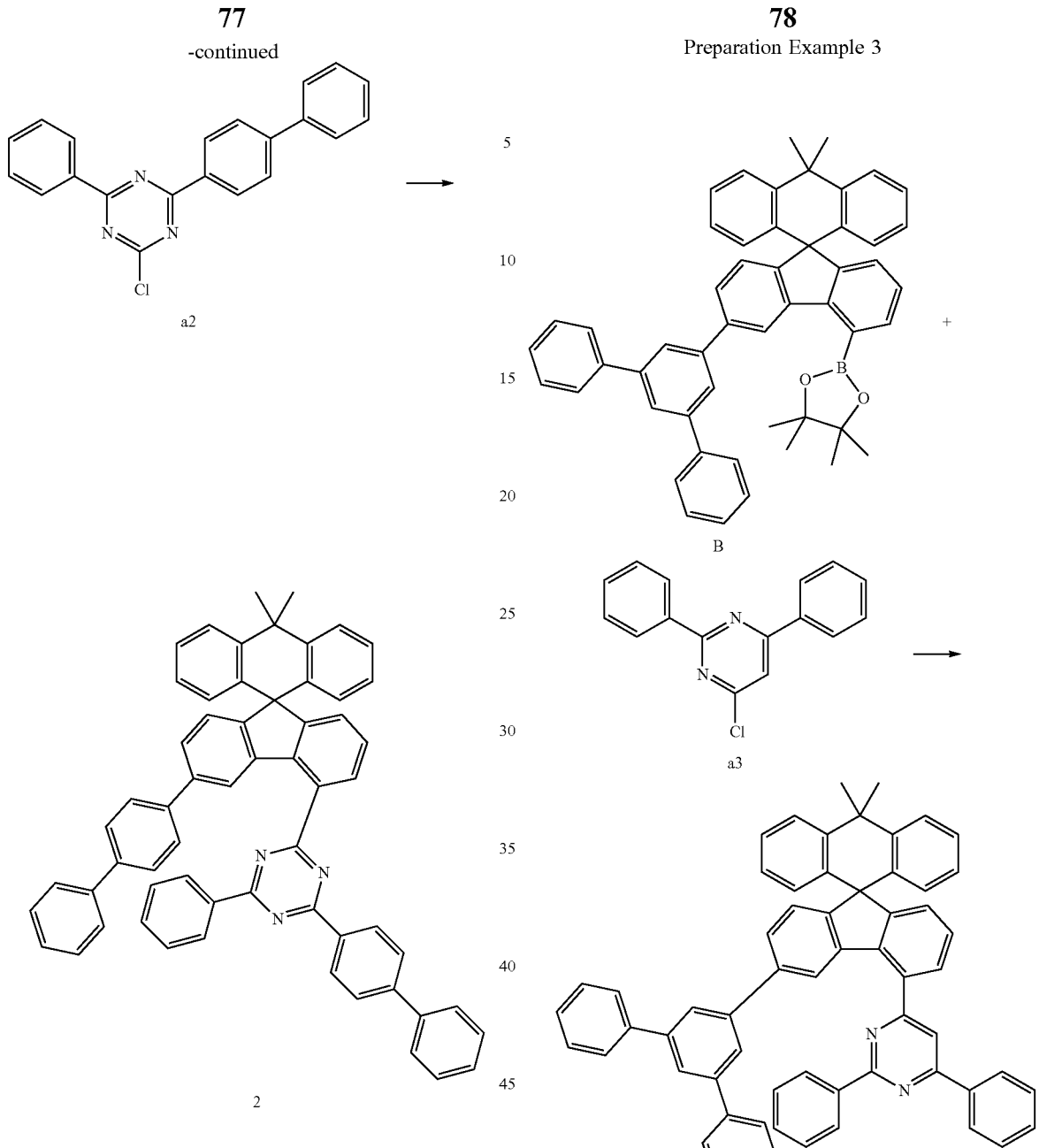

B a3

3

Compound B (14.84 g, 20.84 mmol) and compound a3 (5.28 g, 19.85 mmol) were completely dissolved in 180 mL of tetrahydrofuran in a 500 mL round-bottom flask under nitrogen atmosphere and then 2M potassium carbonate aqueous solution (90 mL) was added, and tetrakis-(triphenylphosphine)palladium (0.69 g, 0.60 mmol) was added thereto, and then the mixture was heated and stirred for 2 hours. After lowering the temperature to room temperature, the water layer was removed, dried over anhydrous magnesium sulfate, concentrated under reduced pressure, and recrystallized from 220 mL of ethyl acetate to prepare Preparation Example 3 (12.75 g, 79%).

$MS[M+H]^+=817$

Preparation Example 4

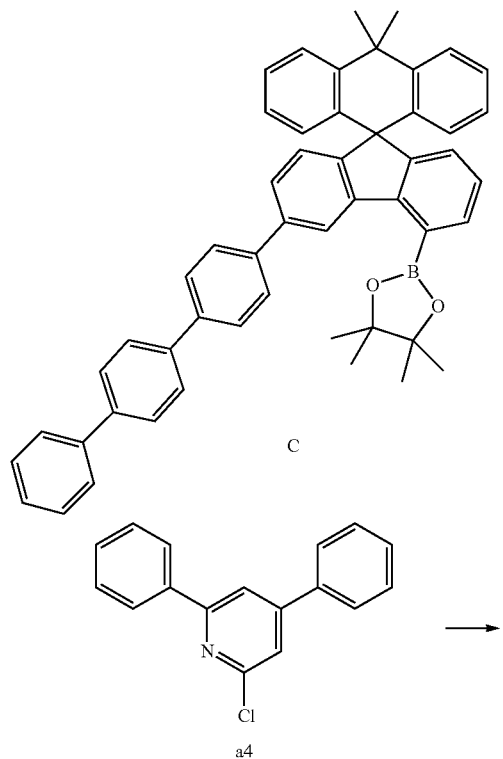

Compound C (13.51 g, 18.98 mmol) and compound a4 (4.79 g, 18.08 mmol) were completely dissolved in 200 mL of tetrahydrofuran in a 500 mL round-bottom flask under nitrogen atmosphere and then 2M potassium carbonate aqueous solution (100 mL) was added, and tetrakis-(triphenylphosphine)palladium (0.63 g, 0.54 mmol) was added thereto, and then the mixture was heated and stirred for 3 hours. After lowering the temperature to room temperature, the water layer was removed, dried over anhydrous magnesium sulfate, concentrated under reduced pressure, and recrystallized from 220 mL of ethyl acetate to prepare Preparation Example 4 (10.47 g, 68%).

$MS[M+H]^+=816$

Preparation Example 5

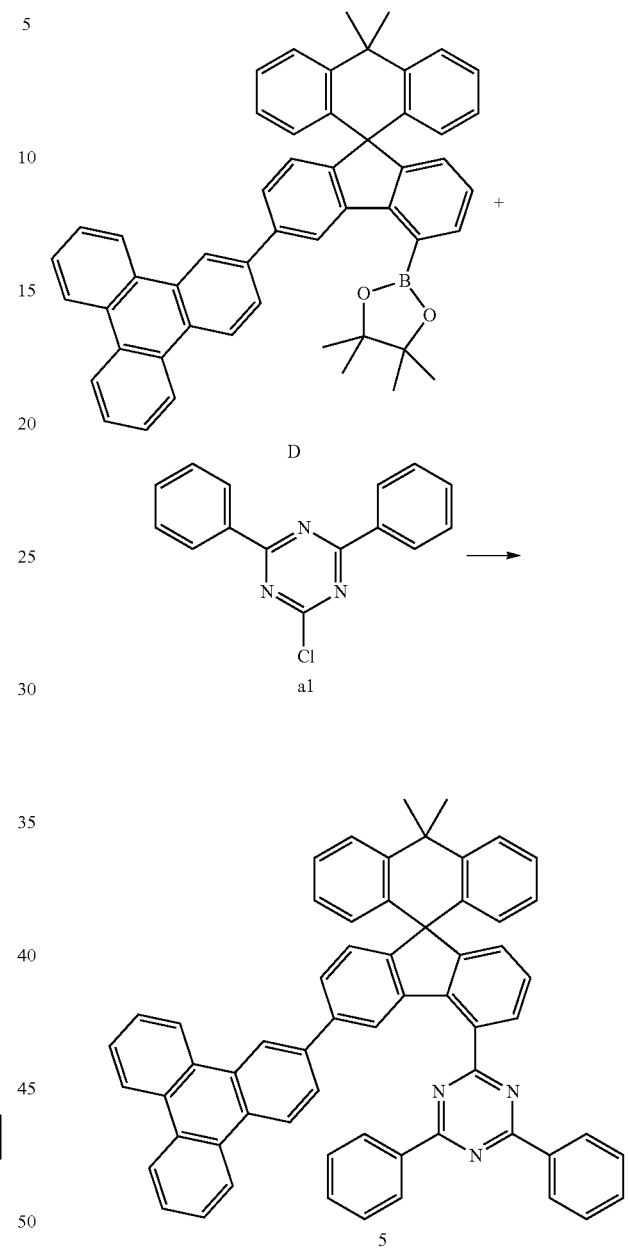

Compound D (12.84 g, 18.09 mmol) and compound a1 (4.60 g, 17.23 mmol) were completely dissolved in 220 mL of tetrahydrofuran in a 500 mL round-bottom flask under nitrogen atmosphere and then 2M potassium carbonate aqueous solution (110 mL) was added, and tetrakis-(triphenylphosphine)palladium (0.60 g, 0.52 mmol) was added thereto, and then the mixture was heated and stirred for 2 hours. After lowering the temperature to room temperature, the water layer was removed, dried over anhydrous magnesium sulfate, concentrated under reduced pressure, and recrystallized from 250 mL of ethyl acetate to prepare Preparation Example 5 (11.96 g, 85%).

$MS[M+H]^+=816$

Preparation Example 6

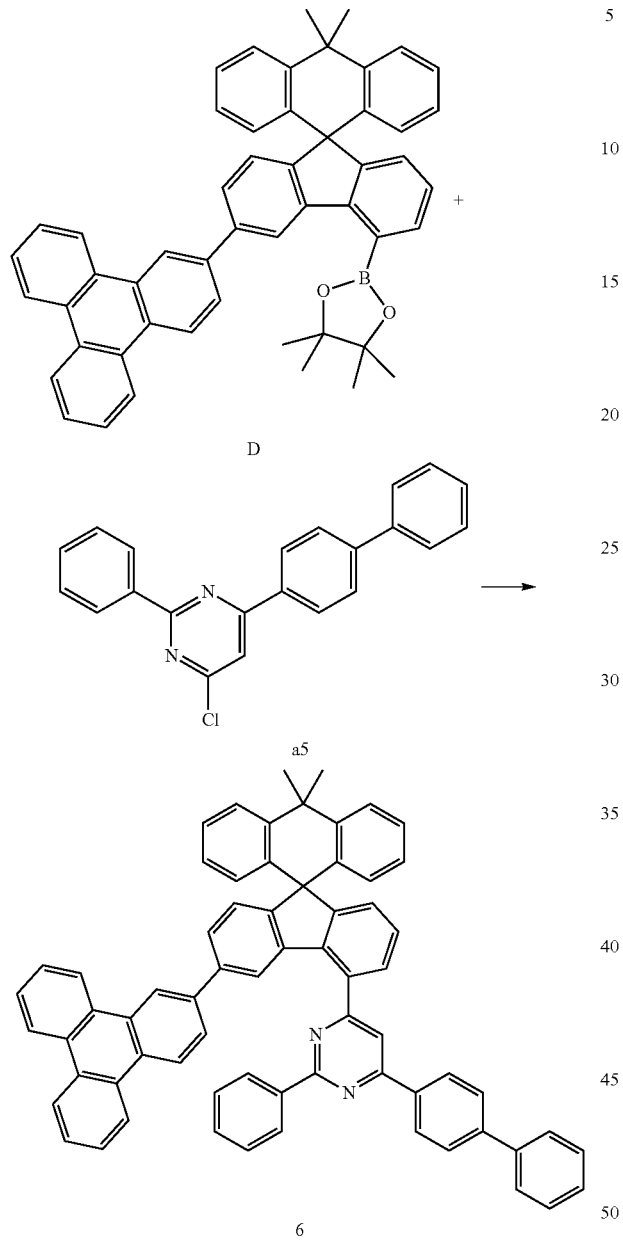

Compound D (8.41 g, 11.85 mmol) and compound a5 (3.86 g, 11.29 mmol) were completely dissolved in 280 mL of tetrahydrofuran in a 500 mL round-bottom flask under nitrogen atmosphere and then 2M potassium carbonate aqueous solution (140 mL) was added, and tetrakis-(triphenylphosphine)palladium (0,39 g, 0.34 mmol) was added thereto, and then the mixture was heated and stirred for 5 hours. After lowering the temperature to room temperature, the water layer was removed, dried over anhydrous magnesium sulfate, concentrated under reduced pressure, and recrystallized from 250 mL of ethyl acetate to prepare Preparation Example 6 (6.59 g, 66%).

$MS[M+H]^+=891$

Preparation Example 7

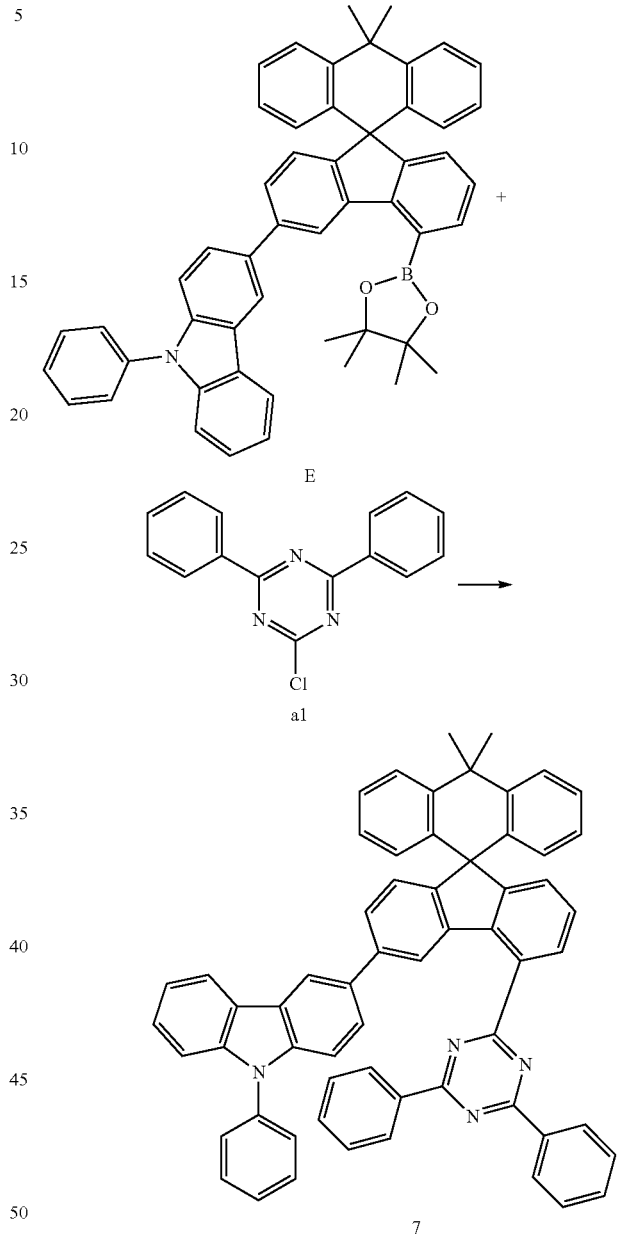

Compound E (11.78 g, 16.24 mmol) and compound al (4.13 g, 15.47 mmol) were completely dissolved in 260 mL of tetrahydrofuran in a 500 mL round-bottom flask under nitrogen atmosphere and then 2M potassium carbonate aqueous solution (130 mL) was added, and tetrakis-(triphenylphosphine)palladium (0.54 g, 0.46 mmol) was added thereto, and then the mixture was heated and stirred for 3 hours. After lowering the temperature to room temperature, the water layer was removed, dried over anhydrous magnesium sulfate, concentrated under reduced pressure, and recrystallized from 280 mL of ethyl acetate to prepare Preparation Example 7 (9.86 g, 77%).

$MS[M+H]^+=831$

Preparation Example 8

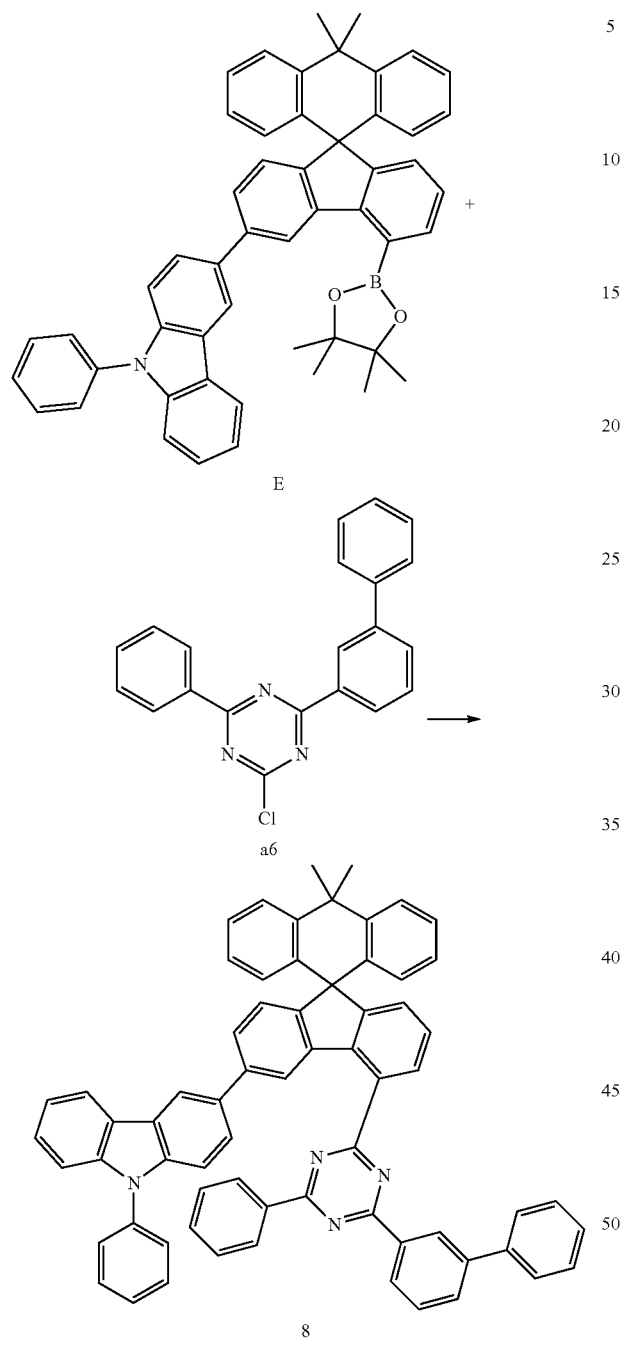

Compound E (8.61 g, 11.88 mmol) and compound a6 (3.88 g, 11.31 mmol) were completely dissolved in 220 mL of tetrahydrofuran in a 500 mL round-bottom flask under nitrogen atmosphere and then 2M potassium carbonate aqueous solution (110 mL) was added, and tetrakis-(triphenylphosphine)palladium (0.39 g, 0.34 mmol) was added thereto, and then the mixture was heated and stirred for 2 hours. After lowering the temperature to room temperature, the water layer was removed, dried over anhydrous magnesium sulfate, concentrated under reduced pressure, and recrystallized from 240 mL of ethyl acetate to prepare Preparation Example 8 (8.44 g, 82%).

MS[M+H]$^+$ 907

Preparation Example 9

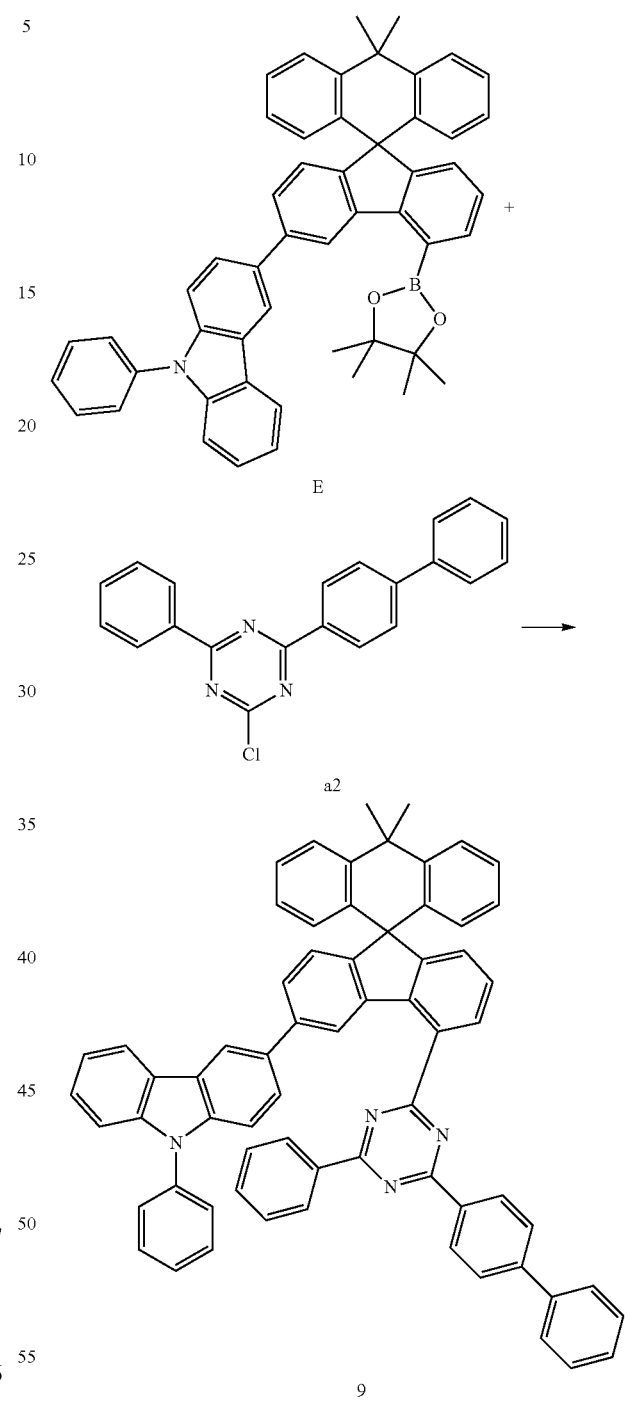

Compound E (7.88 g, 10.87 mmol) and compound a2 (3.55 g, 10.35 mmol) were completely dissolved in 180 mL of tetrahydrofuran in a 500 mL round-bottom flask under nitrogen atmosphere and then 2M potassium carbonate aqueous solution (90 mL) was added, and tetrakis-(triphenylphosphine)palladium (0.36 g, 0.31 mmol) was added thereto, and then the mixture was heated and stirred for 3 hours. After lowering the temperature to room temperature, the water layer was removed, dried over anhydrous magnesium sulfate, concentrated under reduced pressure, and recrystallized from 210 mL of ethyl acetate to prepare Preparation Example 9 (7.05 g, 75%).

MS[M+H]⁺ 907

Preparation Example 10

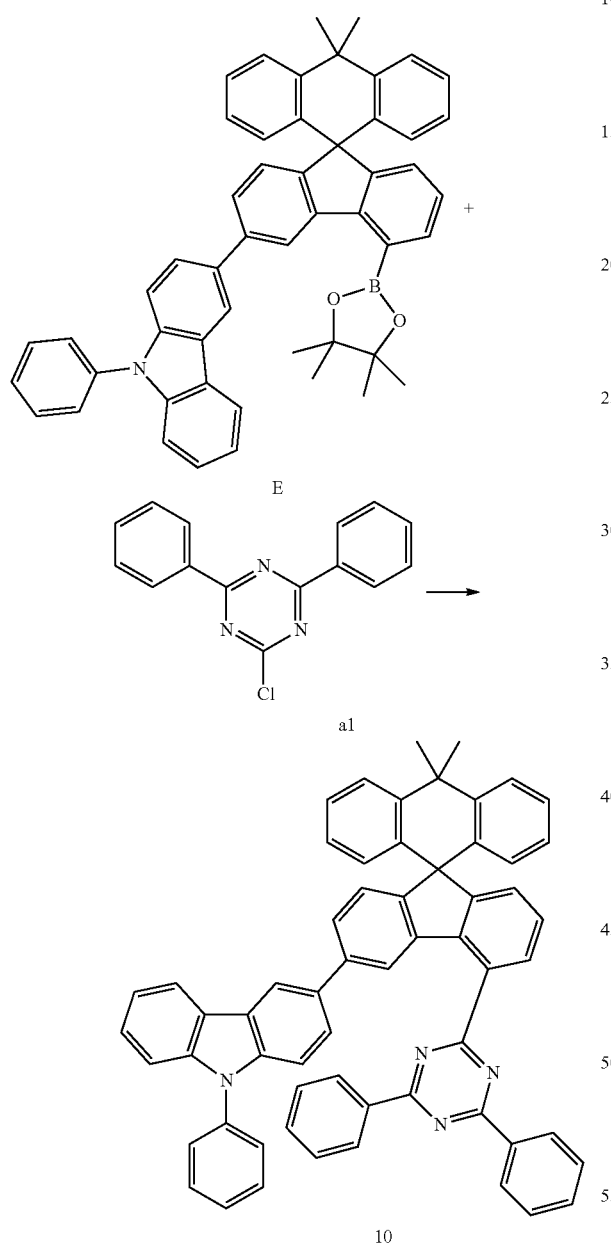

Compound E (11.58 g, 15.97 mmol) and compound a1 (4.06 g, 15.21 mmol) were completely dissolved in 220 mL of tetrahydrofuran in a 500 mL round-bottom flask under nitrogen atmosphere and then 2M potassium carbonate aqueous solution (110 mL) was added, and tetrakis-(triphenylphosphine)palladium (0.53 g, 0.46 mmol) was added thereto, and then the mixture was heated and stirred for 2 hours. After lowering the temperature to room temperature, the water layer was removed, dried over anhydrous magnesium sulfate, concentrated under reduced pressure, and recrystallized from 230 mL of ethyl acetate to prepare Preparation Example 10 (9.67 g, 77%).

MS[M+H]⁺=831

Preparation Example 11

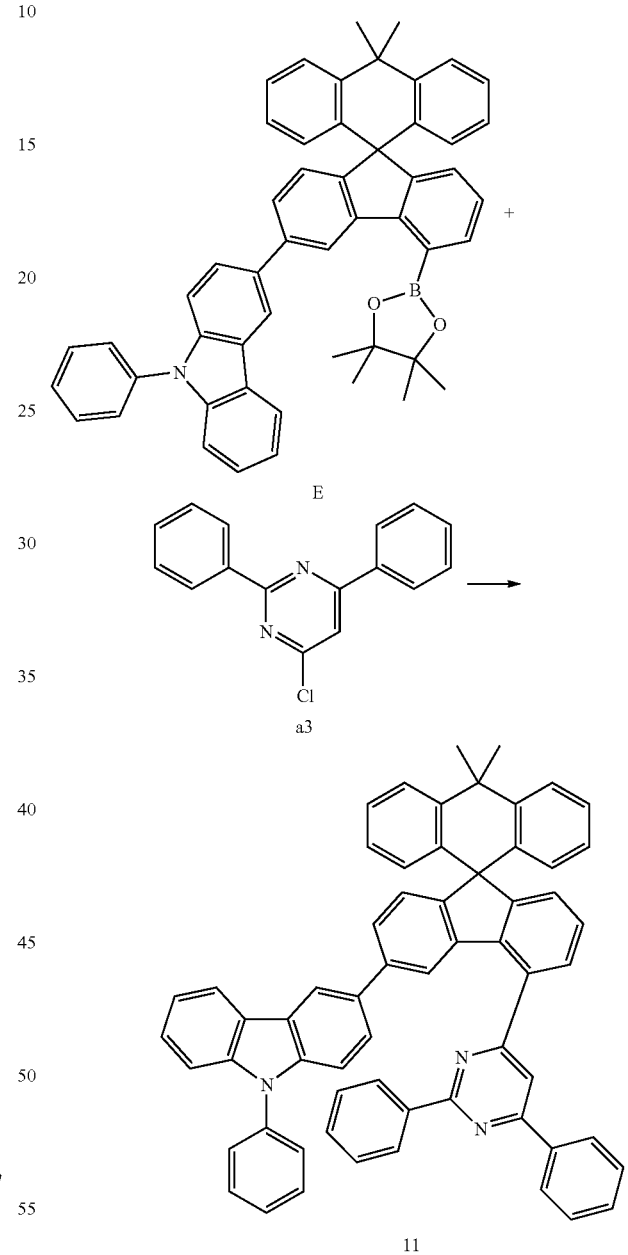

Compound E (9.04 g, 12.47 mmol) and compound a3 (3.17 g, 11.87 mmol) were completely dissolved in 240 mL of tetrahydrofuran in a 500 mL round-bottom flask under nitrogen atmosphere and then 2M potassium carbonate aqueous solution (120 mL) was added, and tetrakis-(triphenylphosphine)palladium (0.41 g, 0.36 mmol) was added thereto, and then the mixture was heated and stirred for 3 hours. After lowering the temperature to room temperature, the water layer was removed, dried over anhydrous magne-

Preparation Example 12

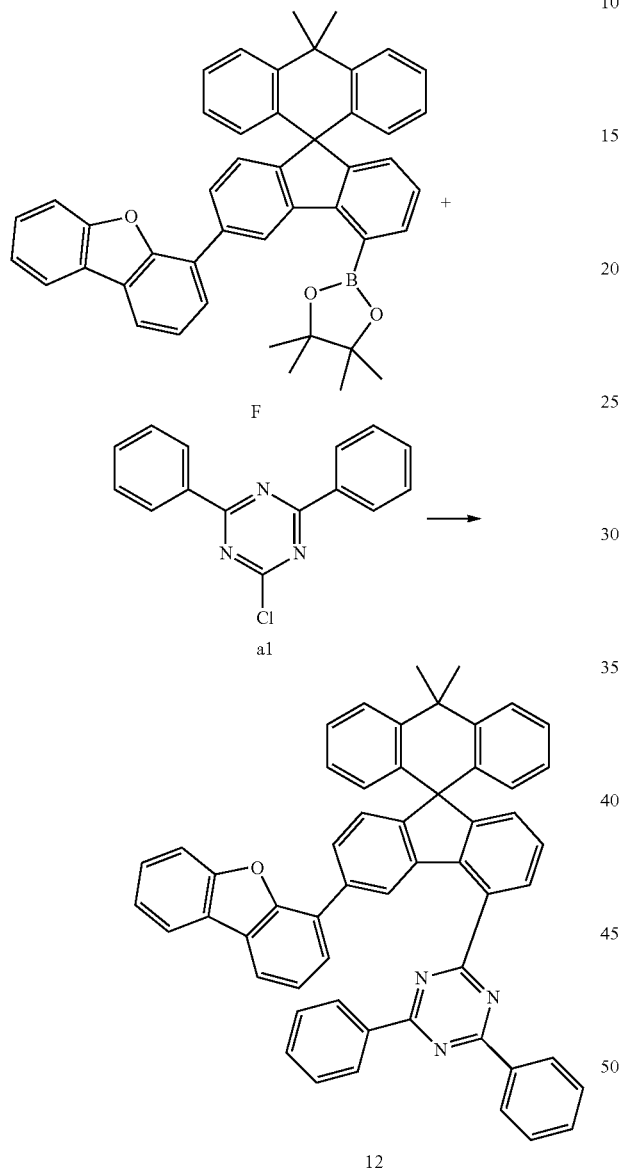

12

Compound F (11.99 g, 18.44 mmol) and compound a1 (4.69 g, 17.57 mmol) were completely dissolved in 260 mL of tetrahydrofuran in a 500 mL round-bottom flask under nitrogen atmosphere and then 2M potassium carbonate aqueous solution (110 mL) was added, and tetrakis-(triphenylphosphine)palladium (0.61 g, 0.53 mmol) was added thereto, and then the mixture was heated and stirred for 5 hours. After lowering the temperature to room temperature, the water layer was removed, dried over anhydrous magnesium sulfate, concentrated under reduced pressure, and recrystallized from 290 mL of ethyl acetate to prepare Preparation Example 12 (11.06 g, 83%).

$MS[M+H]^+=756$

Preparation Example 13

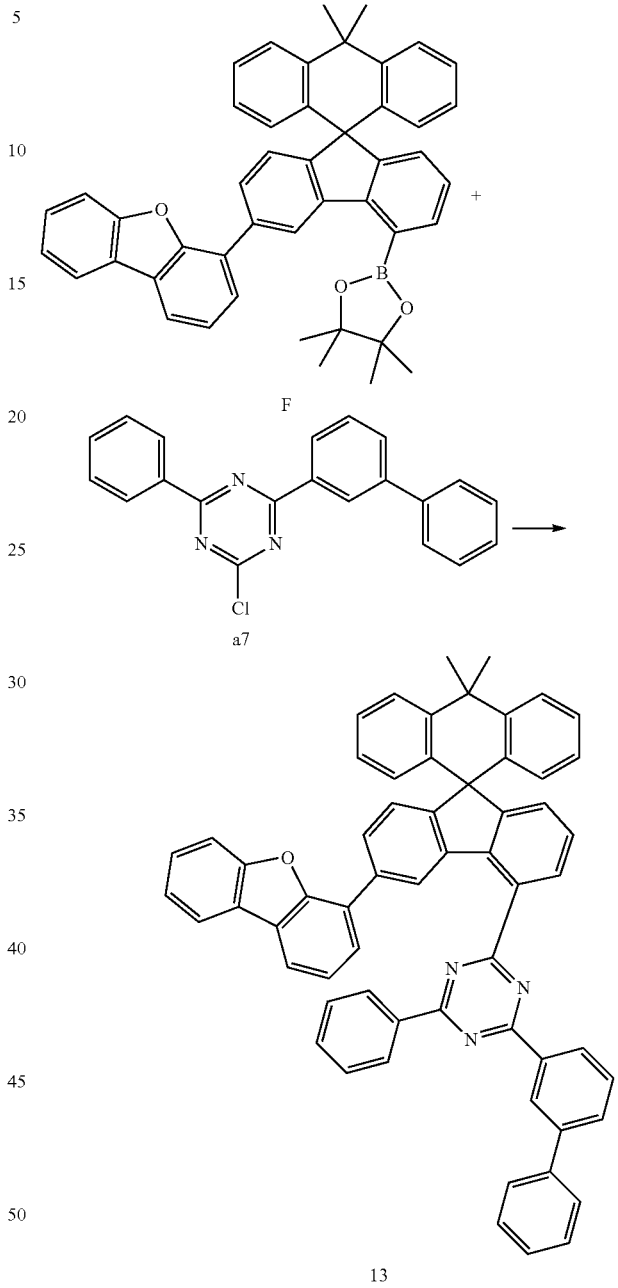

13

Compound F (10.33 g, 15.89 mmol) and compound a7 (5.19 g, 15.13 mmol) were completely dissolved in 260 mL of tetrahydrofuran in a 500 mL round-bottom flask under nitrogen atmosphere and then 2M potassium carbonate aqueous solution (110 mL) was added, and tetrakis-(triphenylphosphine)palladium (0.52 g, 0.45 mmol) was added thereto, and then the mixture was heated and stirred for 3 hours. After lowering the temperature to room temperature, the water layer was removed, dried over anhydrous magnesium sulfate, concentrated under reduced pressure, and recrystallized from 230 mL of ethyl acetate to prepare Preparation Example 13 (8.43 g, 66%).

$MS[M+H]^+832$ sium sulfate, concentrated under reduced pressure, and recrystallized from 310 mL of ethyl acetate to prepare Preparation Example 11 (8.19 g, 83%).

$MS[M+H]^+=830$

Example 1-1

A glass substrate on which a thin film of ITO (indium tin oxide) was coated in a thickness of 1,000 Å was put into distilled water containing the detergent dissolved therein and washed by the ultrasonic wave. The used detergent was a product commercially available from Fisher Co. and the distilled water was one which had been twice filtered by using a filter commercially available from Millipore Co. The ITO was washed for 30 minutes, and ultrasonic washing was then repeated twice for 10 minutes by using distilled water. After the washing with distilled water was completed, the substrate was ultrasonically washed with isopropyl alcohol, acetone, and methanol solvent, and dried, after which it was transported to a plasma cleaner. Then, the substrate was cleaned with oxygen plasma for 5 minutes, and then transferred to a vacuum evaporator.

On the ITO transparent electrode thus prepared, a compound represented by Chemical Formula HI1 below was thermally vacuum-deposited in a thickness of 150 Å to form a hole injection layer. A compound (1150 Å) represented by Chemical Formula HT1 below as a hole transport material was vacuum-deposited on the hole injection layer. Then, a compound represented by Chemical Formula EB1 below was vacuum-deposited on the hole transport layer in a thickness of 100 Å to form an electron blocking layer. Then, a compound represented by Chemical Formula BH below and a compound represented by Chemical Formula BD below were vacuum-deposited at a weight ratio of 25:1 on the electron blocking layer in a film thickness of 200 Å to form a light emitting layer. Then, a compound represented by Chemical Formula HB1 below was vacuum-deposited on the light emitting layer in a film thickness of 50 Å to form a hole blocking layer. Then, the compound of Preparation Example 1 previously prepared and a compound represented by Chemical Formula LiQ below was vacuum-deposited at a weight ratio of 1:1 on the hole blocking layer to form an electron transport layer having a thickness of 310 Å. A lithium fluoride (LiF) in a thickness of 12 Å and aluminum in a thickness of 1,000 Å were sequentially deposited on the electron transport layer to form a cathode.

HAT

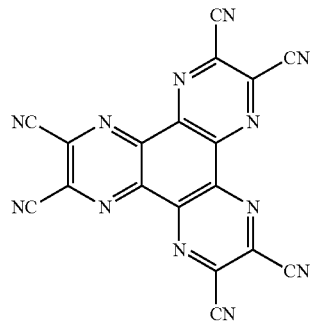

HT1

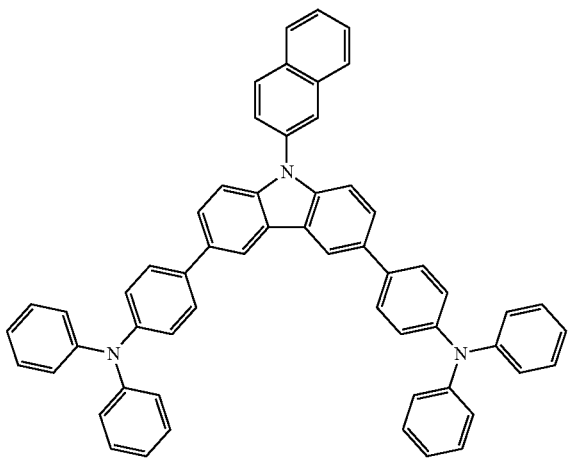

EB1

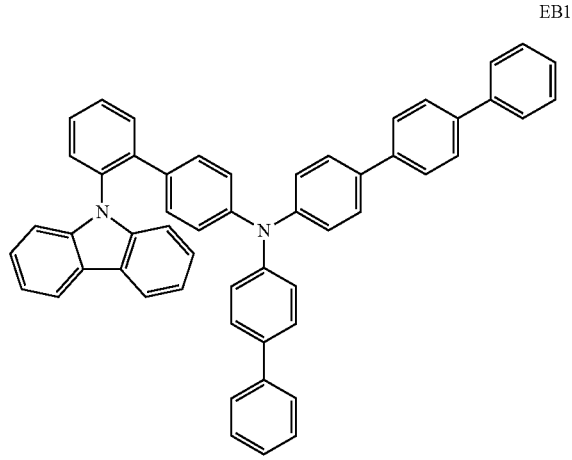

BH

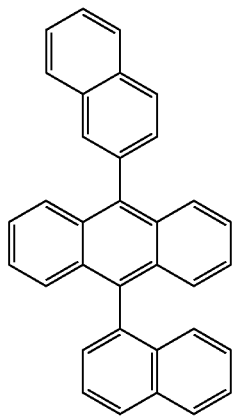

BD

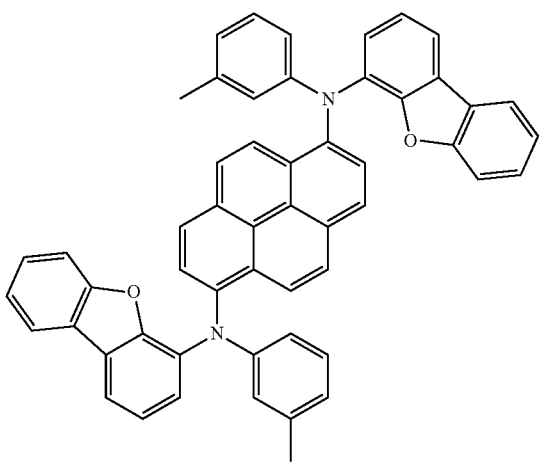

LiQ

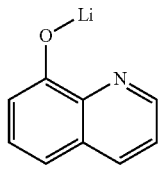

In the above process, the vapor deposition rate of the organic material was maintained at 0.4 to 0.7 Å/sec, the vapor deposition rate of lithium fluoride of the cathode was maintained at 0.3 Å/sec, the vapor deposition rate of aluminum was maintained at 2 Å/sec, and the degree of vacuum during vapor deposition was maintained at $2\times10^{-7}$~$5\times10^{-6}$ torr to manufacture an organic light emitting device.

Examples 1-2 to 1-12

The organic light emitting devices were manufactured in the same manner as in Example 1-1, except that the compounds shown in Table 1 below were used instead of the compound of Preparation Example 1.

HB1

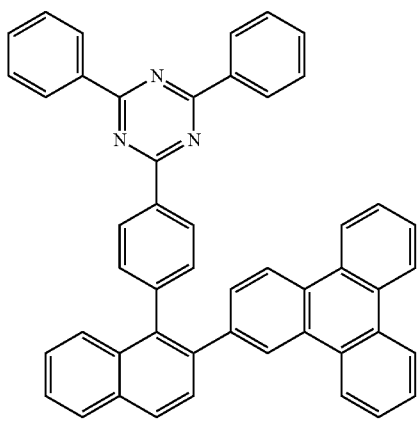

Comparative Examples 1-1 and 1-2

The organic light emitting devices were manufactured in the same manner as in Example 1-1, except that the compounds shown in Table 1 below were used instead of the compound of Preparation Example 1. The compounds ET1 and ET2 used in Table 1 below are as follows.

ET1

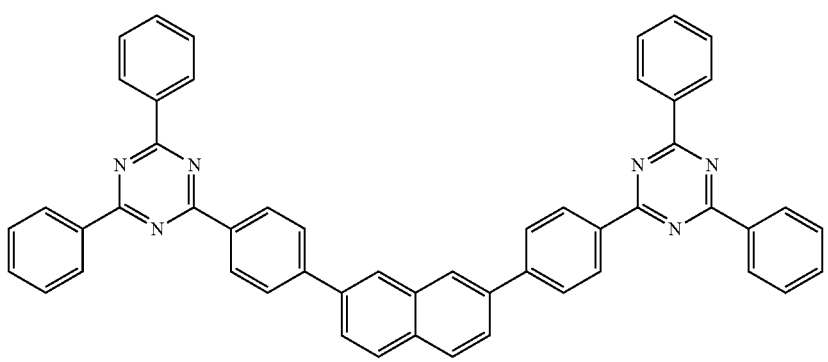

-continued

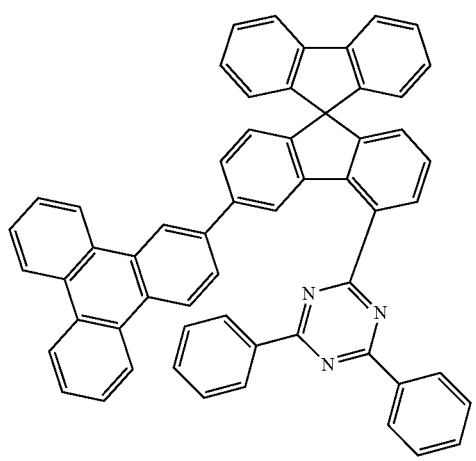

ET2

Experimental Example 1

The voltage, efficiency, color coordinate, and lifetime were measured by applying a current to the organic light emitting devices manufactured in the Examples and Comparative Examples, and the results are shown in Table 1 below. T95 means the time required for the luminance to be reduced to 95% from the initial luminance (1600 nit).

acridine as an electron transport layer exhibited characteristics of lower voltage and higher efficiency than the organic light emitting devices manufactured by using the compound of Comparative Example 1-2 having different types of cores as an electron transport layer. As shown in Table 1 above, it was confirmed that the compounds according to the present disclosure were excellent in electron transporting capability and thus applicable to an organic light emitting device.

TABLE 1

|  | Compound (Electron transport layer) | Voltage (V@10 mA/cm$^2$) | Efficiency (cd/A@10 mA/cm$^2$) | Color coordinate (x, y) | T95 (hr) |
| --- | --- | --- | --- | --- | --- |
| Example 1-1 | Preparation Example 1 | 4.31 | 6.03 | (0.140, 0.047) | 300 |
| Example 1-2 | Preparation Example 2 | 4.45 | 5.56 | (0.141, 0.044) | 290 |
| Example 1-3 | Preparation Example 3 | 4.63 | 5.79 | (0.140, 0.047) | 300 |
| Example 1-4 | Preparation Example 4 | 4.41 | 6.03 | (0.141, 0.044) | 290 |
| Example 1-5 | Preparation Example 5 | 4.63 | 5.82 | (0.141, 0.043) | 275 |
| Example 1-6 | Preparation Example 6 | 4.44 | 5.72 | (0.142, 0.043) | 290 |
| Example 1-7 | Preparation Example 7 | 4.66 | 5.76 | (0.141, 0.045) | 260 |
| Example 1-8 | Preparation Example 8 | 4.47 | 5.97 | (0.140, 0.045) | 295 |
| Example 1-9 | Preparation Example 9 | 4.38 | 6.05 | (0.142, 0.046) | 290 |
| Example 1-10 | Preparation Example 10 | 4.46 | 5.95 | (0.141, 0.047) | 300 |
| Example 1-11 | Preparation Example 12 | 4.45 | 5.94 | (0.142, 0.046) | 305 |
| Example 1-12 | Preparation Example 13 | 4.62 | 5.73 | (0.141, 0.044) | 285 |
| Comparative Example 1-1 | ET 1 | 5.12 | 5.43 | (0.141, 0.044) | 240 |
| Comparative Example 1-2 | ET 2 | 4.93 | 5.33 | (0.141, 0.044) | 225 |

As shown in Table 1, the organic light emitting devices manufactured using the compounds of the present disclosure as an electron transport layer exhibited excellent characteristics in terms of efficiency, driving voltage and/or stability of the organic light emitting device. In particular, the organic light emitting device manufactured by using the compounds of the present disclosure in the form of fluorene-9,8-indolo-

Comparative Example 2-1

The organic light emitting devices were manufactured in the same manner as in Comparative Example 1-1, except that, instead of using the compound represented by Chemical Formula BH and the compound represented by Chemical Formula BD as a light emitting layer, a compound represented by Chemical Formula GH1 below and a compound represented by Chemical Formula GD below were vacuum-deposited at a weight ratio of 20:1 in a film thickness of 350 Å to form a light emitting layer.

compound represented by Chemical Formula GH2 below was used instead of the compound of the Chemical Formula GH1.

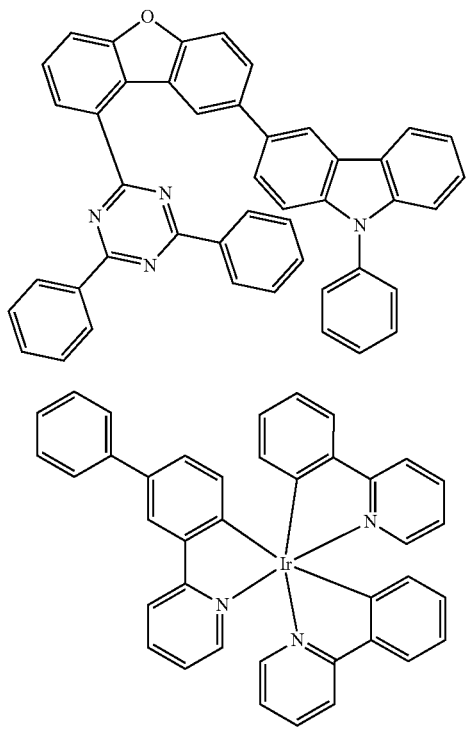

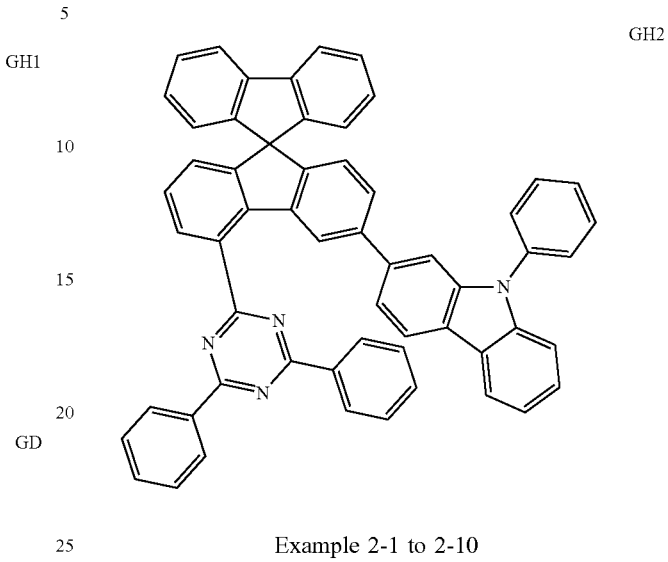

Comparative Example 2-2

The organic light emitting device was manufactured in the same manner as in Comparative Example 1-1, except that a Example 2-1 to 2-10

The organic light emitting devices were manufactured in the same manner as in Comparative Example 1-1, except that the compounds shown in Table 2 below were used instead of the compound of the Chemical Formula GH1.

Experimental Example 2

The voltage, efficiency, color coordinate, and lifetime were measured by applying a current to the organic light emitting devices manufactured in the Examples and Comparative Examples, and the results are shown in Table 2 below. T95 means the time required for the luminance to be reduced to 95% from the initial luminance (6000 nit).

TABLE 2

| | Compound (Green light emitting layer host) | Voltage (V@10 mA/cm$^2$) | Efficiency (cd/A@10 mA/cm$^2$) | Color coordinate (x, y) | T95 (hr) |
|---|---|---|---|---|---|
| Comparative Example 2-1 | GH1 | 4.05 | 106.45 | (0.251, 0.715) | 280 |
| Comparative Example 2-2 | GH2 | 4.18 | 108.42 | (0.254, 0.702) | 290 |
| Example 2-1 | Preparation Example 1 | 3.65 | 126.03 | (0.255, 0.717) | 340 |
| Example 2-2 | Preparation Example 2 | 3.77 | 121.72 | (0.254, 0.716) | 335 |
| Example 2-3 | Preparation Example 5 | 3.76 | 121.61 | (0.253, 0.717) | 325 |
| Example 2-4 | Preparation Example 6 | 3.78 | 122.76 | (0.256, 0.719) | 330 |
| Example 2-5 | Preparation Example 7 | 3.84 | 123.58 | (0.252, 0.718) | 325 |
| Example 2-6 | Preparation Example 8 | 3.75 | 121.47 | (0.255, 0.716) | 345 |
| Example 2-7 | Preparation Example 9 | 3.74 | 121.94 | (0.255, 0.707) | 350 |
| Example 2-8 | Preparation Example 10 | 3.86 | 119.65 | (0.256, 0.707) | 350 |
| Example 2-9 | Preparation Example 12 | 3.88 | 119.8 | (0.254, 0.706) | 355 |
| Example 2-10 | Preparation Example 13 | 3.87 | 117.73 | (0.255, 0.708) | 335 |

As shown in Table 2, the organic light emitting devices manufactured using the compounds of the present disclosure as a green light emitting layer exhibited excellent characteristics in terms of efficiency, driving voltage and/or stability of the organic light emitting device. In particular, the organic light emitting device manufactured by using the compounds of the present disclosure in the form of fluorene-9,8-indoloacridine as a host of the green light emitting layer exhibited characteristics of lower voltage and higher efficiency than the organic light emitting devices manufactured by using the compound of Comparative Example 2-2 having different types of cores as a host of the green light emitting layer. As shown in Table 2 above, it was confirmed that the compounds according to the present disclosure were excellent in light emitting capability and thus applicable to an organic light-emitting device.

EXPLANATION OF SIGN

| | |
|---|---|
| 1: substrate | 2: anode |
| 3: light emitting layer | 4: cathode |
| 5: hole injection layer | 6: hole transport layer |
| 7: light emitting layer | 8: electron transport layer |

The invention claimed is:

1. A compound represented by Chemical Formula 1:

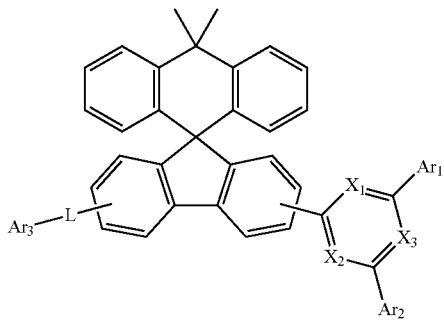

[Chemical Formula 1]

wherein, in Chemical Formula 1, $X_1$ to $X_3$ is each independently N, or CH, and at least one of $X_1$ to $X_3$ is N, $Ar_1$ and $Ar_2$ are each independently a substituted or unsubstituted $C_{6-60}$ aryl; or a substituted or unsubstituted $C_{2-60}$ heteroaryl containing one or more heteroatoms selected from the group consisting of N, O and S, L is a bond; or a substituted or unsubstituted $C_{6-60}$ arylene, and $Ar_3$ is a substituent group selected from the group consisting of phenyl, biphenyl, terphenylyl, quaterphenylyl, naphthyl, phenanthrenyl, anthracenyl, triphenylenyl, dimethylfluorenyi, diphenylfluorenyl, dibenzofuranyl, dibenzothiophenyl, carbazolyl, 9-phenylcarbazolyl, quinolinyl, isoquinolinyl, a substituent represented by Chemical Formula 2, and a substituent represented by Chemical Formula 3, wherein said substituent group is unsubstituted or further substituted by cyano,

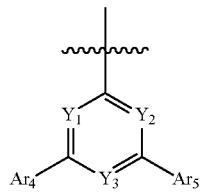

[Chemical Formula 2]

wherein, in Chemical Formula 2, $Y_1$ to $Y_3$ are each independently N, or CH, provided that at least one of $Y_1$ to $Y_3$ is N, and $Ar_4$ and $Ar_5$ are each independently a substituted or unsubstituted $C_{6-60}$ aryl,

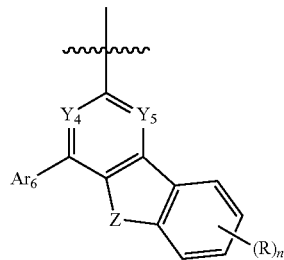

[Chemical Formula 3]

wherein, in Chemical Formula 3, $Y_4$ and $Y_5$ are each independently N or CH, provided that at least one of $Y_4$ and $Y_5$ is N, and Z is O or S, $Ar_6$ is a substituted or unsubstituted $C_{6-60}$ aryl; or a substituted or unsubstituted heteroaryl containing one or more heteroatoms selected from the group consisting of N, O and S;

R is hydrogen; a substituted or unsubstituted $C_{6-60}$ aryl; or a substituted or unsubstituted heteroaryl containing one or more heteroatoms selected from the group consisting of N, O and S, and n is an integer of 1 to 4.

2. The compound of claim 1, wherein the compound represented by Chemical Formula 1 is a compound represented by Chemical Formula 1-1:

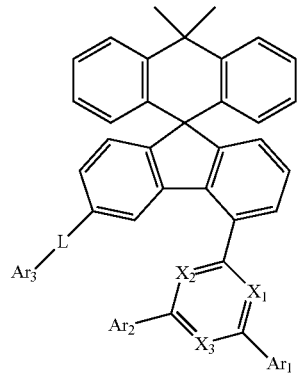

[Chemical Formula 1-1]

wherein, in Chemical Formula 1-1,

X1 to X3, Ar1 to Ar3, and L are as defined in claim 1.

3. The compound of claim 1, wherein $Ar_1$ and $Ar_2$ are each independently phenyl, biphenylyl, terphenylyl, quaterphenylyl, naphthyl, anthracenyl, phenanthrenyl, triphenylenyl, dimethyfluorenyl, diphenylfluorenyl, dibenzofuranyl, carbazolyl, 9-phenylcarbazolyl, or dibenzothiophenyl.

4. The compound of claim 1, wherein $Ar_1$ and $Ar_2$ are each independently phenyl, or biphenylyl.

5. The compound of claim 1, wherein

L is a bond, phenylene, naphthalenediyl, or anthracenediyl.

6. The compound of claim 1, wherein $Ar_4$ and $Ar_5$ are each independently phenyl, biphenylyl, or naphthyl.

7. The compound of claim 1, wherein $Ar_6$ is phenyl, biphenylyl, dimethylfluorenyl, diphenyfluorenyl, dibenzofuranyl, dibenzothiophenyl, carbazolyl, or 9-phenylcarbazolyl.

8. The compound of claim 1, wherein the compound represented by Chemical Formula 1 is any one selected from the group consisting of the following:

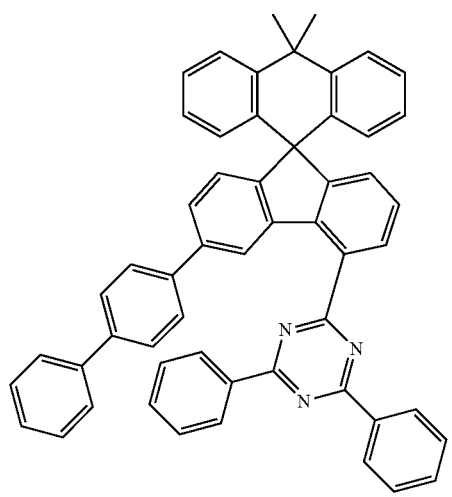

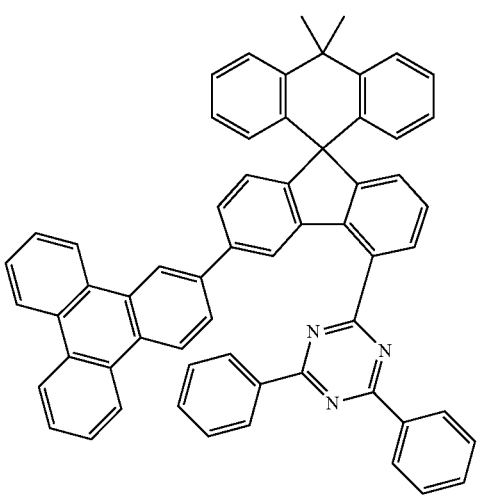

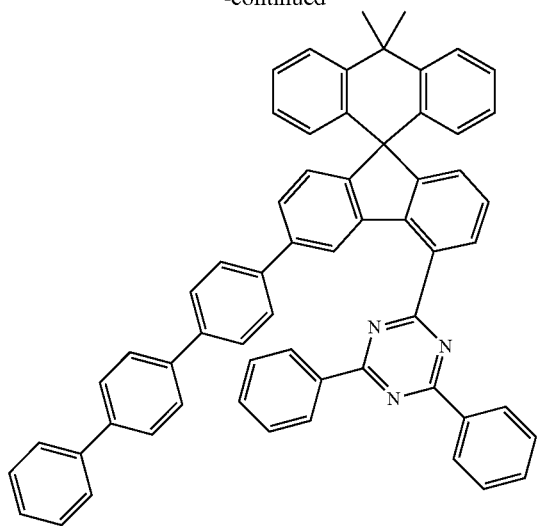

-continued

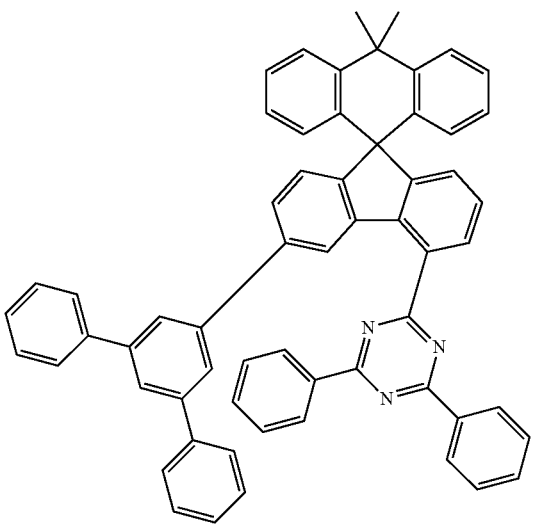

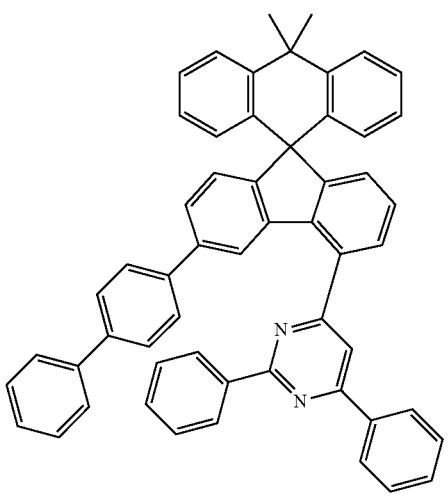

101
-continued
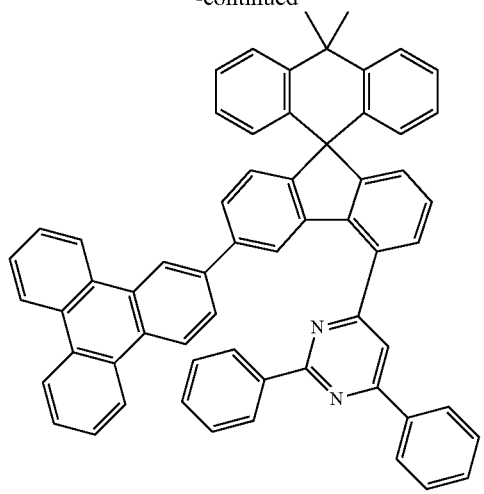
102
-continued
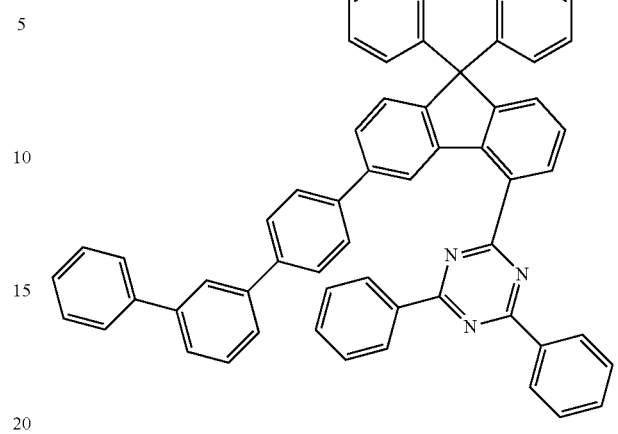
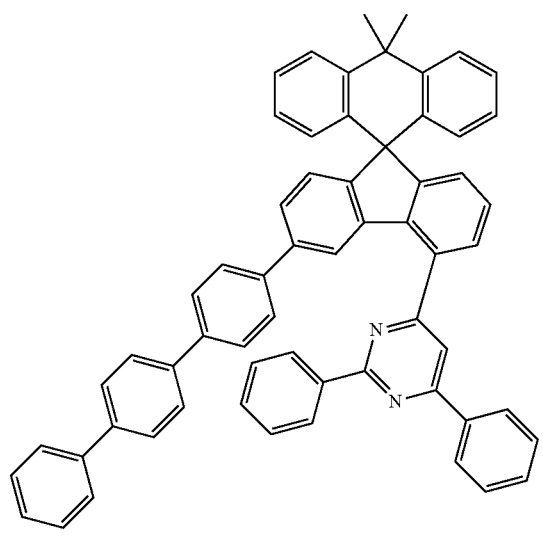
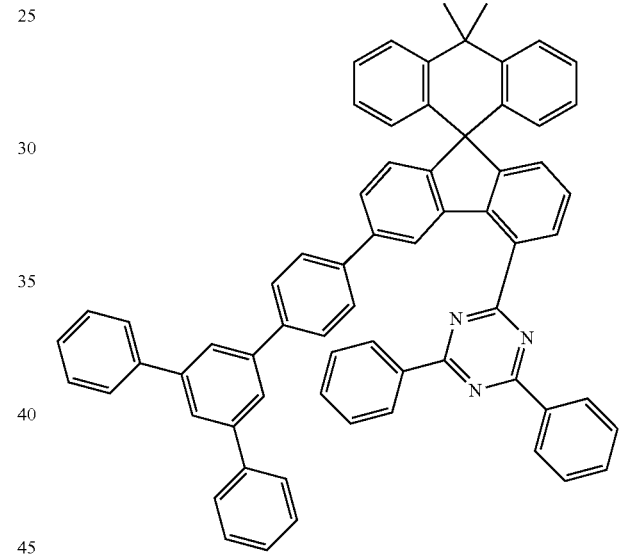
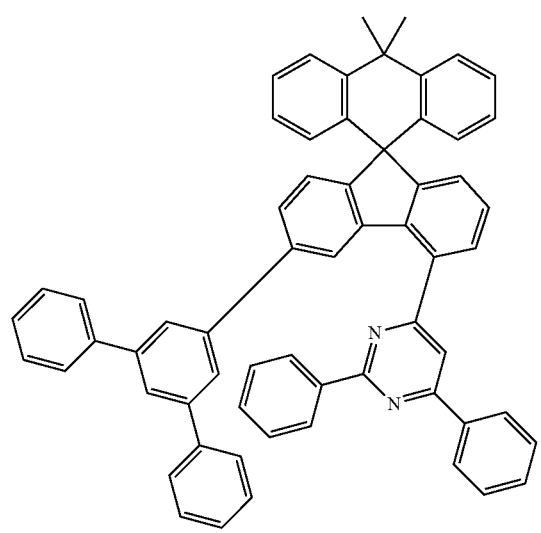
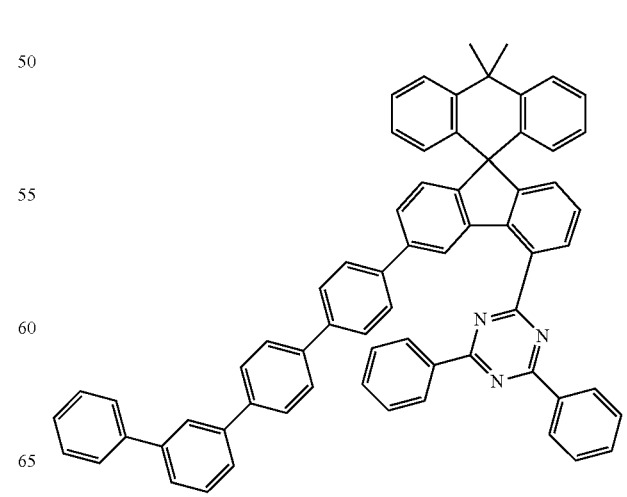

103
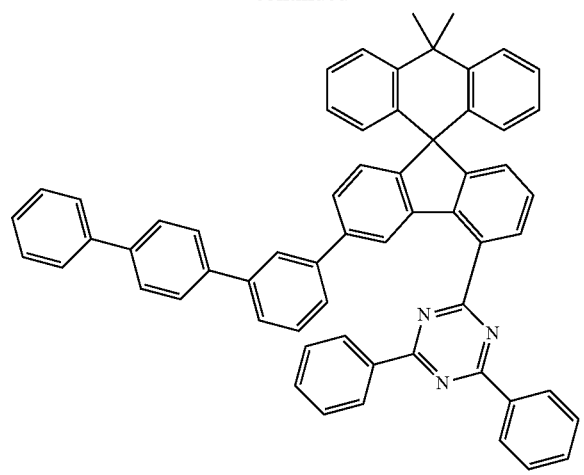
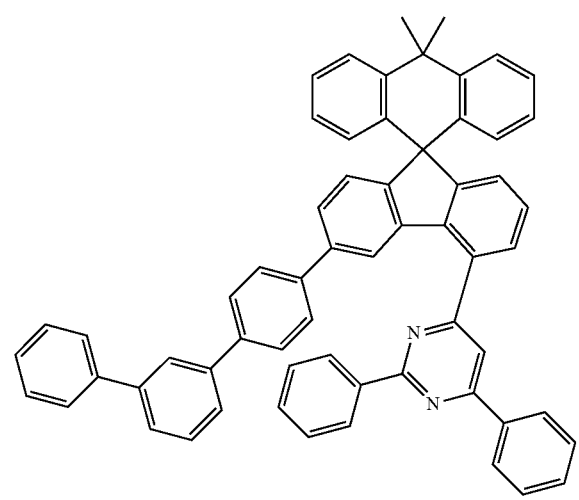
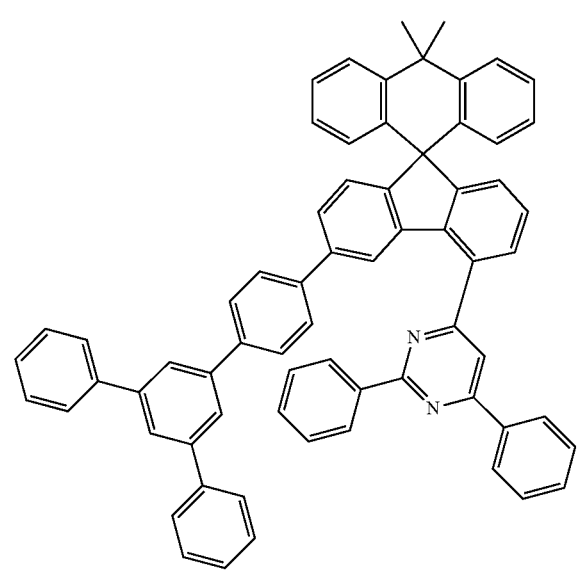
104
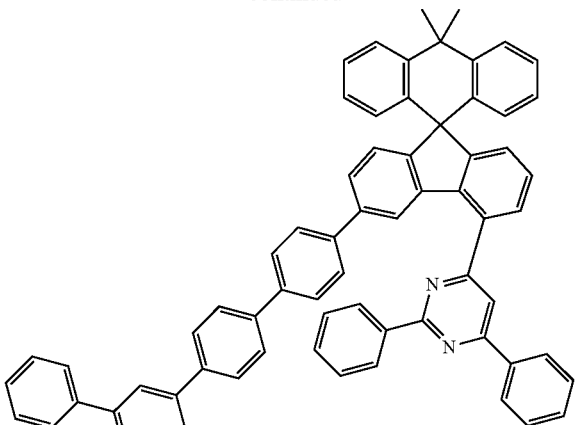
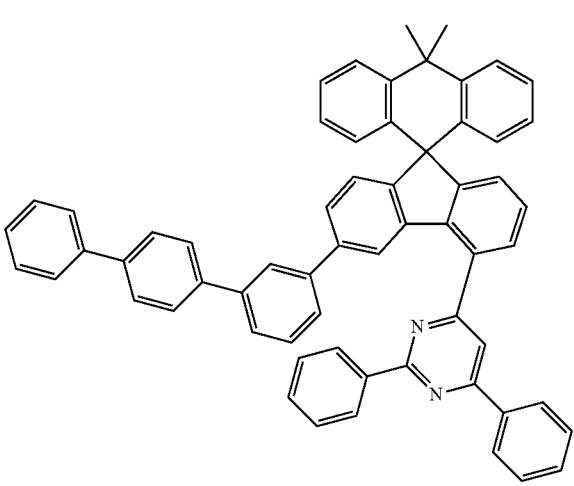
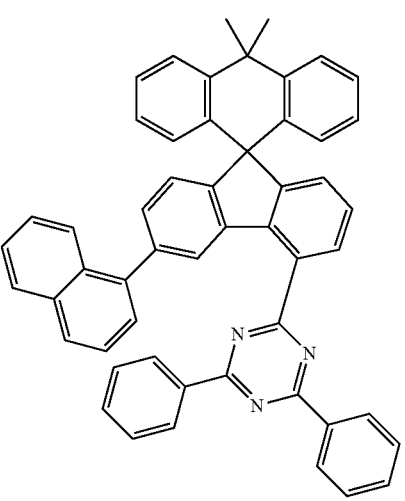

105
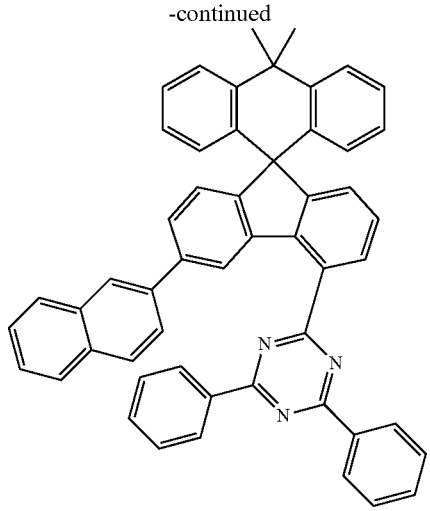
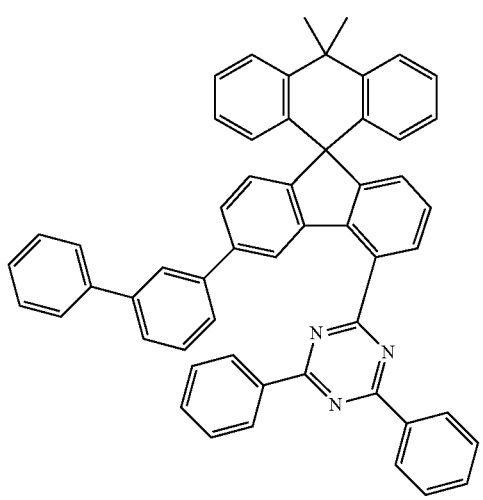
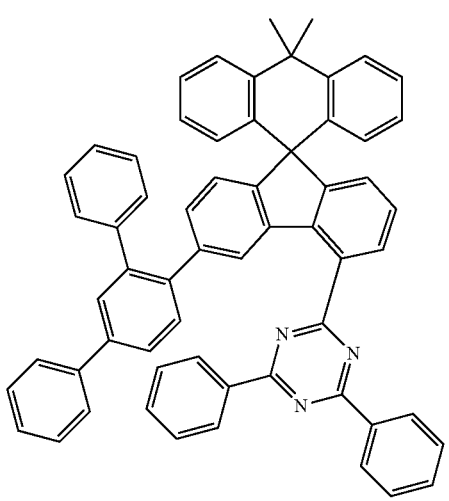
106
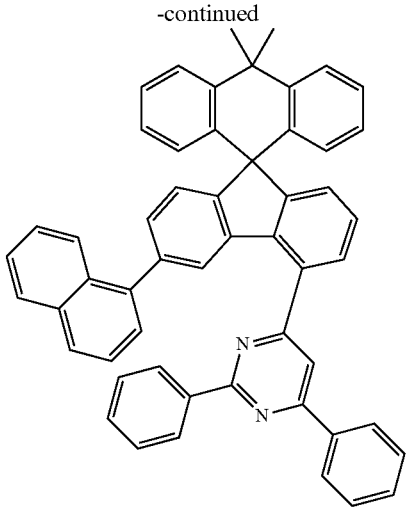
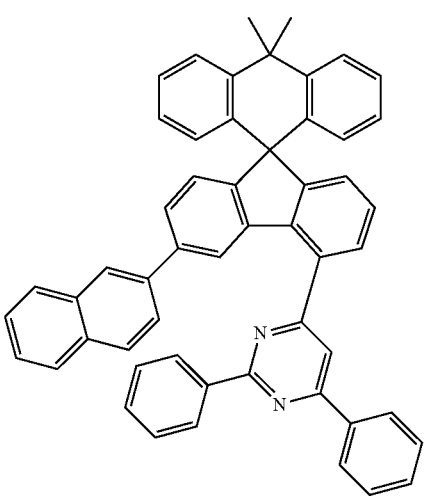
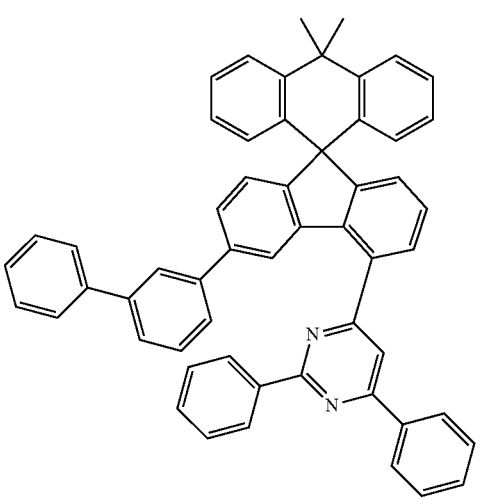

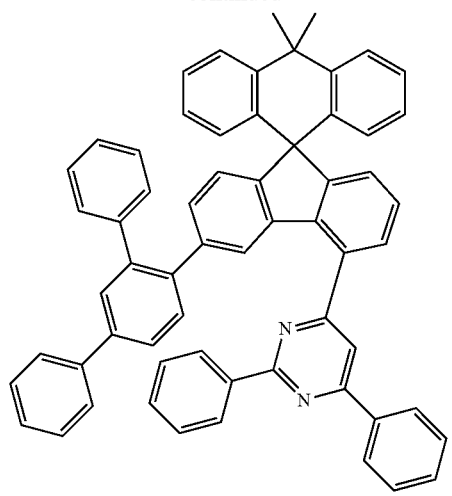
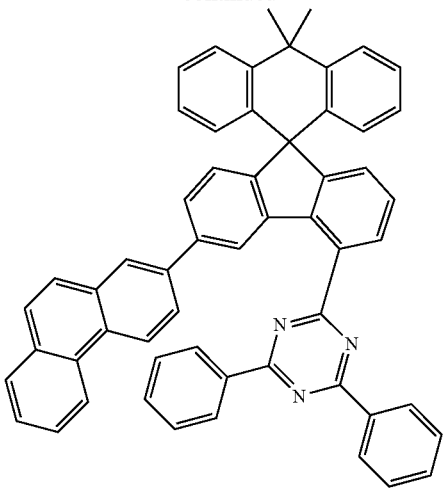
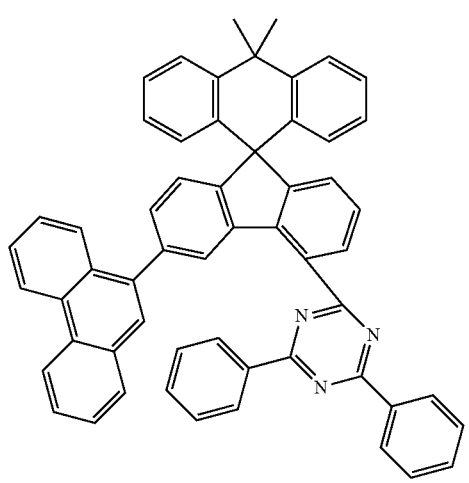
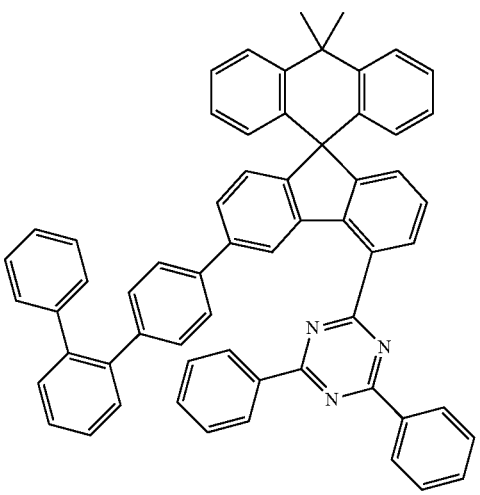
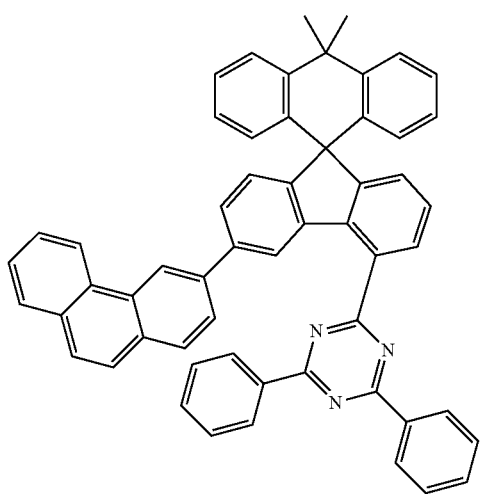
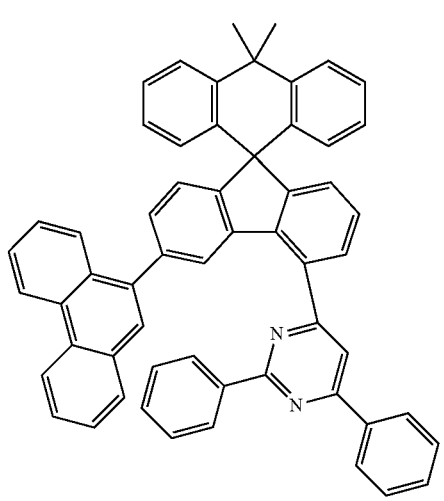

109
-continued
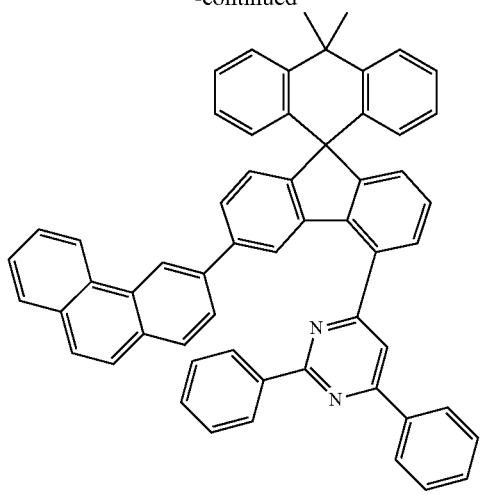
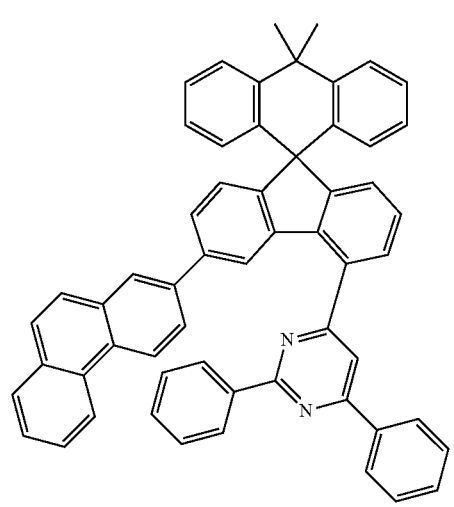
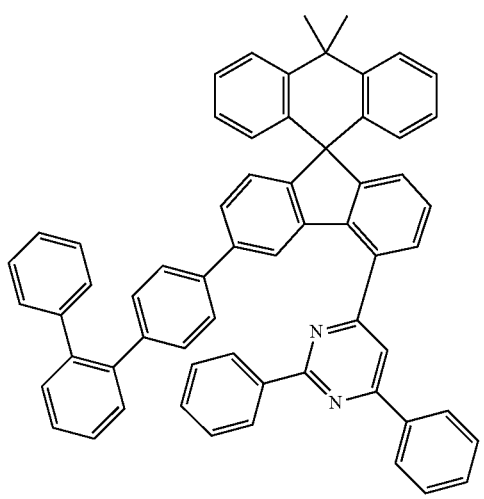
110
-continued
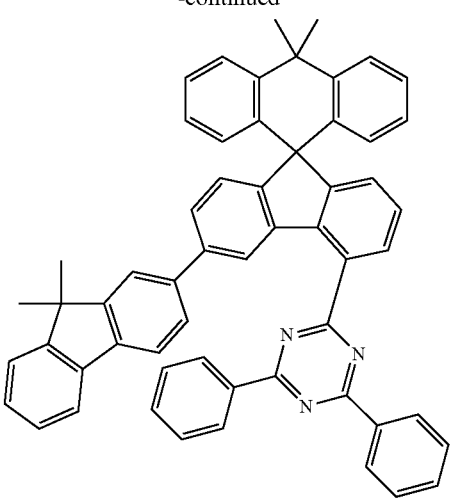
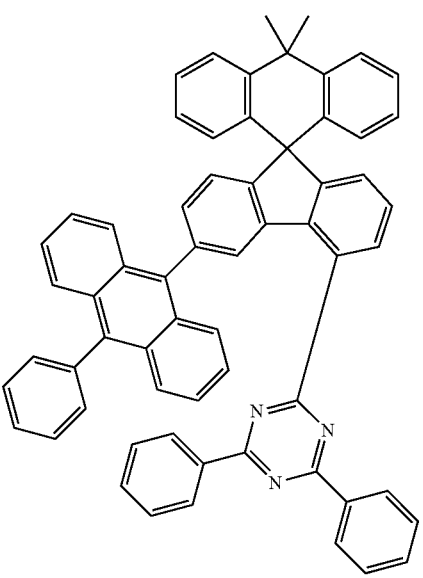
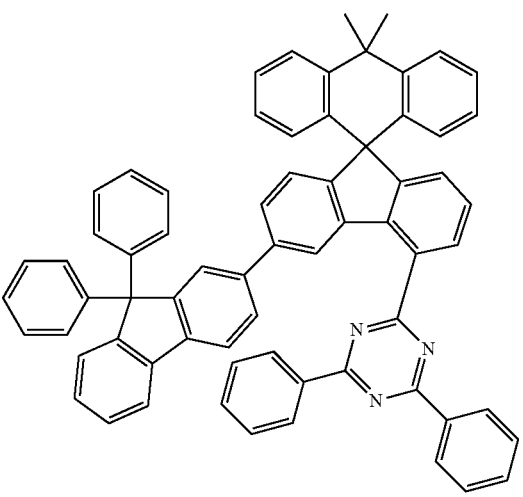

111
-continued
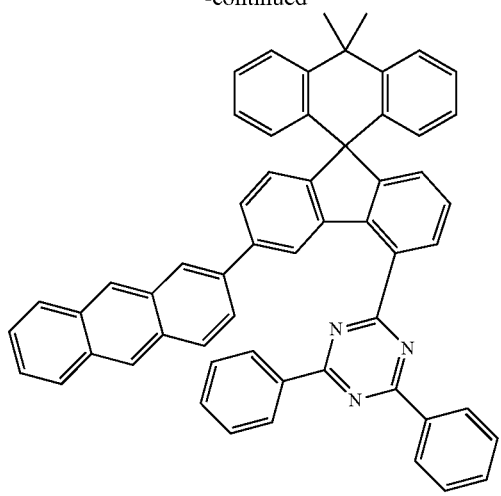
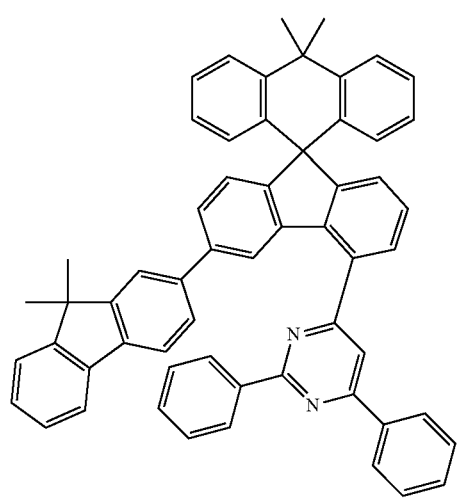
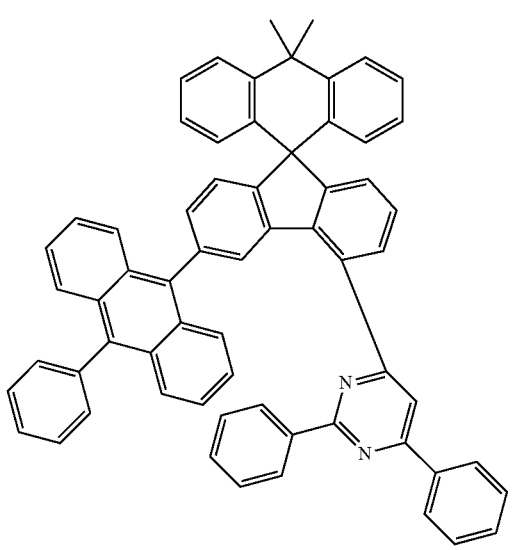
112
-continued
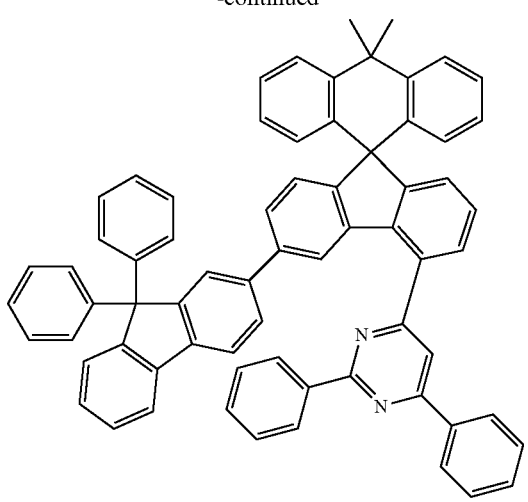
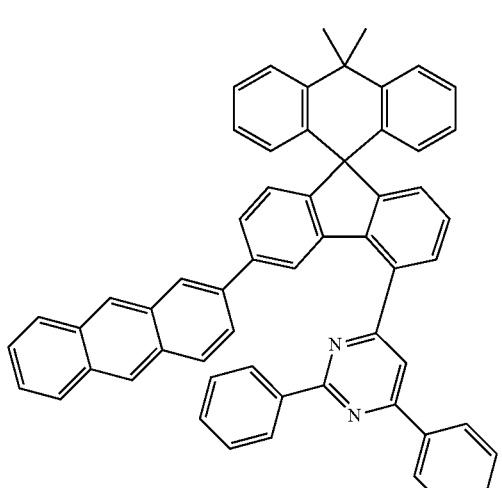
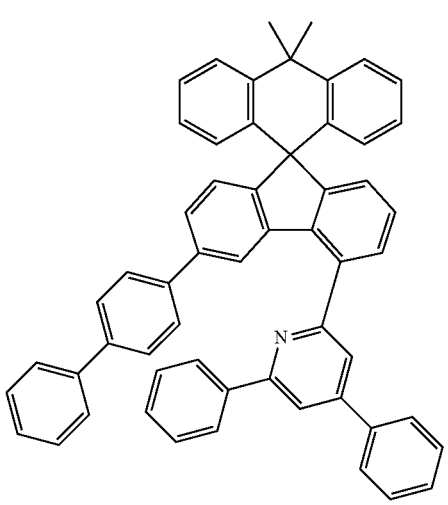

113
-continued
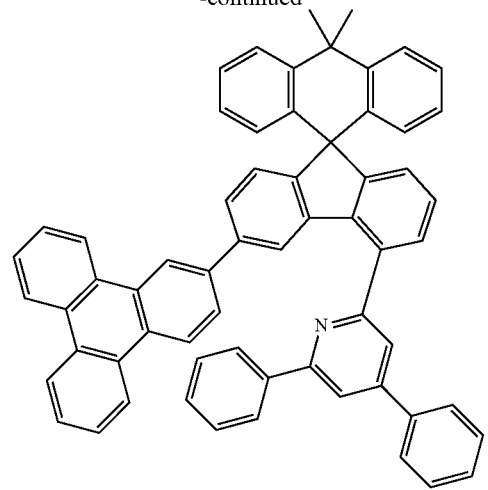
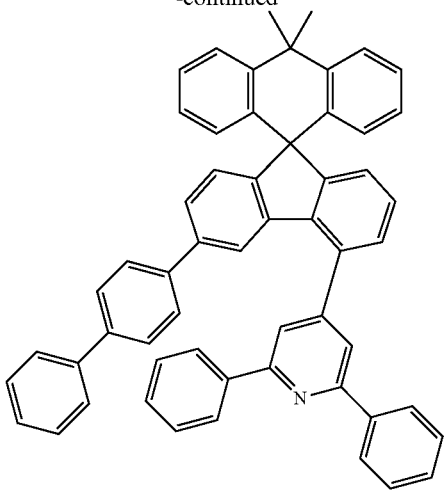
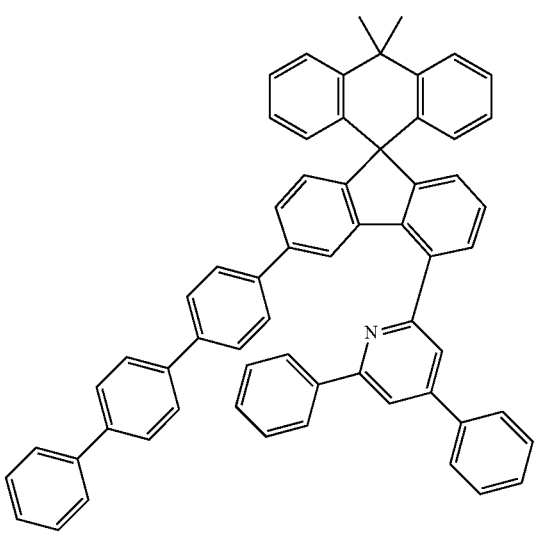
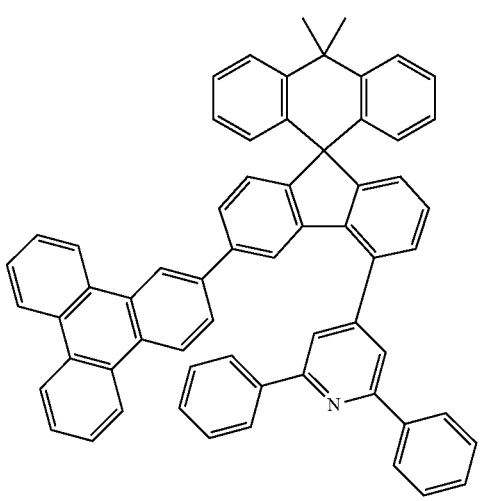
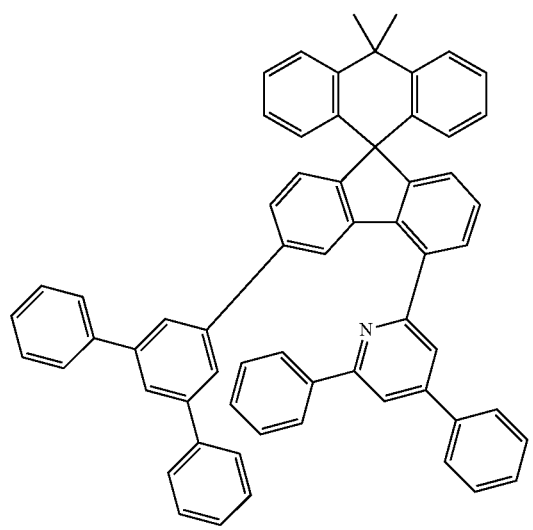
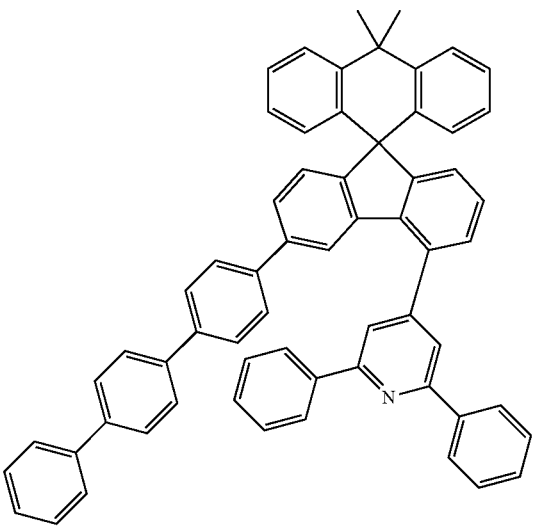
114
-continued 115
-continued
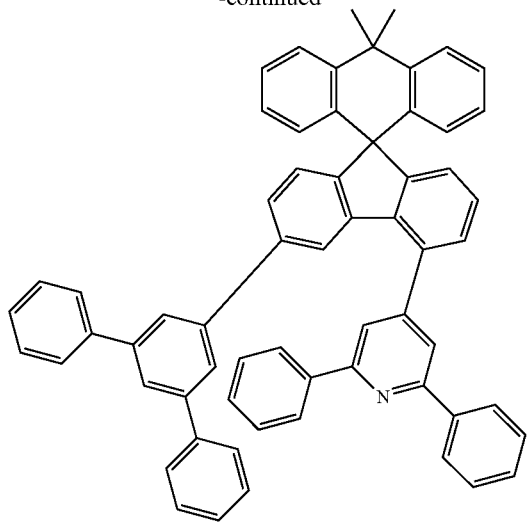
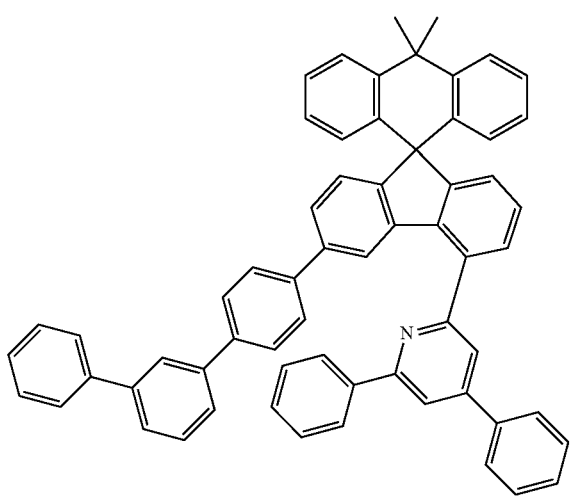
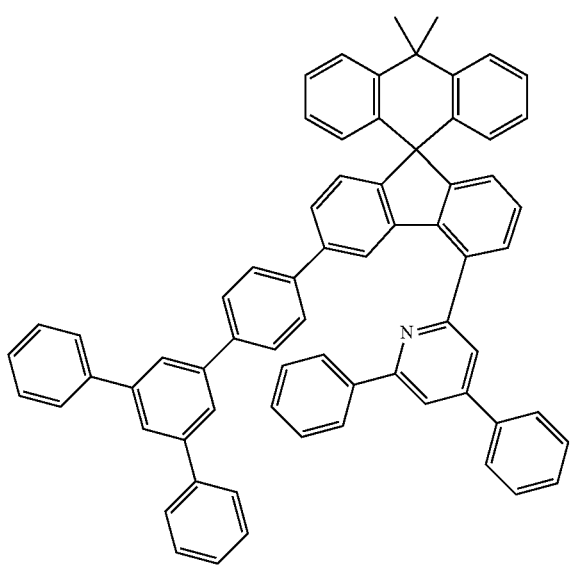
116
-continued
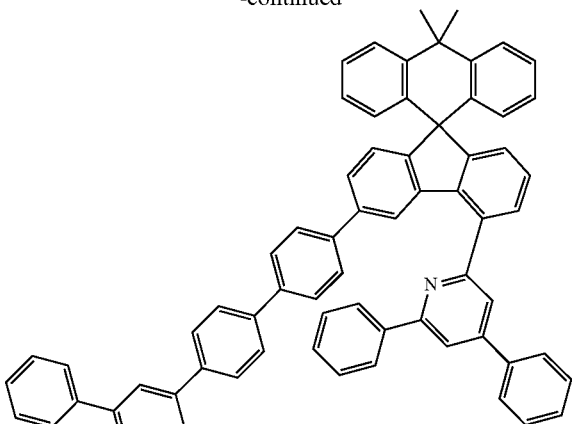
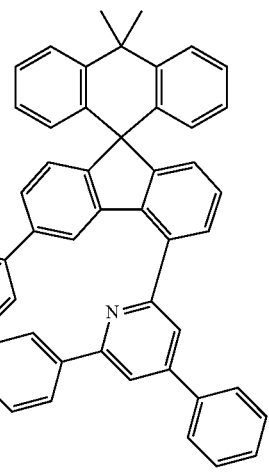
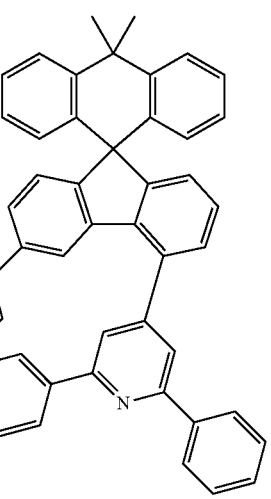

117
-continued
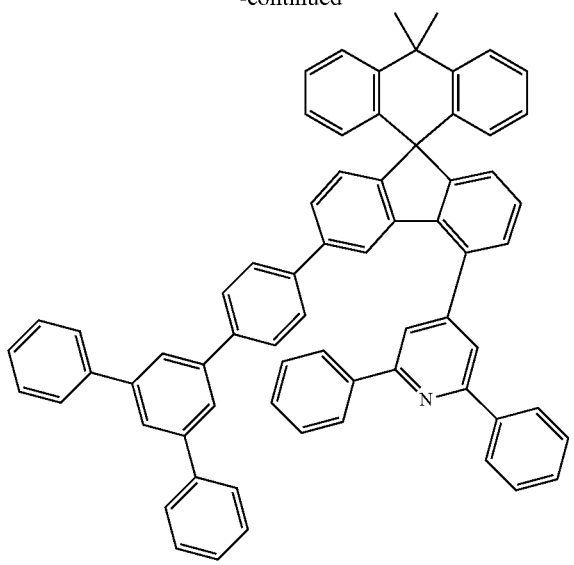
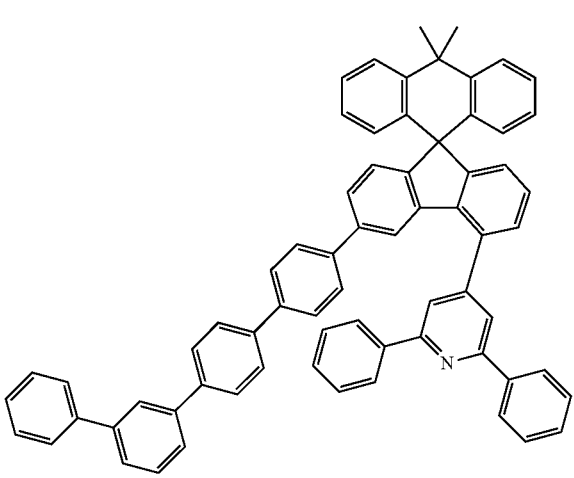
118
-continued
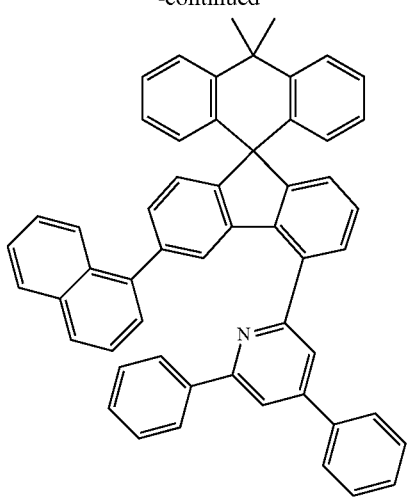
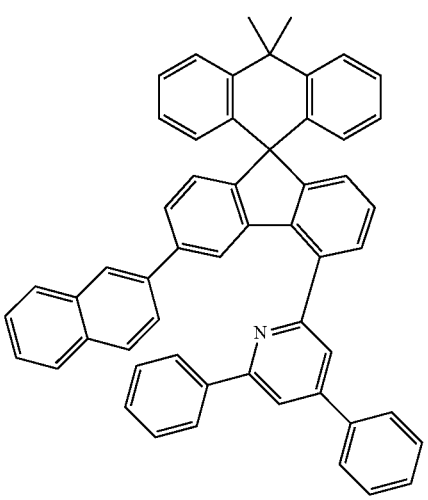
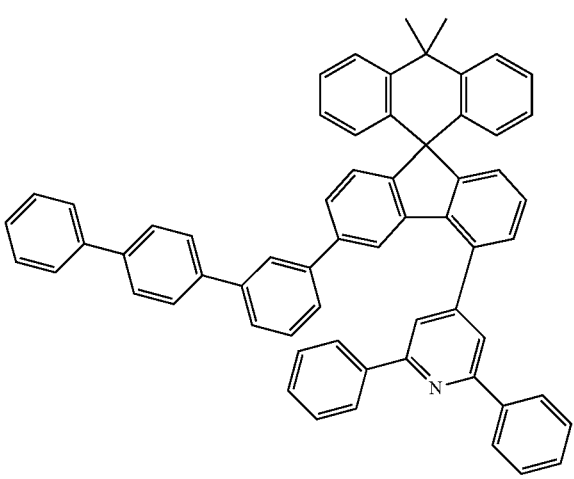
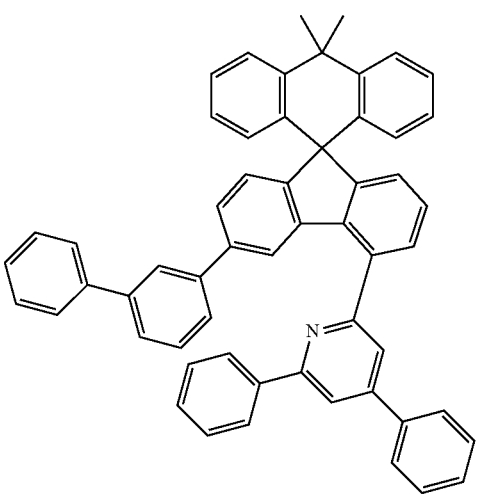

119
-continued
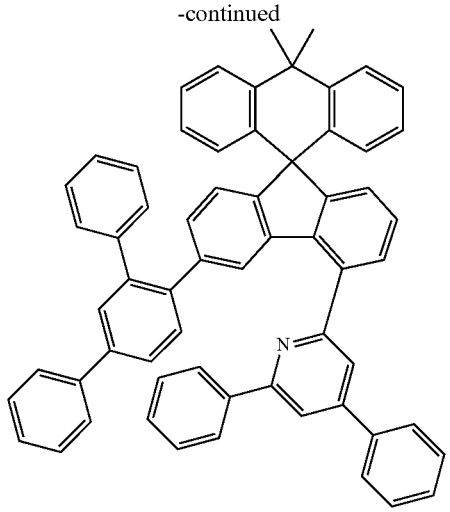
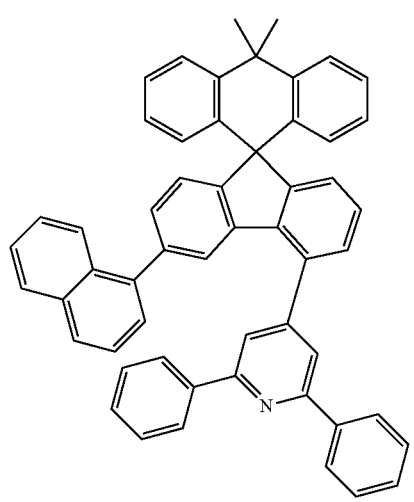
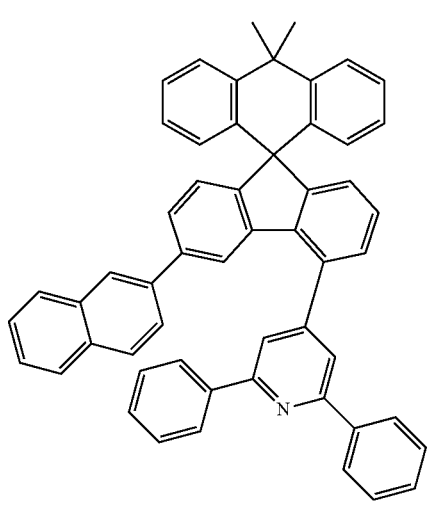
120
-continued
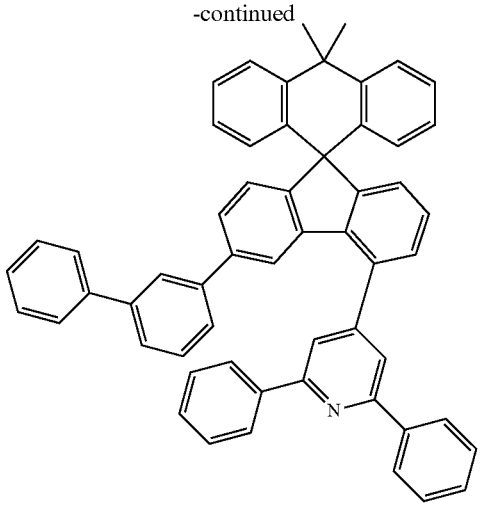
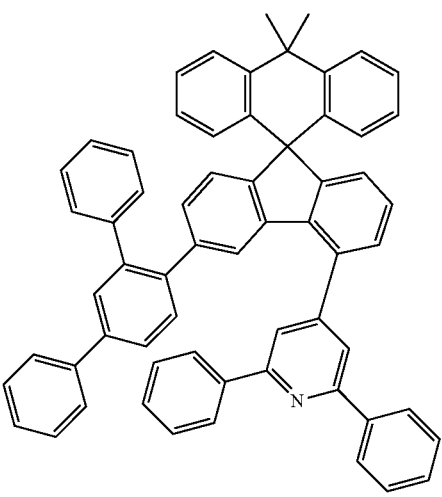
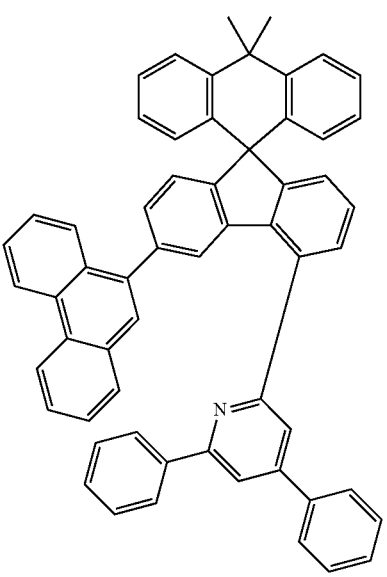

121
-continued
122
-continued
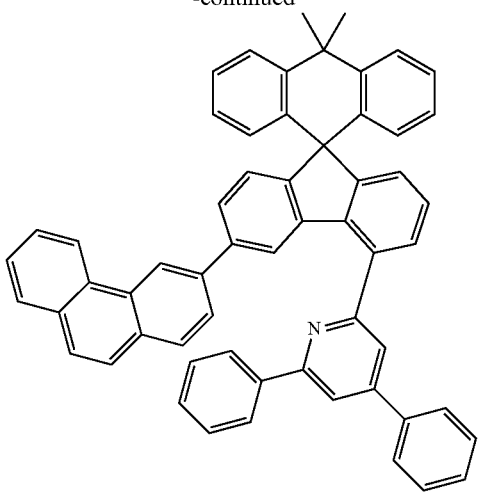
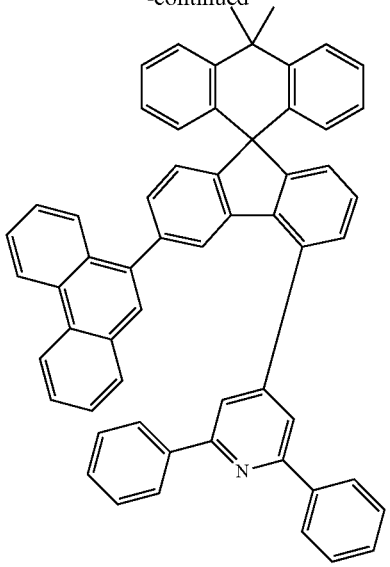
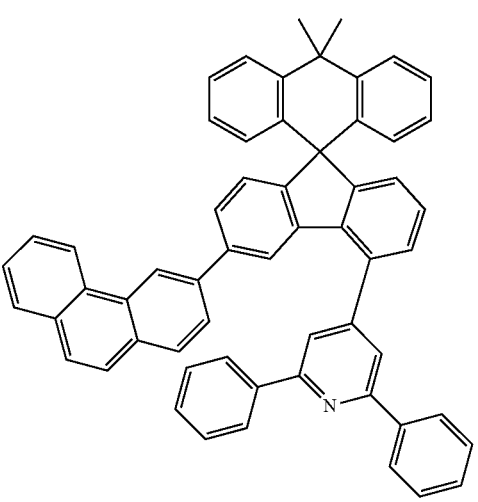
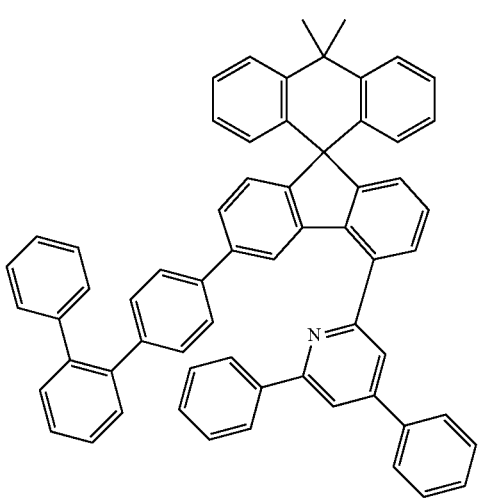

123
-continued
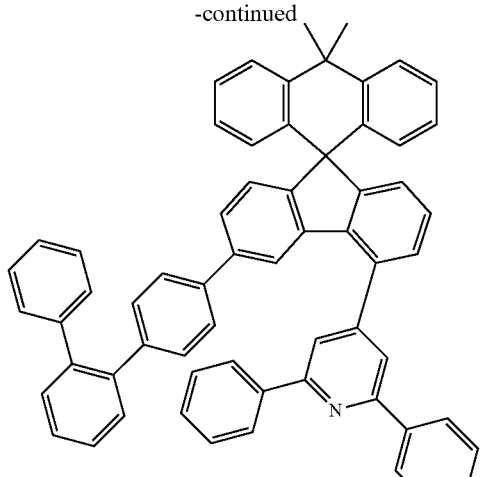
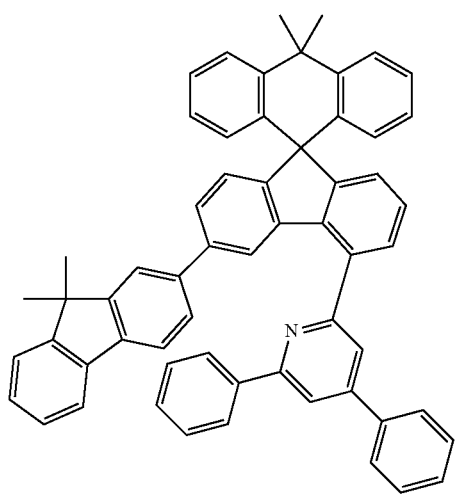
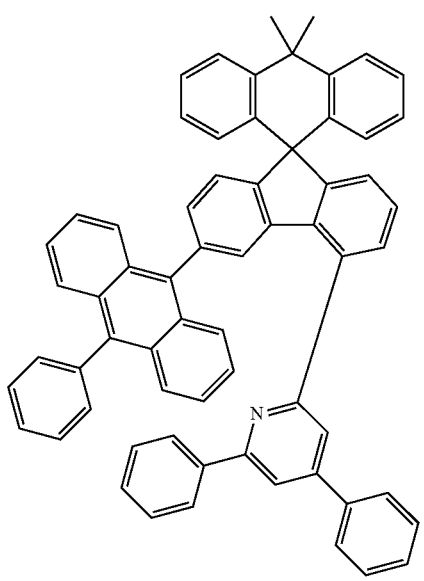
124
-continued
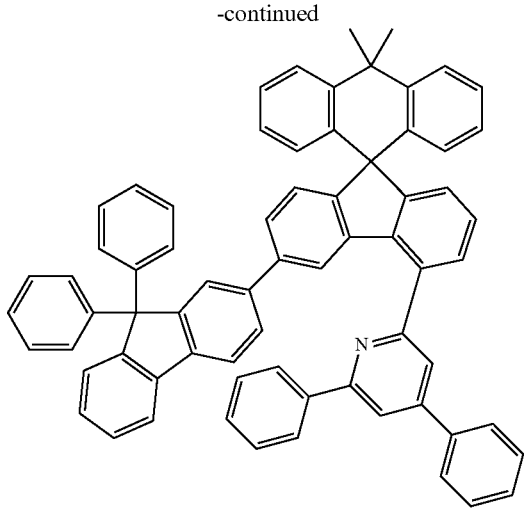
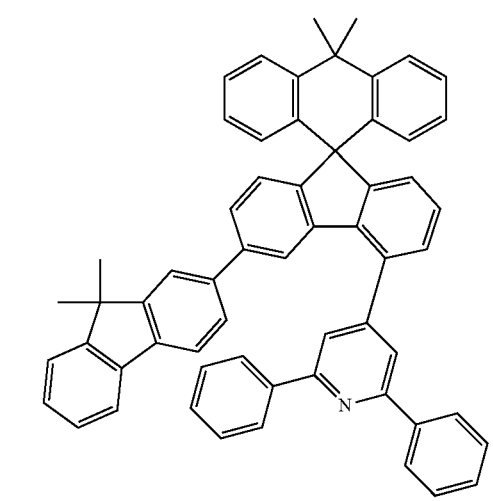

125
-continued
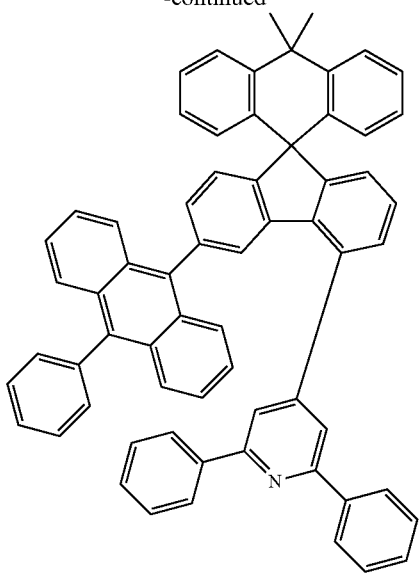
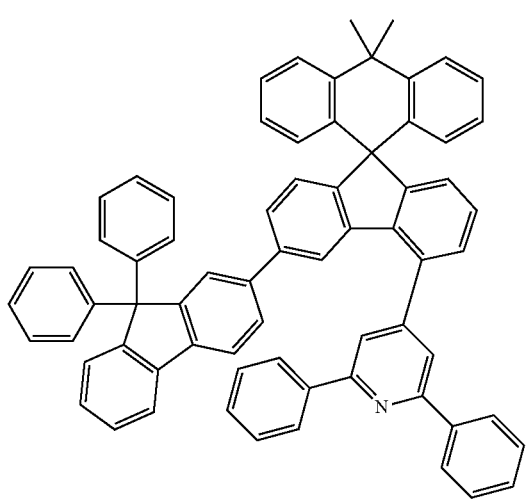
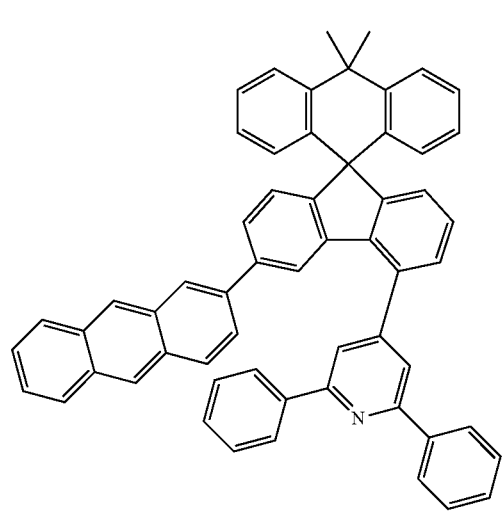
126
-continued
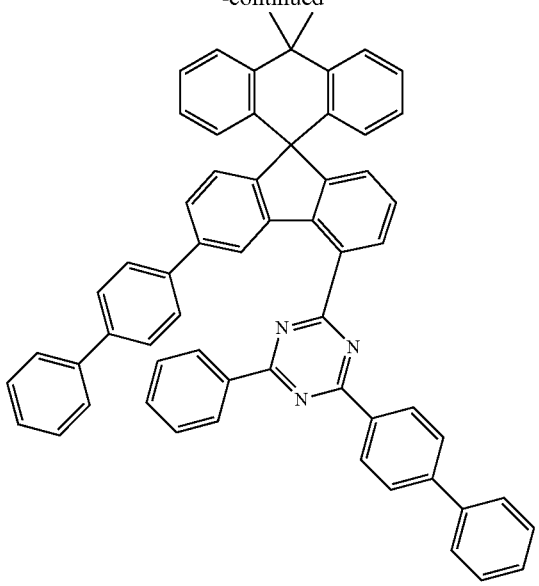
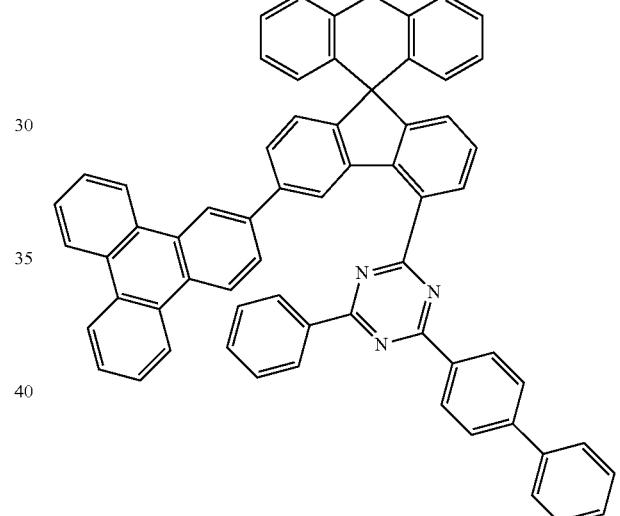
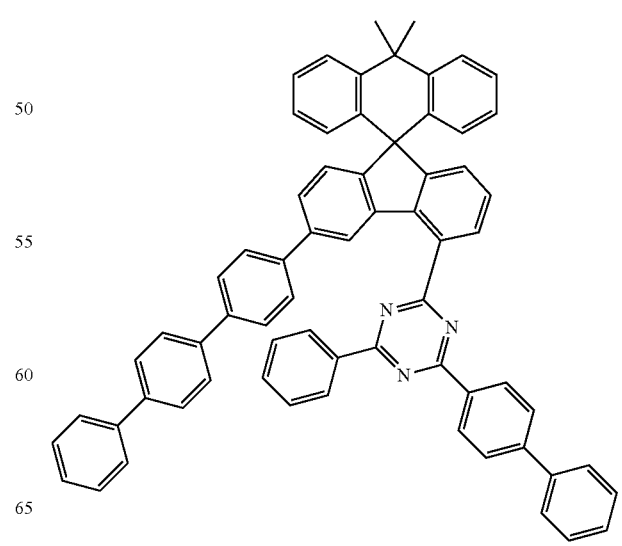

127
-continued
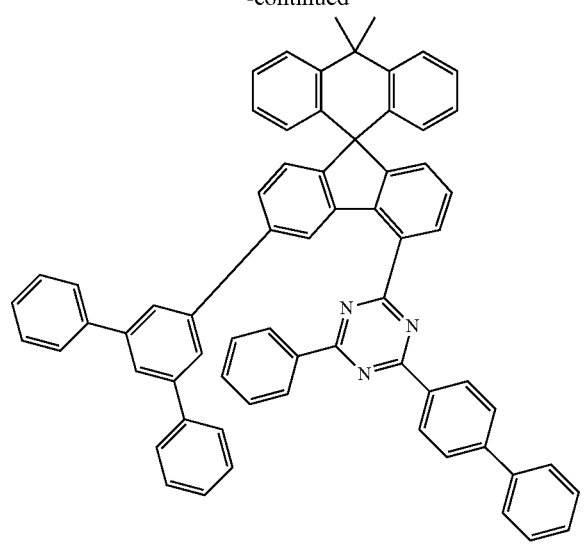
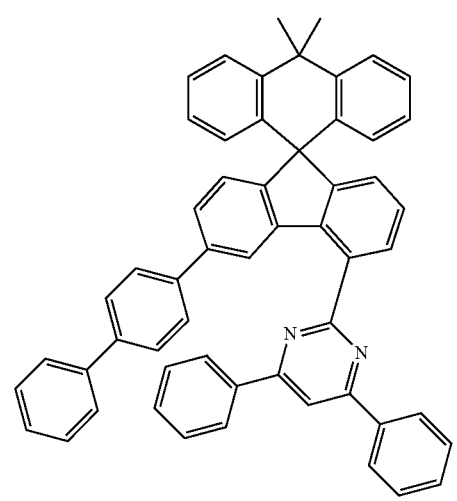
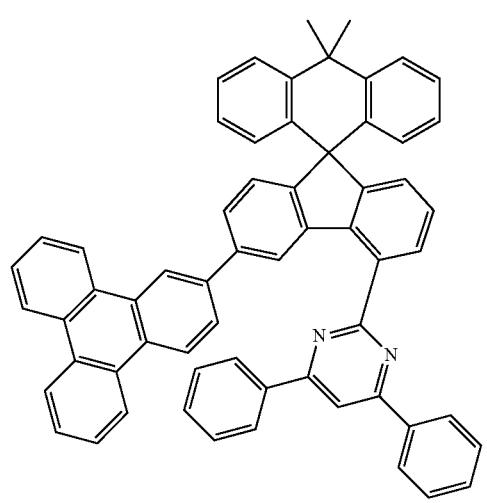
128
-continued
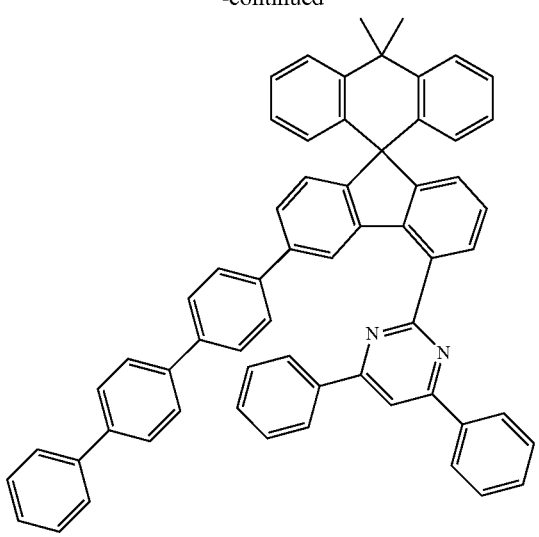
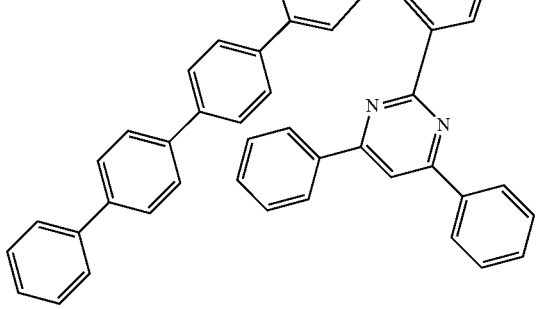
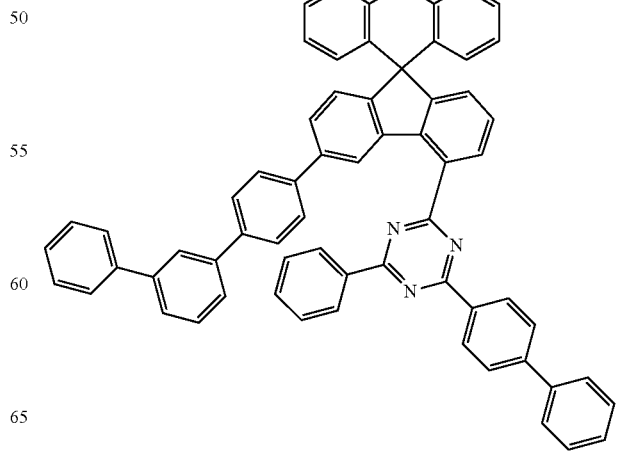

129
-continued
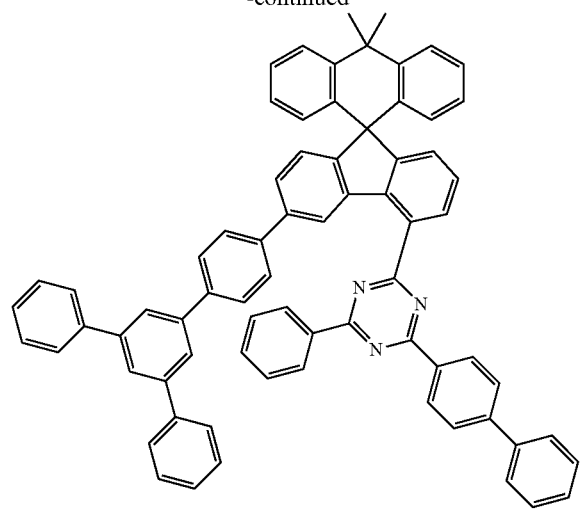
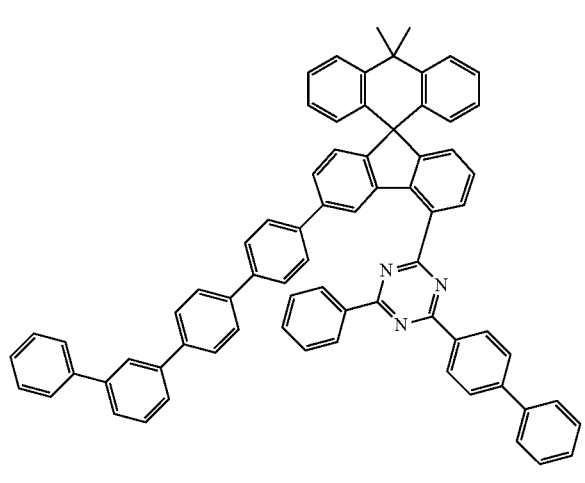
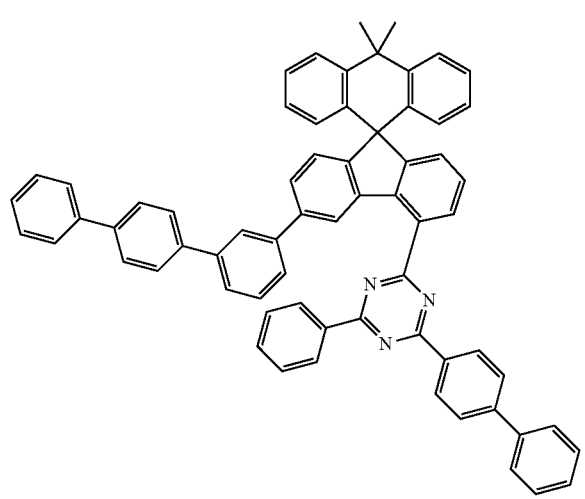
130
-continued
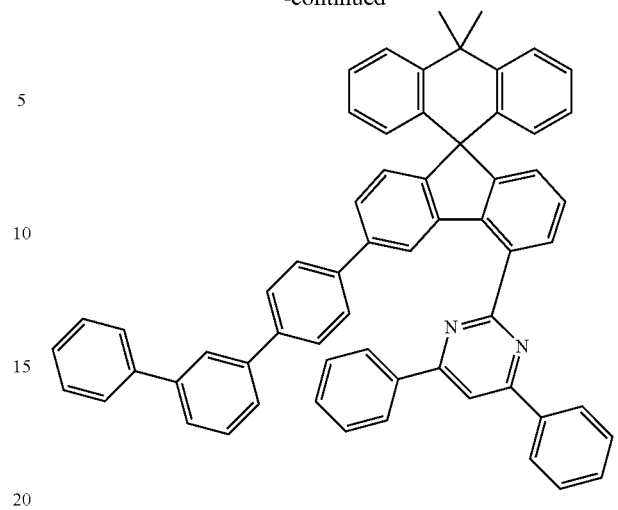
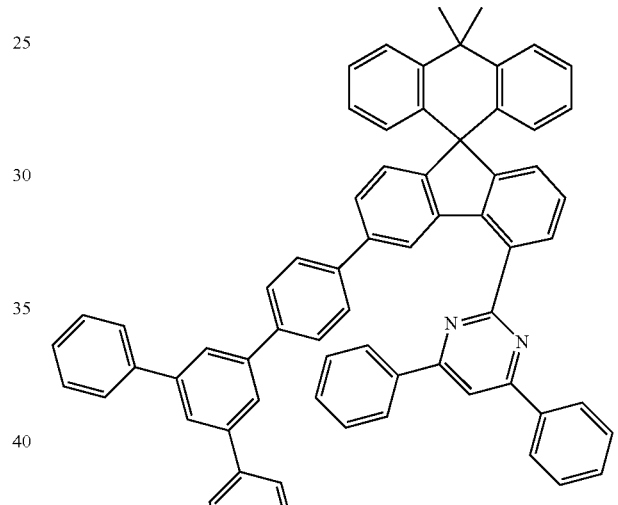
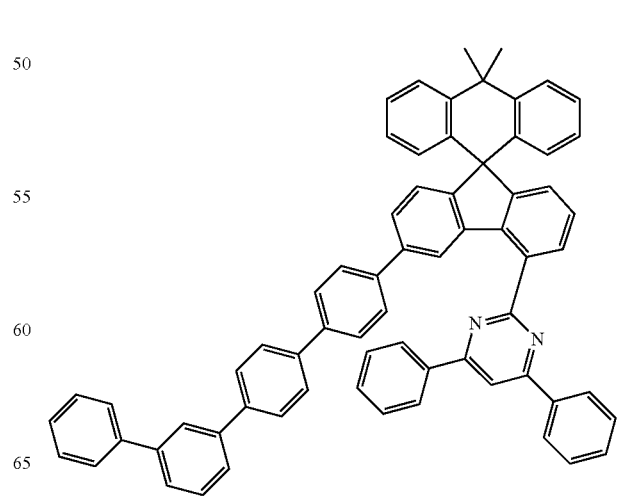

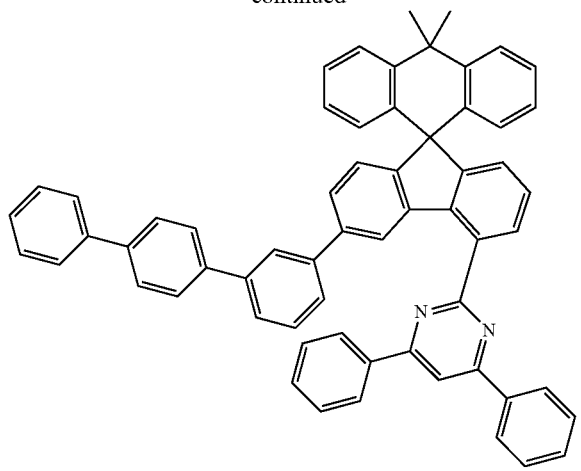
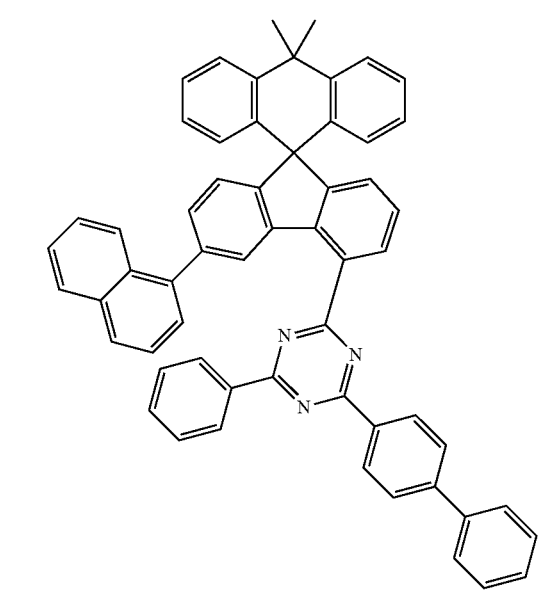
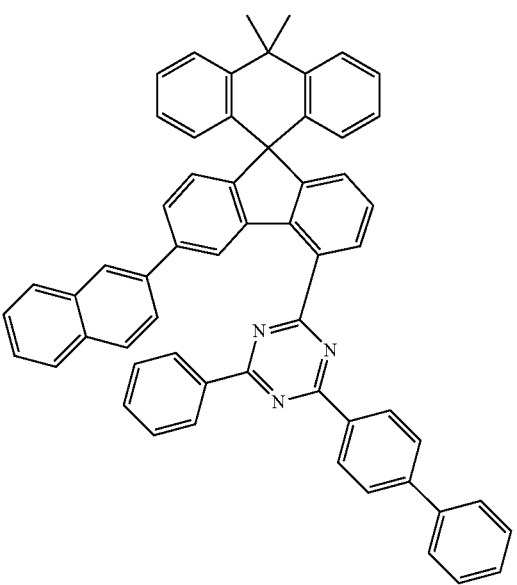
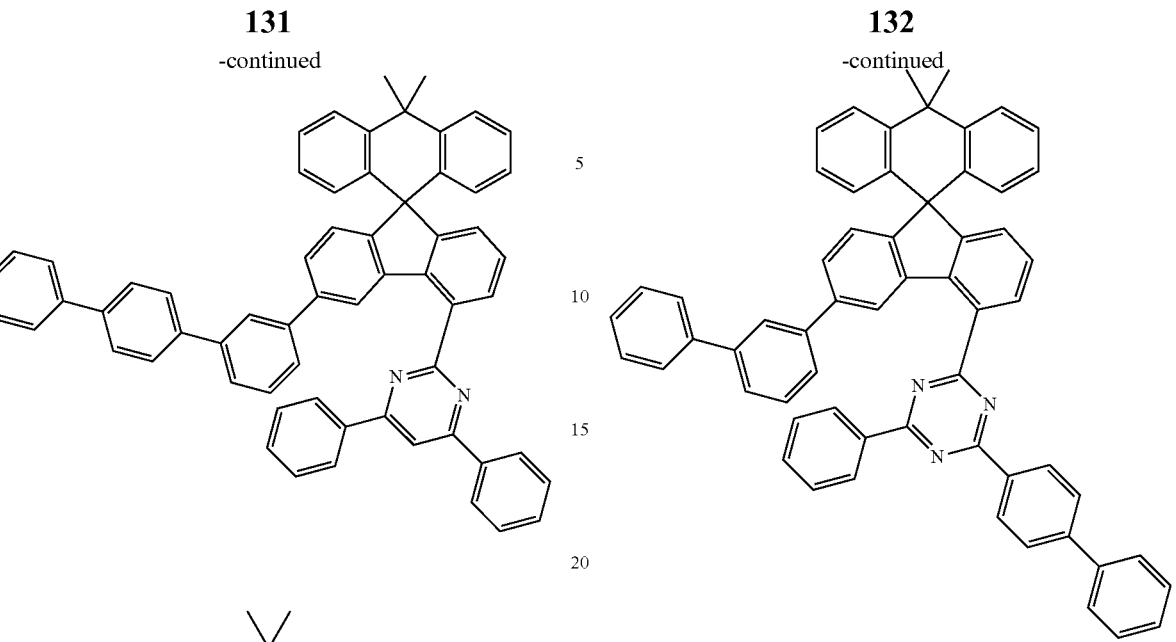
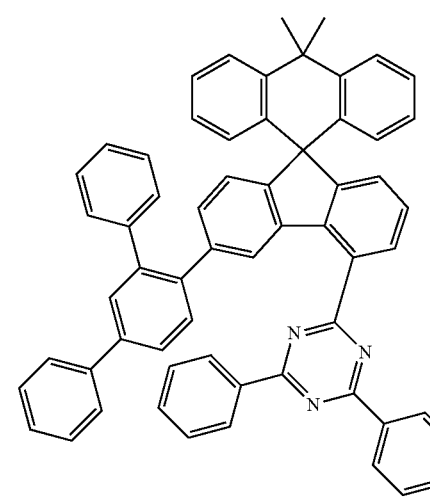
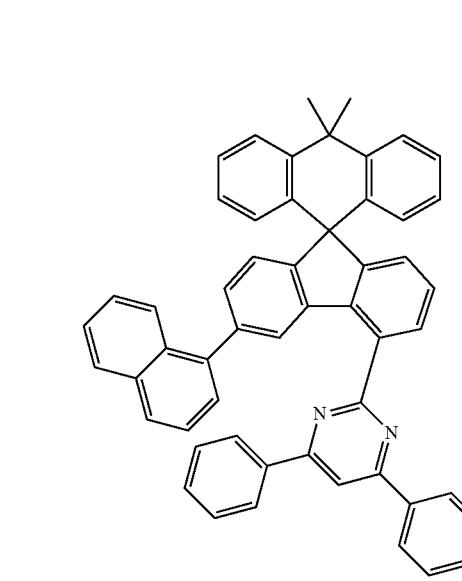

133
-continued
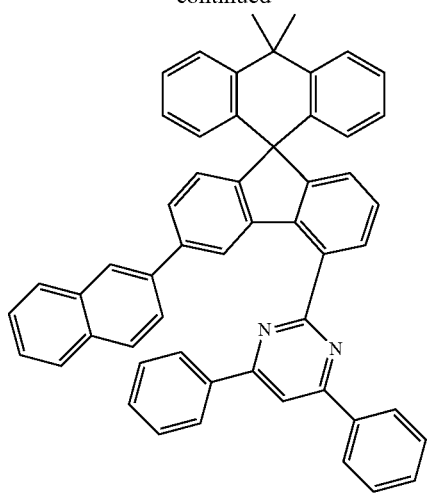
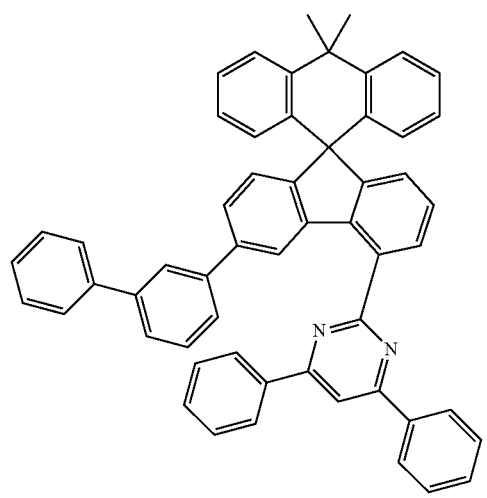
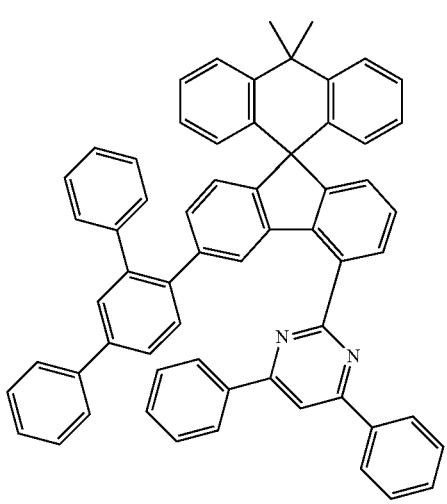
134
-continued
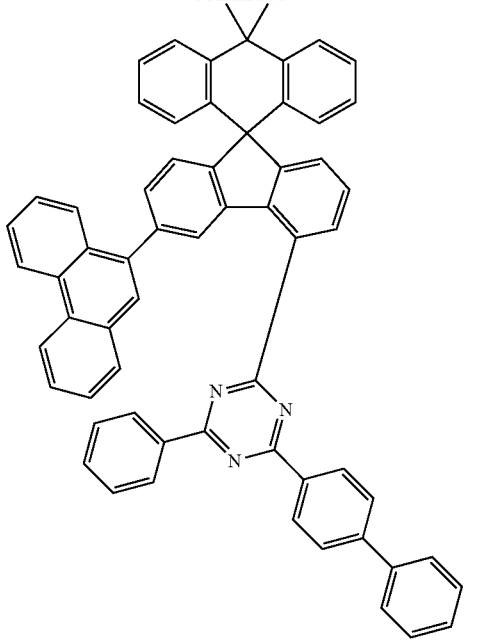
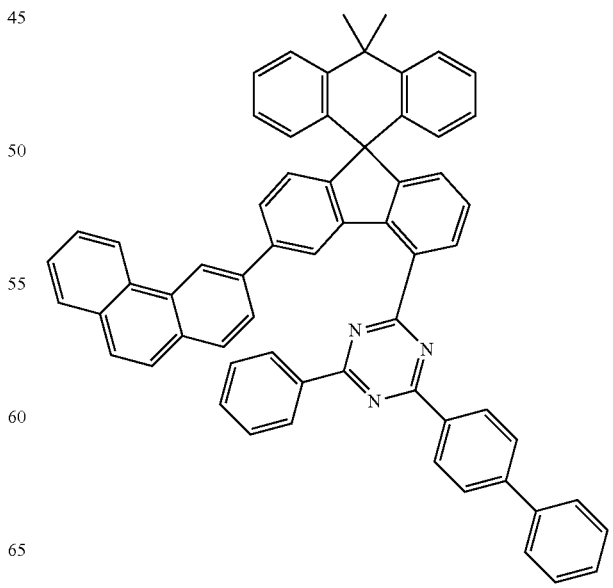

135
-continued
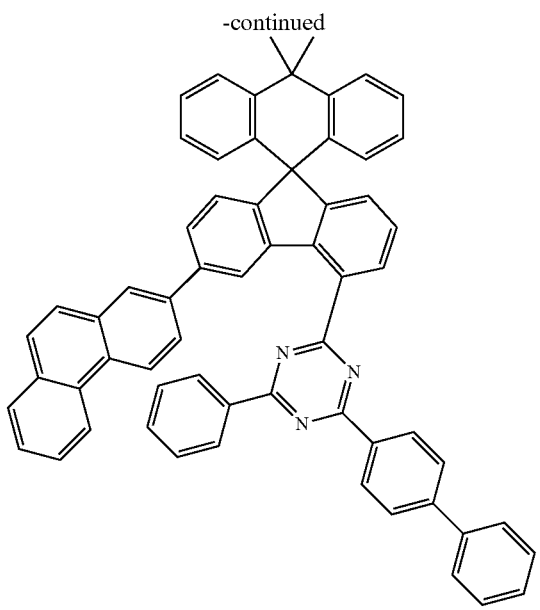
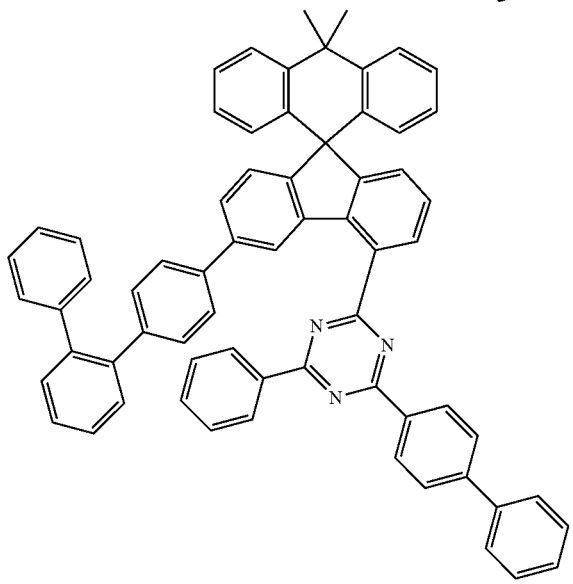
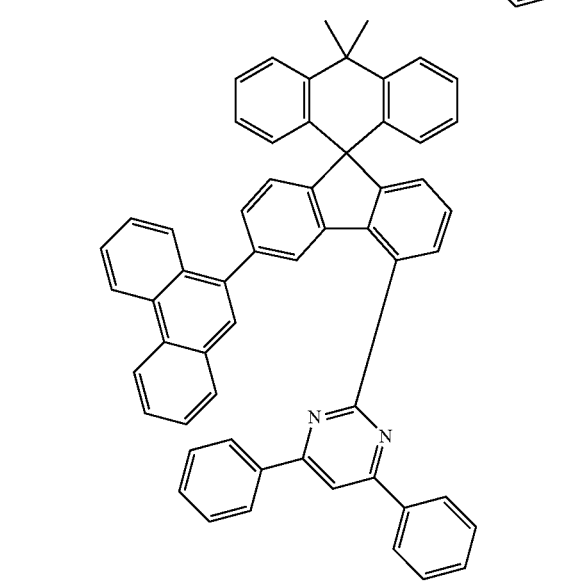
136
-continued
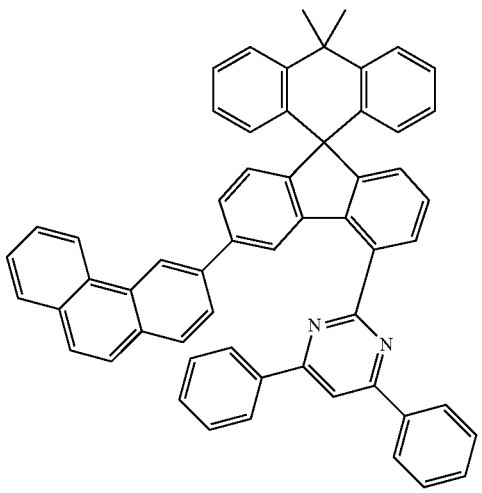
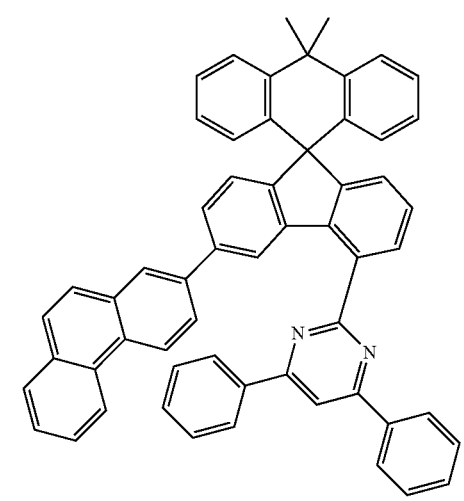
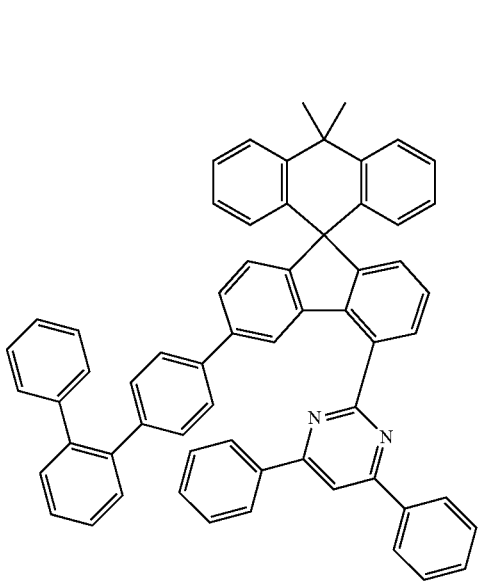

137
-continued
138
-continued
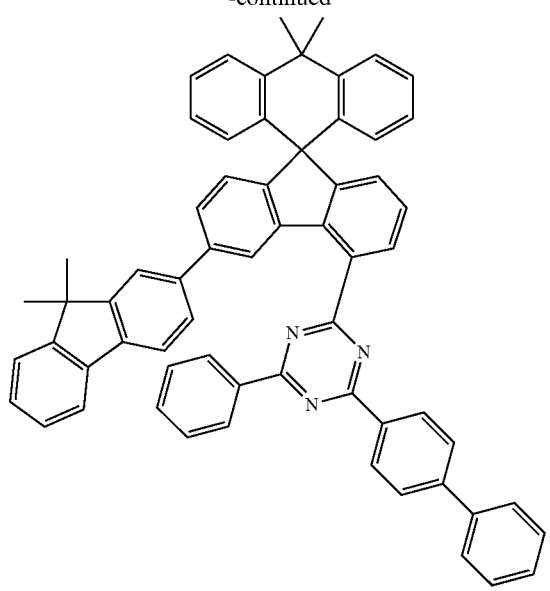
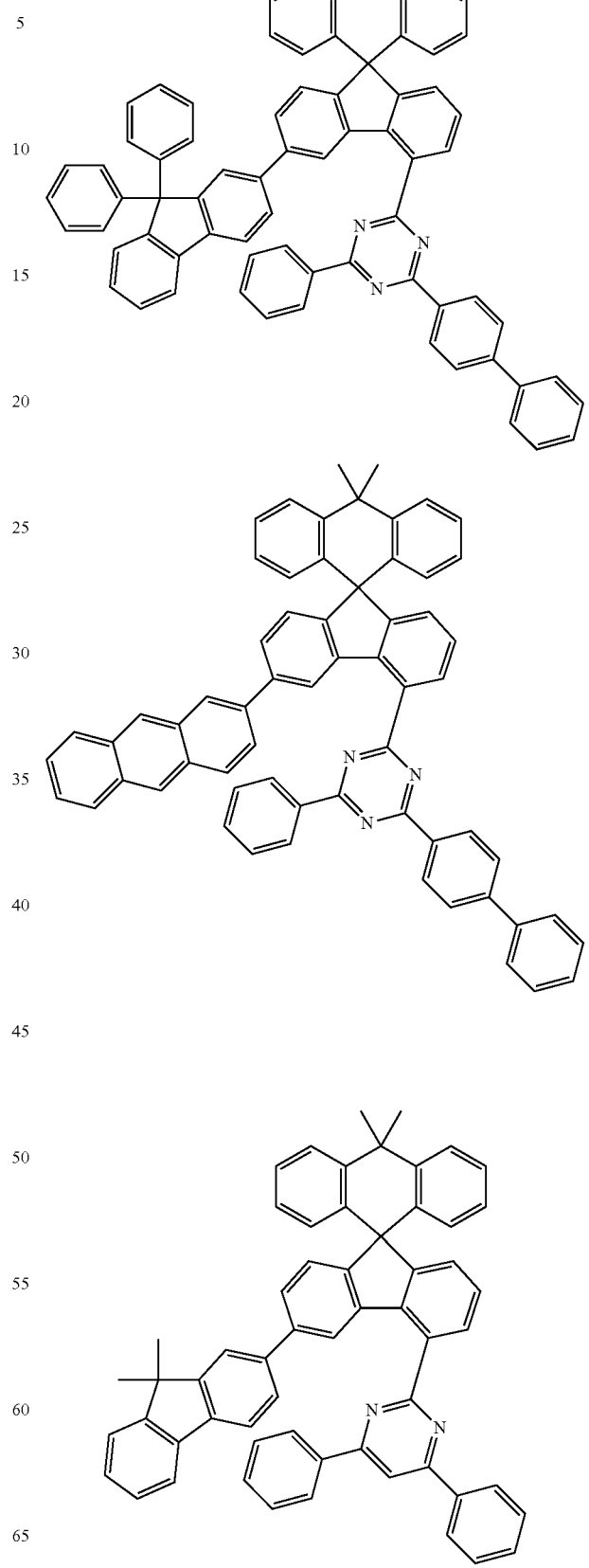

139
-continued
140
-continued
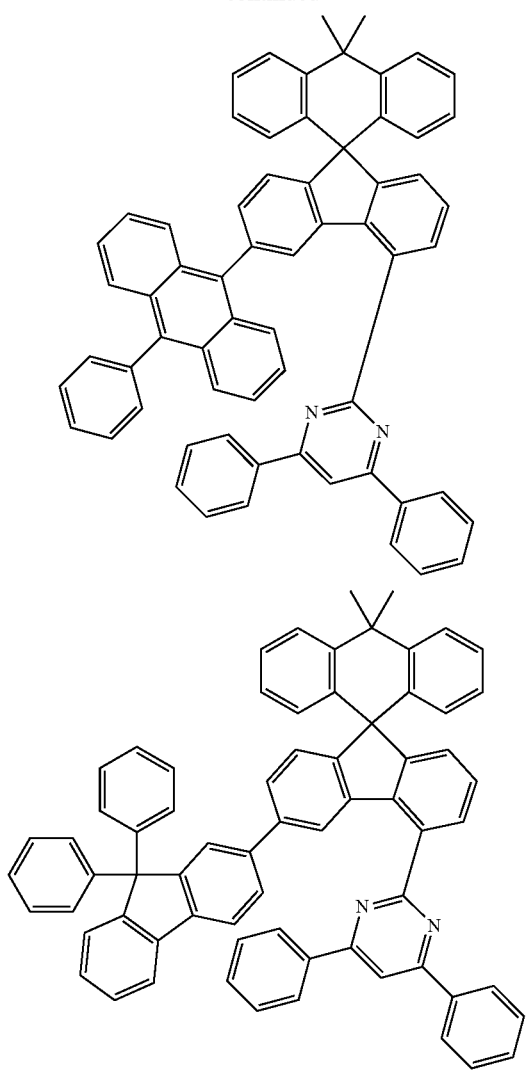
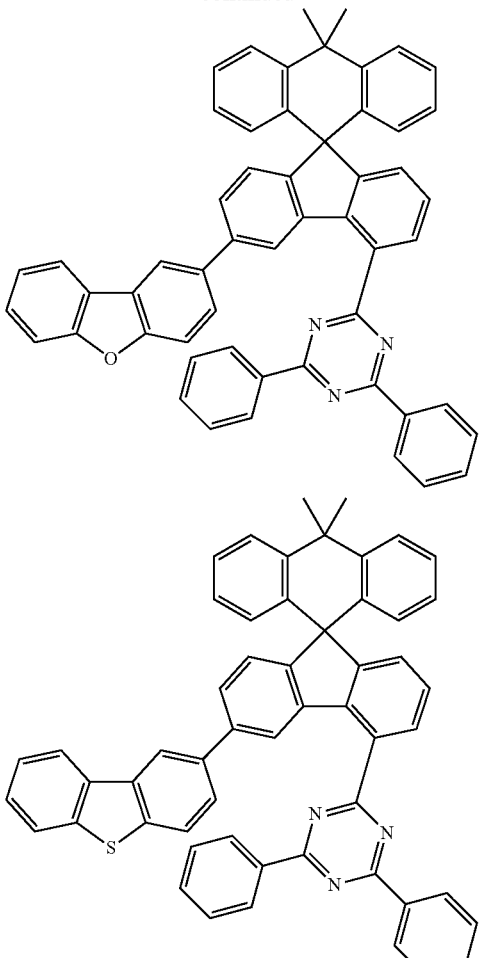
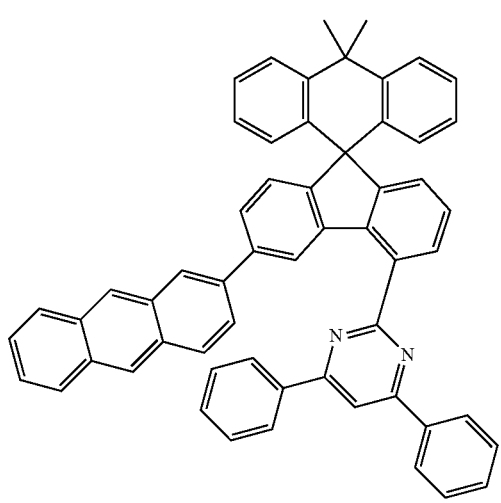
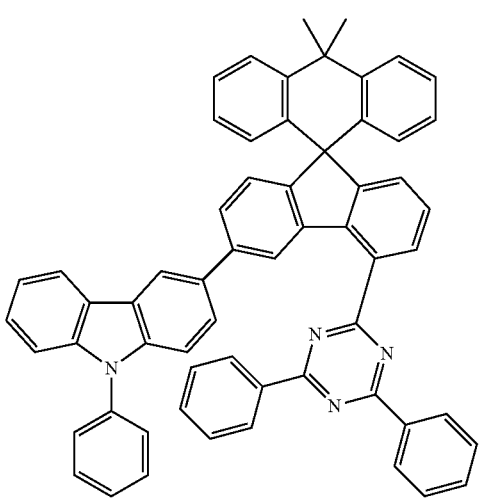

141
-continued
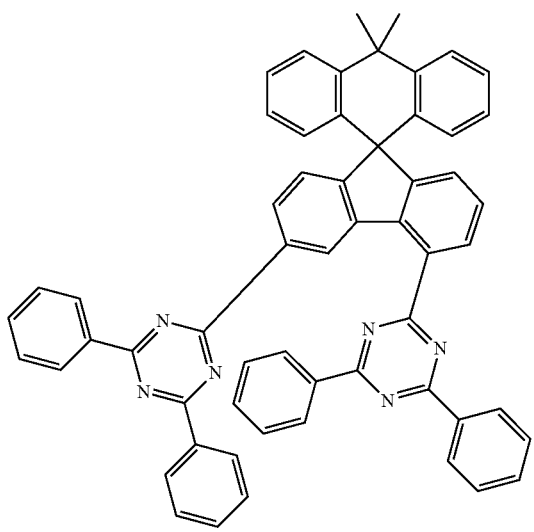
142
-continued
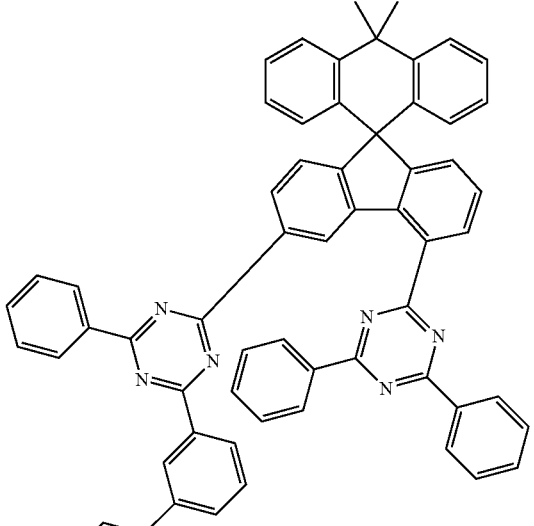
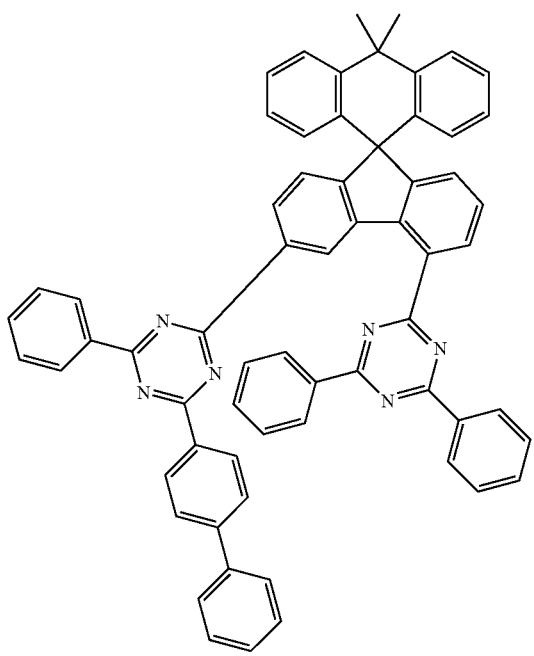
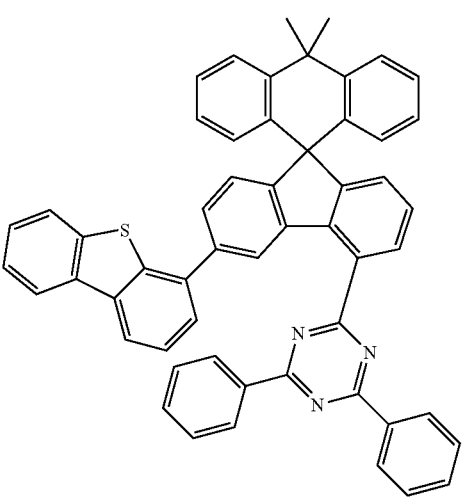

143
-continued
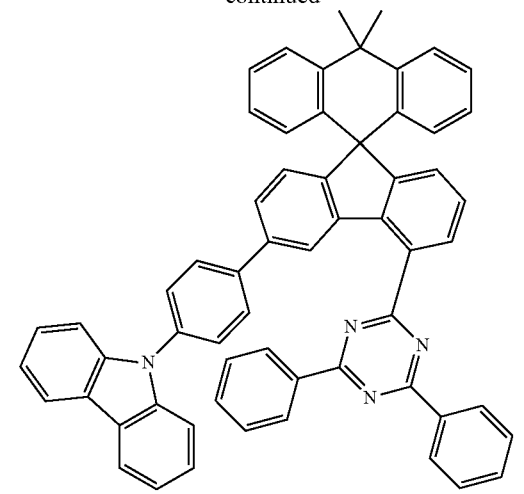
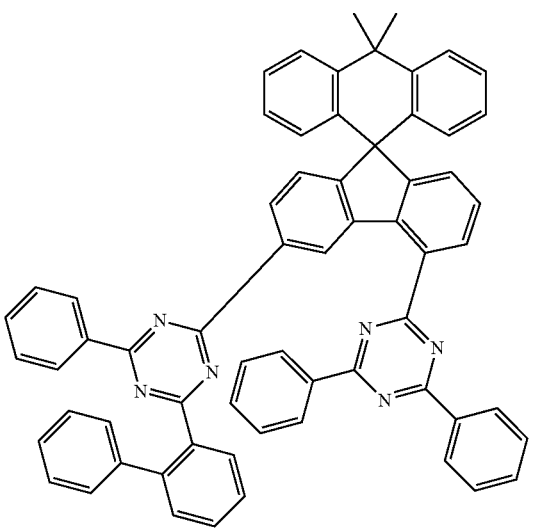
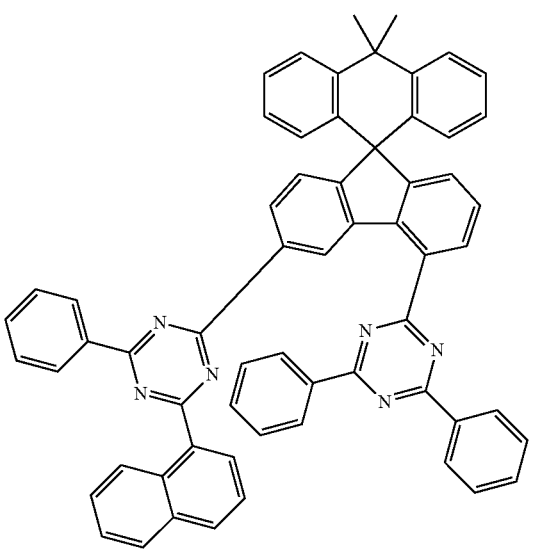
144
-continued
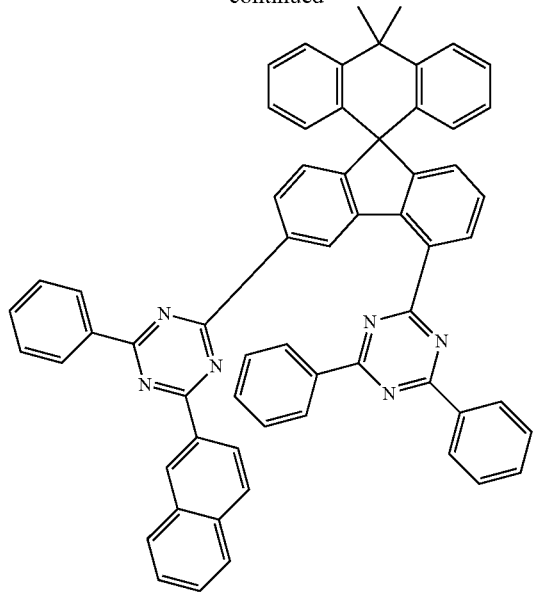
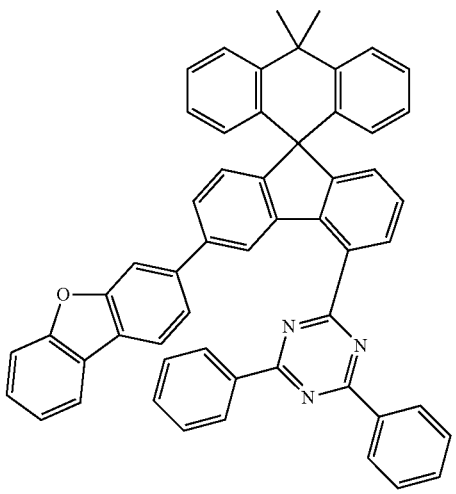
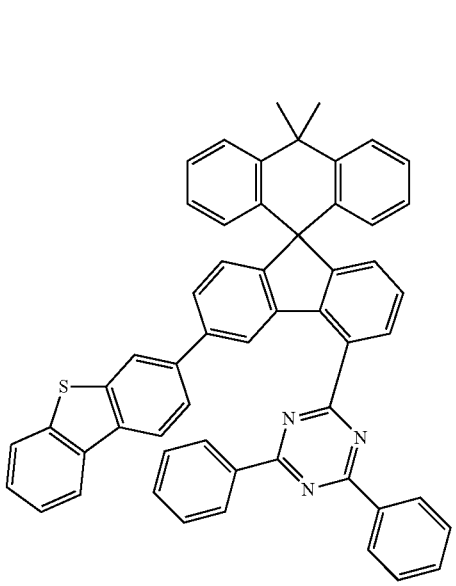

145
-continued
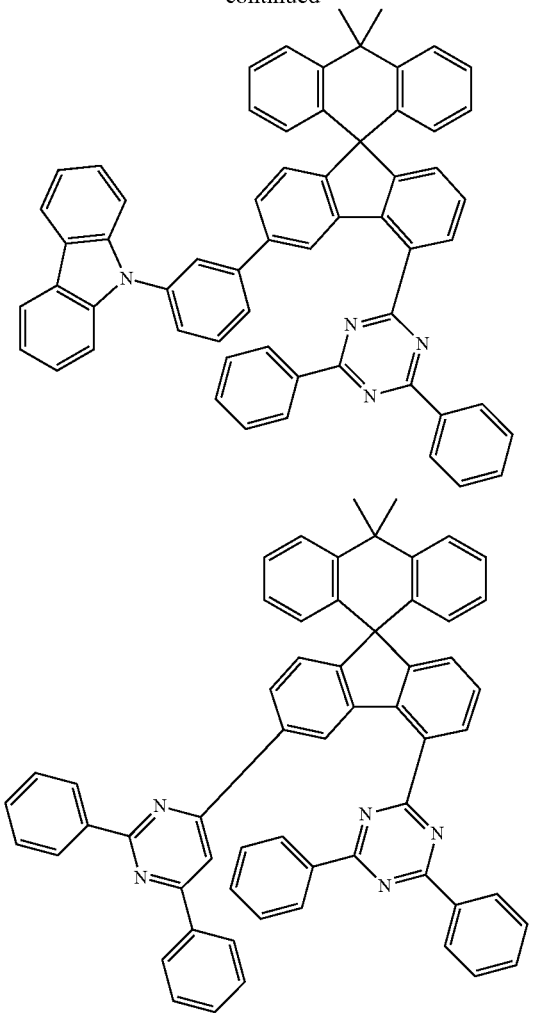
146
-continued
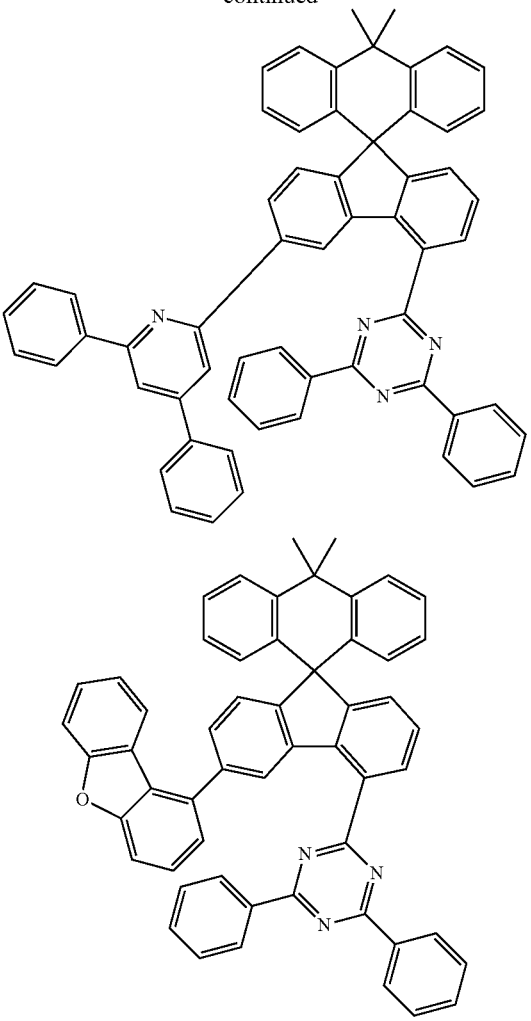
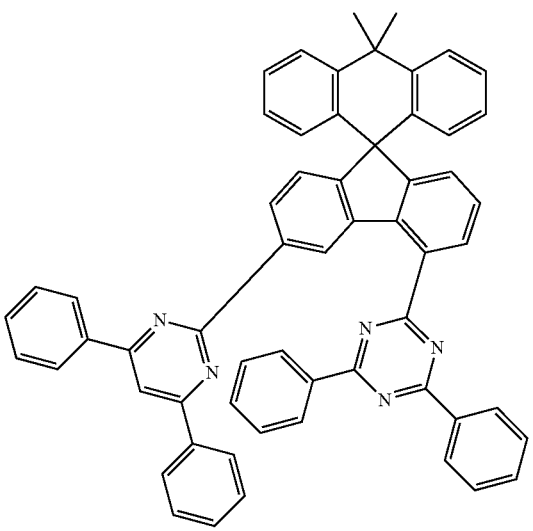
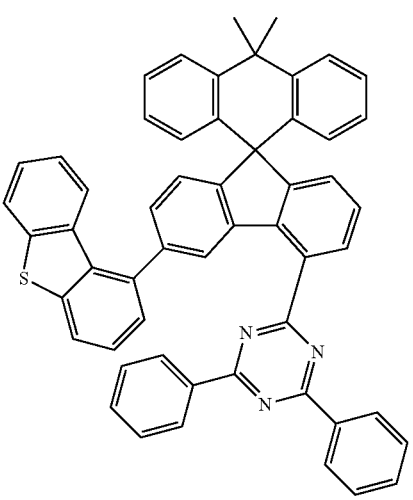

147
-continued
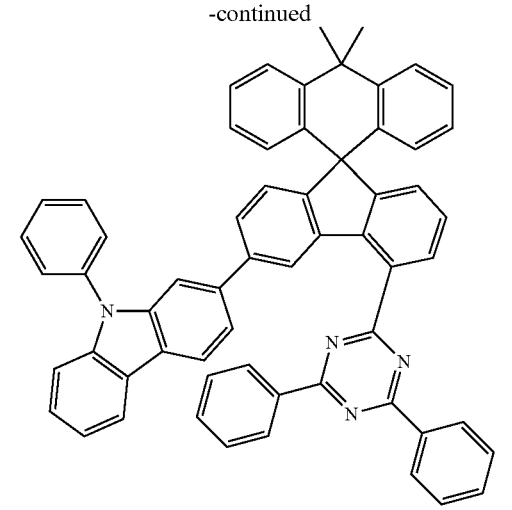
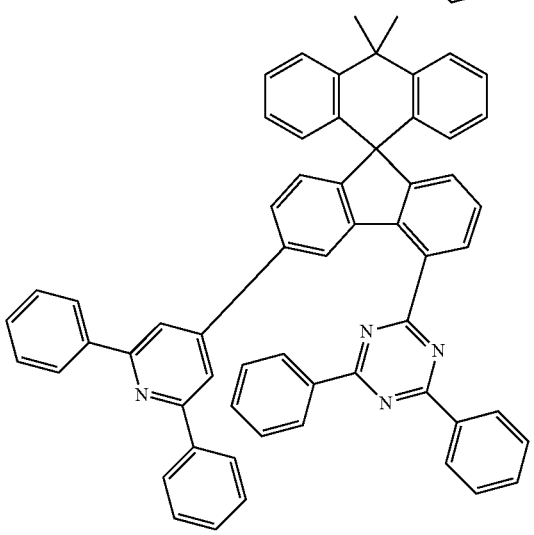
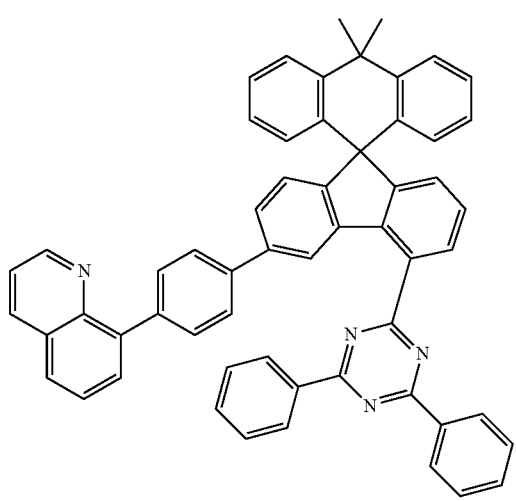
148
-continued
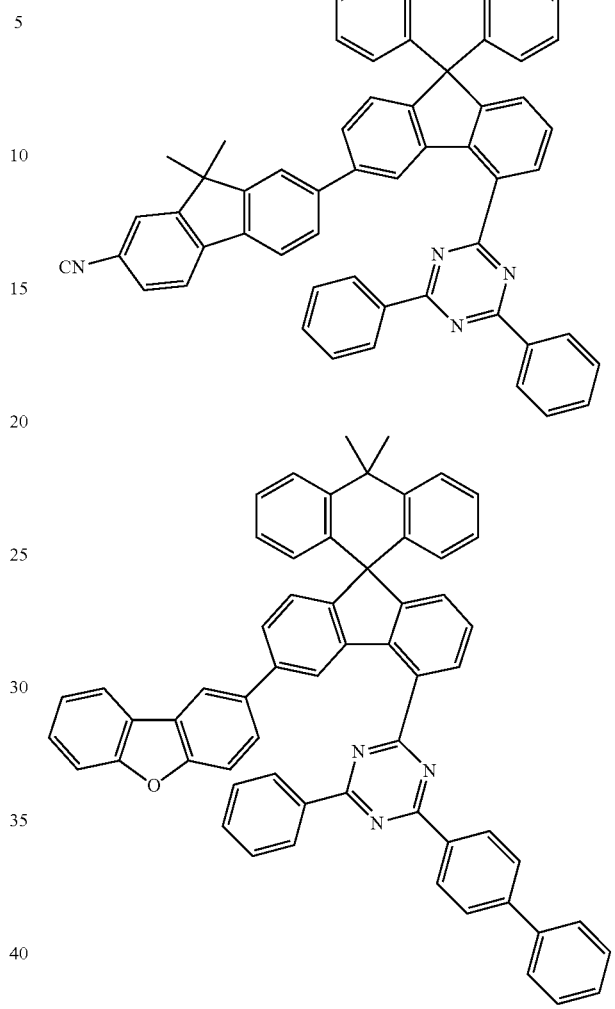
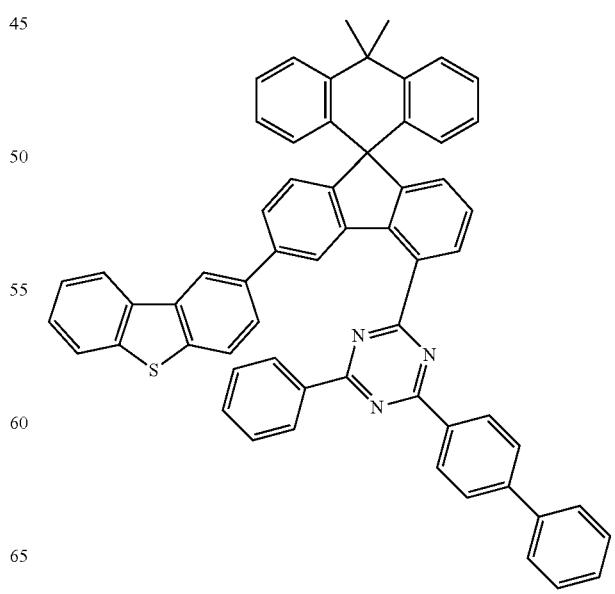

149
-continued
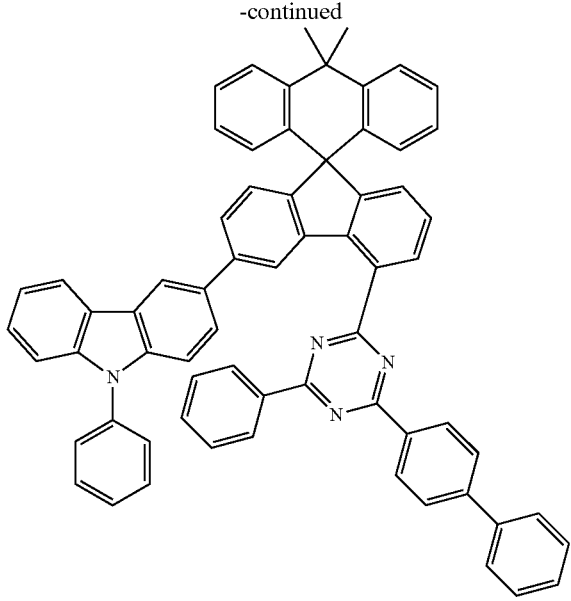
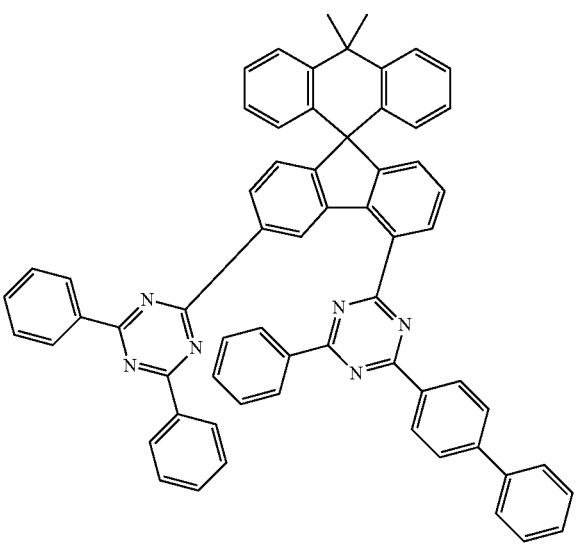
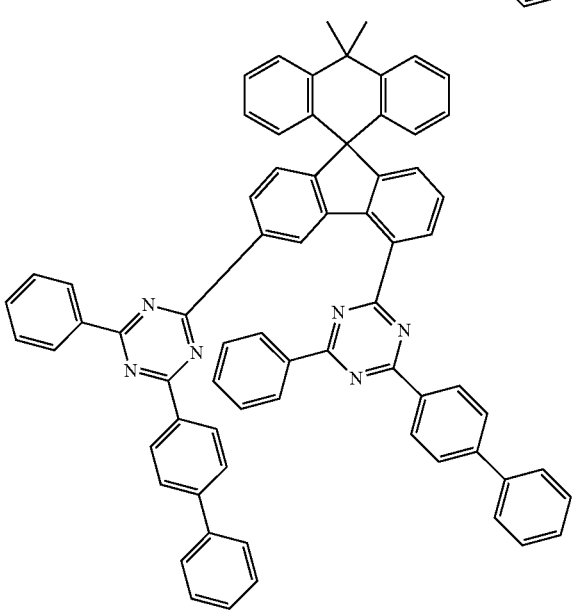
150
-continued
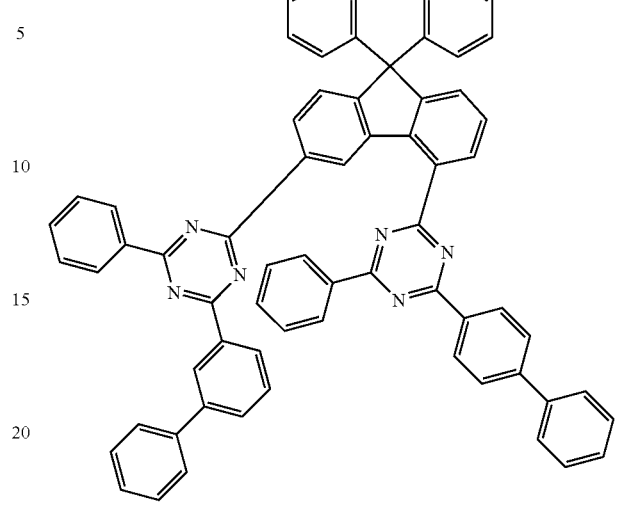
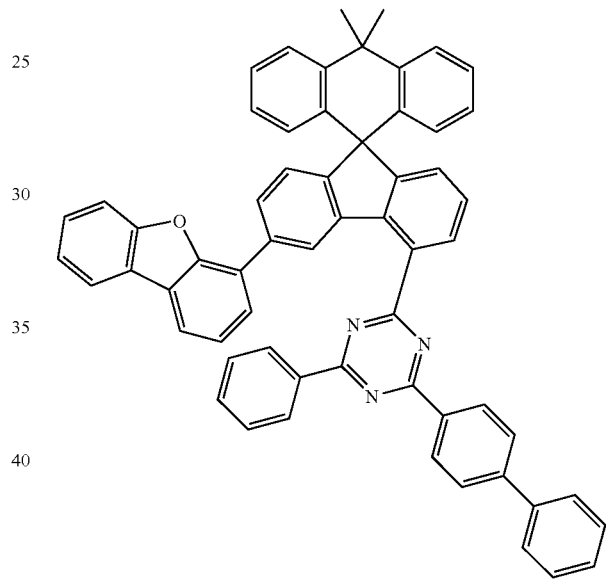
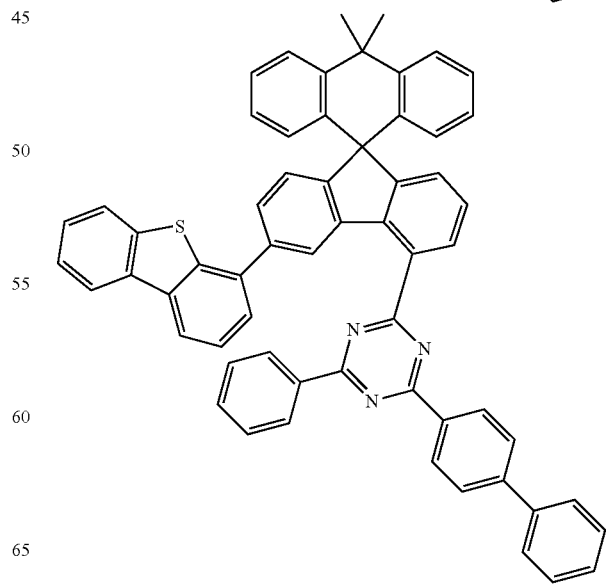

151                                                                   152
-continued                                                       -continued 153
-continued
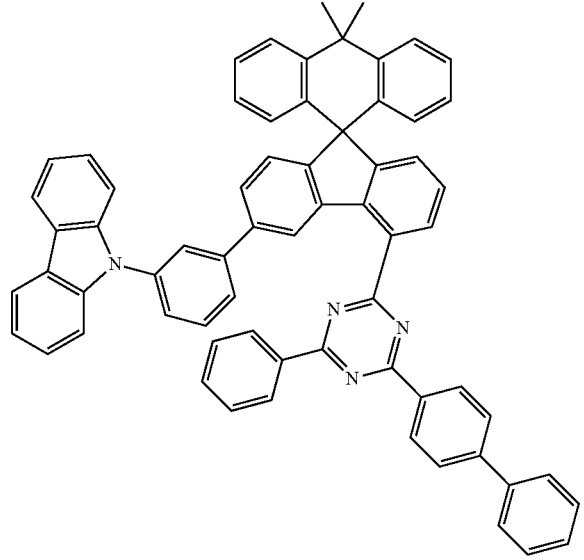
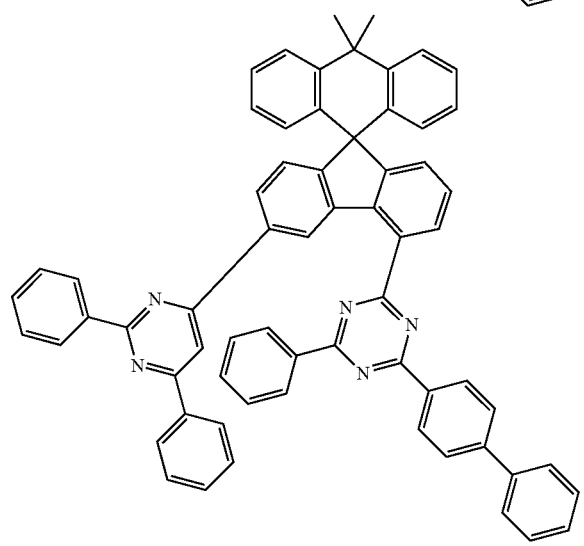
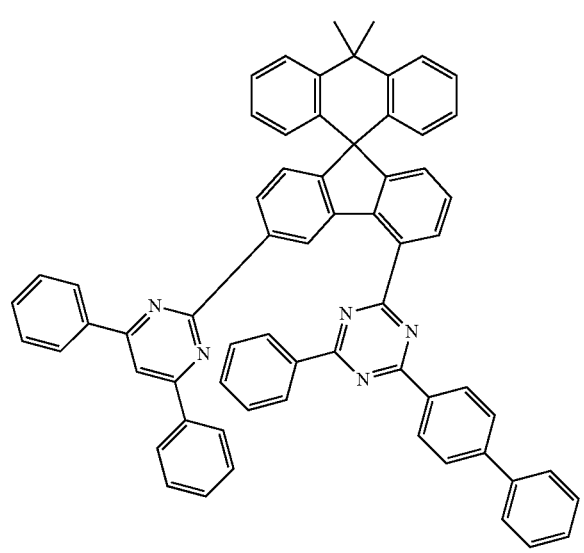
154
-continued
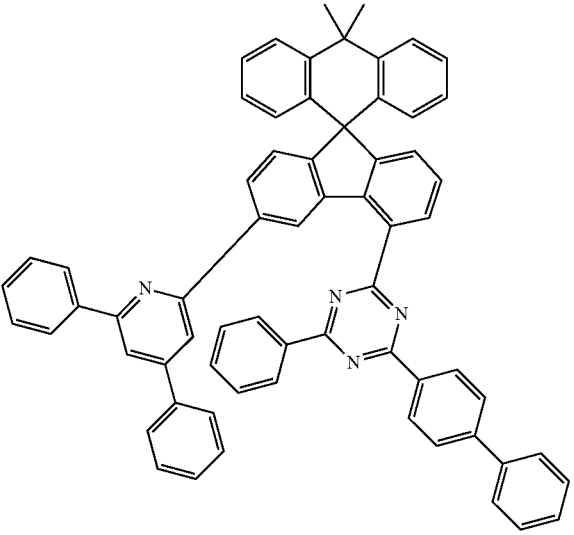

155
-continued
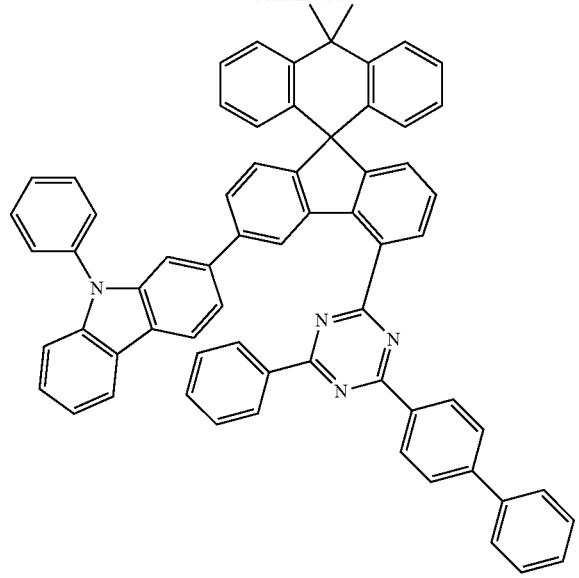
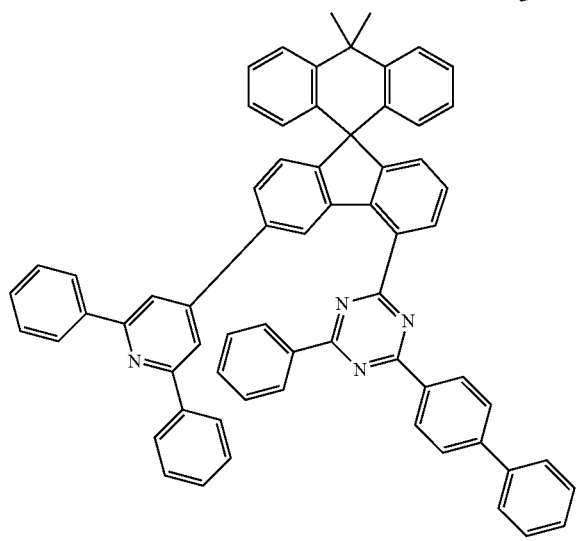
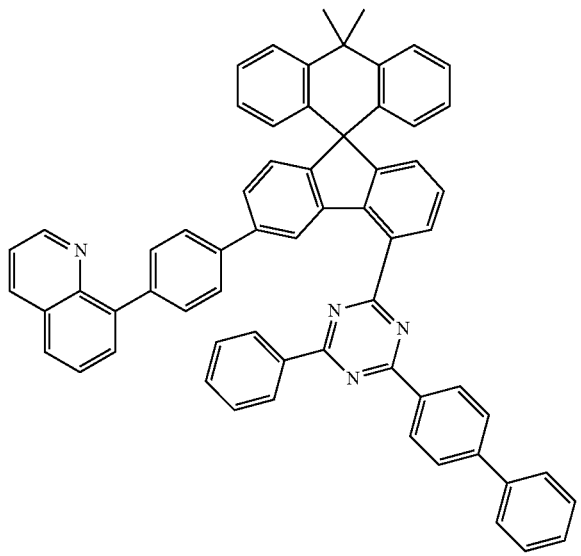
156
-continued
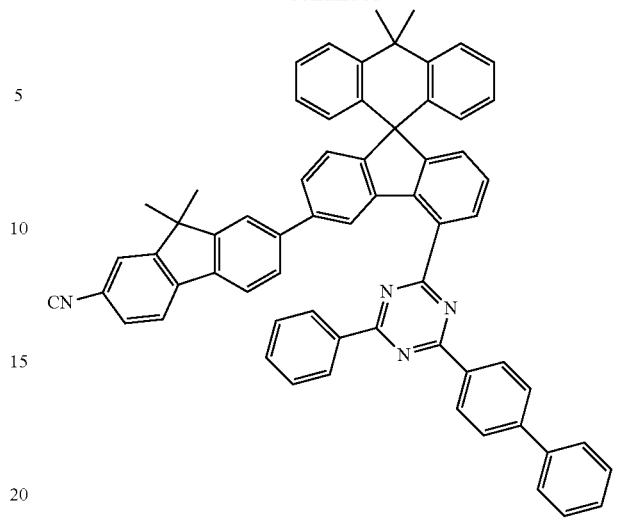
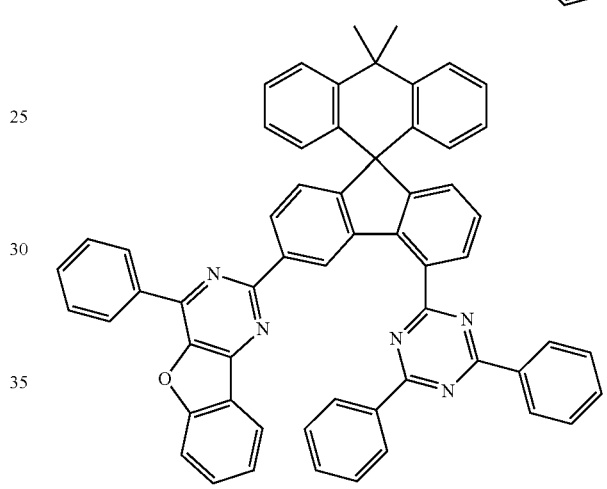
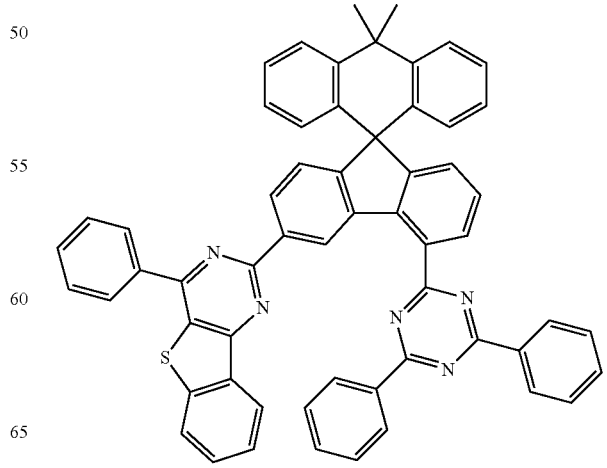

157
-continued
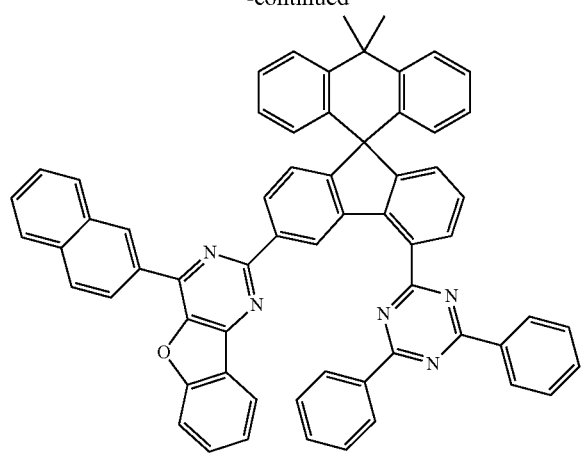
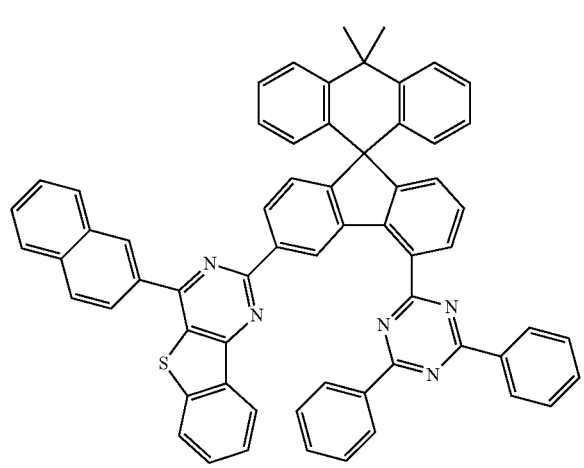
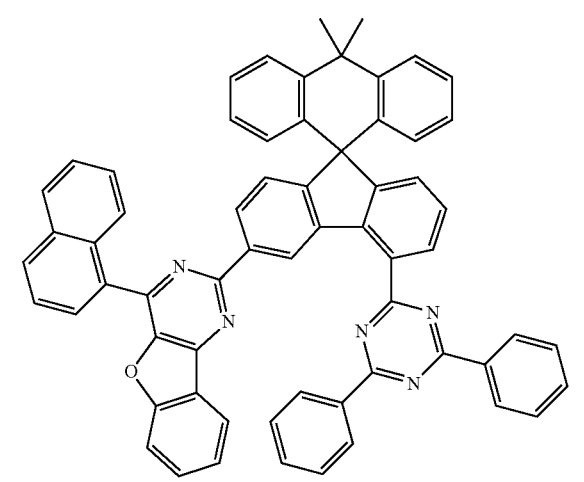
158
-continued
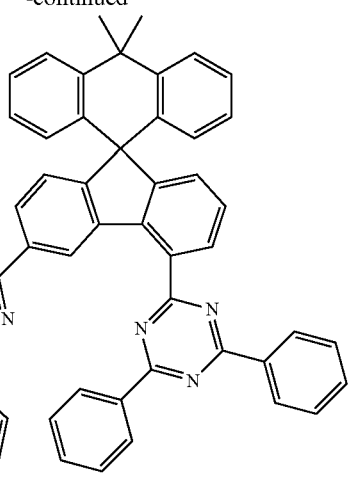
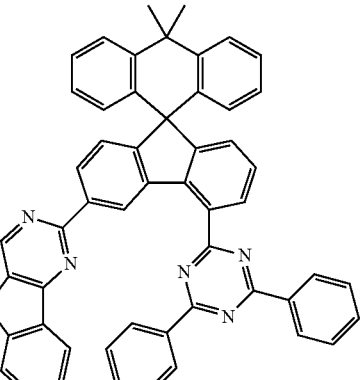
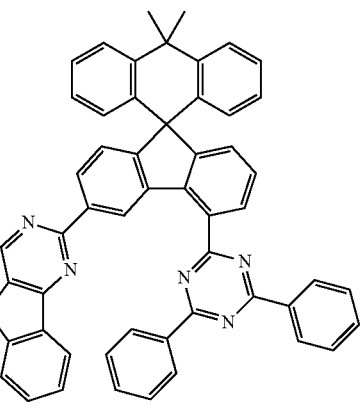
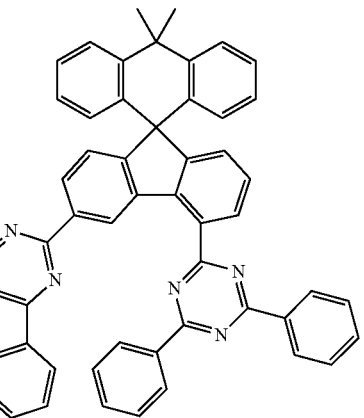

159
-continued
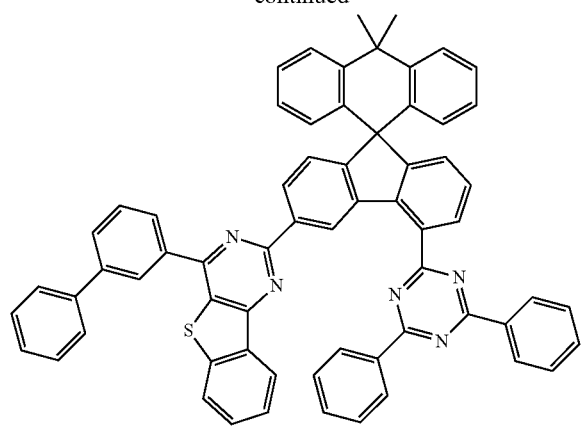
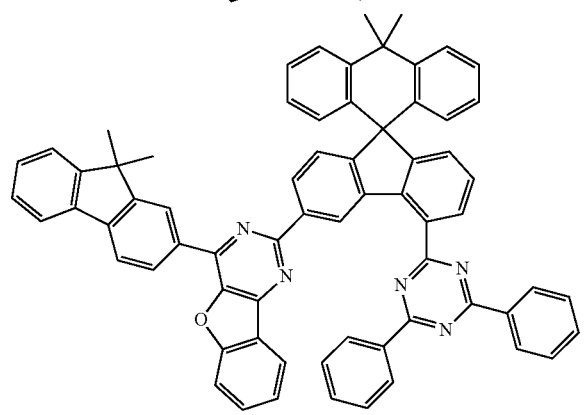
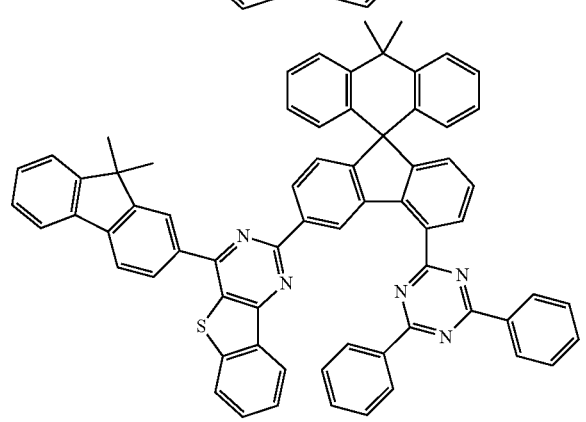
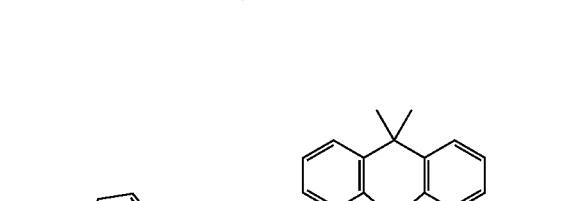
160
-continued
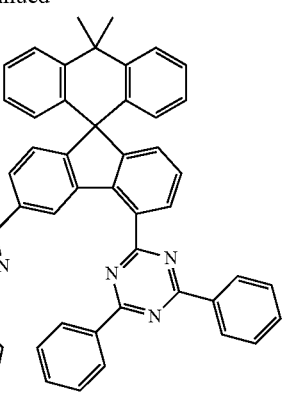
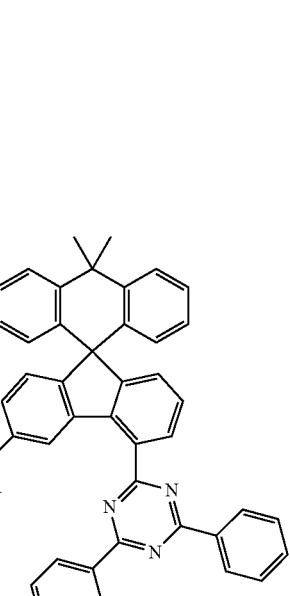
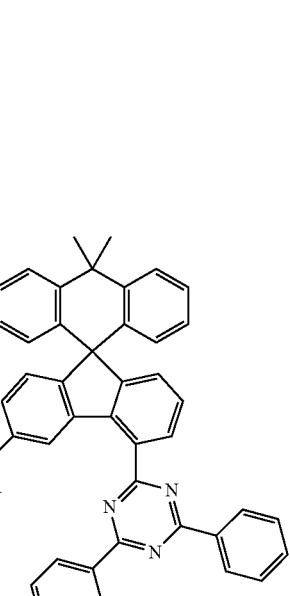

161
-continued
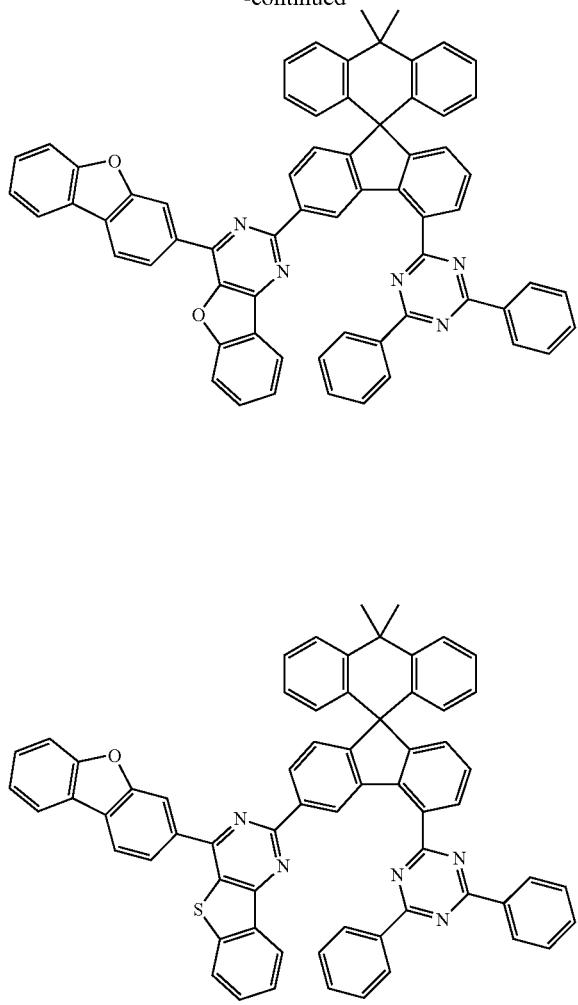
162
-continued
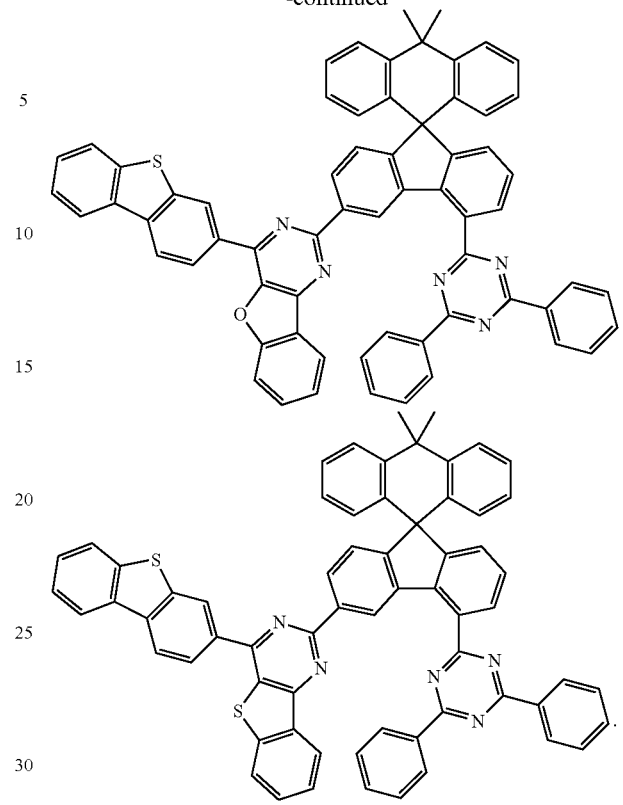
9. An organic light emitting device comprising a first electrode; a second electrode provided to face the first electrode; and at least one layer of organic material layers provided between the first electrode and the second electrode, wherein the at least one layer of the organic material layers includes a compound according to claim 1.
* * * * *